US012221484B2

(12) United States Patent
Dessain et al.

(10) Patent No.: US 12,221,484 B2
(45) Date of Patent: Feb. 11, 2025

(54) ANTI-NMDA RECEPTOR ANTIBODIES AND METHODS OF USE

(71) Applicant: Lankenau Institute for Medical Research, Wynnewood, PA (US)

(72) Inventors: Scott K. Dessain, Wynnewood, PA (US); Rashmi Sharma, King of Prussia, PA (US); Fetweh H. Al-Saleem, Philadelphia, PA (US)

(73) Assignee: Lankenau Institute for Medical Research, Wynnewood, PA (US)

( * ) Notice: Subject to any disclaimer, the term of this patent is extended or adjusted under 35 U.S.C. 154(b) by 790 days.

(21) Appl. No.: 17/599,399

(22) PCT Filed: Jun. 8, 2019

(86) PCT No.: PCT/US2019/036185
§ 371 (c)(1),
(2) Date: Sep. 28, 2021

(87) PCT Pub. No.: WO2020/204977
PCT Pub. Date: Oct. 8, 2020

(65) Prior Publication Data
US 2022/0073611 A1 Mar. 10, 2022

Related U.S. Application Data

(60) Provisional application No. 62/826,552, filed on Mar. 29, 2019.

(51) Int. Cl.
*G01N 33/53* (2006.01)
*C07K 16/28* (2006.01)
*G01N 33/564* (2006.01)

(52) U.S. Cl.
CPC ......... *C07K 16/286* (2013.01); *G01N 33/564* (2013.01); *G01N 2333/70571* (2013.01); *G01N 2800/24* (2013.01)

(58) Field of Classification Search
CPC .............. C07K 16/286; C07K 2317/21; C07K 2317/77; G01N 33/564; G01N 2333/70571; G01N 2800/24; G01N 33/6872; G01N 2800/28; A61K 2039/505; A61P 25/00
See application file for complete search history.

(56) References Cited

U.S. PATENT DOCUMENTS

| 7,972,796 | B2 | 5/2011 | Dalmau et al. |
| 2006/0140948 | A1 | 6/2006 | Foltz et al. |
| 2014/0212423 | A1 | 7/2014 | Hanzatian et al. |
| 2014/0235833 | A1 | 8/2014 | Sugioka et al. |
| 2018/0244802 | A1 | 8/2018 | Pruess |

FOREIGN PATENT DOCUMENTS

WO   WO 2008/021408 A2   2/2008

OTHER PUBLICATIONS

Rashmi Sharma et al, Ann Clin Transl Neurol. Aug. 2018; 5(8): 935-951. Published online Jul. 5, 2018.*
Sharma et al. "Monoclonal antibodies from a patient with anti-NMDA receptor encephalitis," Annals of Clinical and Translational Neurology, Jul. 5, 2018 (Jul. 5, 2018), vol. 5, No. 8, pp. 935-951.
Dalmau J, et al. Paraneoplastic anti-N methyl-D-aspartate receptor encephalitis associated with ovarian teratoma. Ann Neurol Jan. 2007; 61:25-36.
Armangue T, et al. Pediatric anti-N-methyl-D-aspartate receptor encephalitis-clinical analysis and novel findings in a series of 20 patients. J Pediatr Nov. 2012; 162:850-6e2.
Dalmau J, et al. Anti-NMDA receptor encephalitis: case series and analysis of the effects of antibodies. Lancet Neurol Nov. 2008; 7:1091.
Hughes EG, et al. Cellular and synaptic mechanisms of anti-NMDA receptor encephalitis. J Neurosci Apr. 2010;30:5866-5875.
Zhang Q, et al. Suppression of synaptic plasticity by cerebrospinal fluid from anti-NMDA receptor encephalitis patients. Neurobiol Dis Jan. 2012; 45:610-615.
Regan MC, et al. A structural biology perspective on NMDA receptor pharmacology and function. Curr Opin Struct Biol Aug. 2015; 33:68-75.
Gleichman AJ, et al. Anti-NMDA receptor encephalitis antibody binding is dependent on amino acid identity of a small region within the GluN1 amino terminal domain. J Neurosci Aug. 2012; 32:11082-11094.
Paoletti P, et al. NMDA receptor subunit diversity: impact on receptor properties, synaptic plasticity and disease. Nat Rev May 2013; 14:383-400.
Kreye J, et al. Human cerebrospinal fluid monoclonal N-methyl-D-aspartate receptor autoantibodies are sufficient for encephalitis pathogenesis. Brain Aug. 2016;139(Pt 10):2641-2652.
Puligedda RD, et al. Human monoclonal antibodies that neutralize vaccine and wildtype poliovirus strains. Antiviral Res Aug. 2014; 108:36-43.
Lai M, et al. AMPA receptor antibodies in limbic encephalitis alter synaptic receptorlocation. Ann Neurol Apr. 2009; 65:424-434.

(Continued)

*Primary Examiner* — Carmencita M Belei
(74) *Attorney, Agent, or Firm* — Howson & Howson LLC

(57) ABSTRACT

A recombinant, synthetic or monoclonal human antibody or fragment thereof that binds to an N-methyl-D-aspartate Receptor (NMDAR) epitope, which antibody or fragment comprises at least one a heavy chain variable domain sequence encoded by a nucleic acid sequence that is at least 80% identical to SEQ ID NOs. 1, 3, or 5; or at least one a light chain variable domain sequence encoded by a nucleic acid sequence that is at least 80% identical to SEQ ID NOs: 2, 4, or 6. Assays for diagnosis of ANRE employ these NMDAR-binding antibodies, constructs, or epitope binding fragments. In one embodiment, multiple of the NMDAR-binding antibodies or fragments are used as controls because they bind non-overlapping target sequences on the NMDAR ATD.

10 Claims, 26 Drawing Sheets

Specification includes a Sequence Listing.

(56) References Cited

OTHER PUBLICATIONS

Ho M, Pastan I. Display and selection of scFv antibodies on HEK-293T cells. Methods Mol Biol Feb. 2009; 562:99-113.
Erdile LF, et al. Whole cell ELISA for detection of tumor antigen expression in tumor samples. J Immunol Methods Dec. 2001;258(1-2):47-53.
Adekar SP, et al. Hybridoma populations enriched for affinity-matured human IgGs yield high-affinity antibodies specific for botulinum neurotoxins. J Immunol Methods Feb. 2008;333(1-2):156-166.
Lim TS, et al. V-gene amplificationrevisited—An optimised procedure for amplification of rearranged human antibody genes of different isotypes. New Biotechnol May 2010; 27:108-117.
Zhang J, et al. PEAR: a fast and accurate Illumina paired-end reAd mergeR. Bioinformatics Oct. 2013; 30:614-620.
Bolotin DA, et al. MiXCR: software for comprehensive adaptive immunity profiling. Nat Methods May 2015; 12:380-381.
Katoh K, et al. MAFFT: a novel method for rapid multiple sequence alignment based on fast Fourier transform. Nucleic Acids Res May 2002; 30:3059-3066.
Stamatakis A. RAxML version 8: a tool for phylogenetic analysis and post-analysis of large phylogenies. Bioinformatics Jan. 2014; 30:1312-1313.
Buchhalter JR, Dichter MA. Electrophysiological comparison of pyramidal and stellate nonpyramidal neurons in dissociated cell culture of rat hippocampus. Brain Res Bull Aug. 1991; 26:333-338.
Van der Staay FJ, et al. Effects of the cognition impairer MK-801 on learning and memory in mice and rats. Behav Brain Res Jan. 2011; 220:215-229.
Karakas E, et al. Emerging structural insights into the function of ionotropic glutamate receptors. Trends Biochem Sci May 2015; 40:328-337.
Al-Saleem FH, et al. RBC adherence of immune complexes containing botulinum toxin improves neutralization and macrophage uptake. Toxins May 2017

FIG. 4A
FIG. 4B
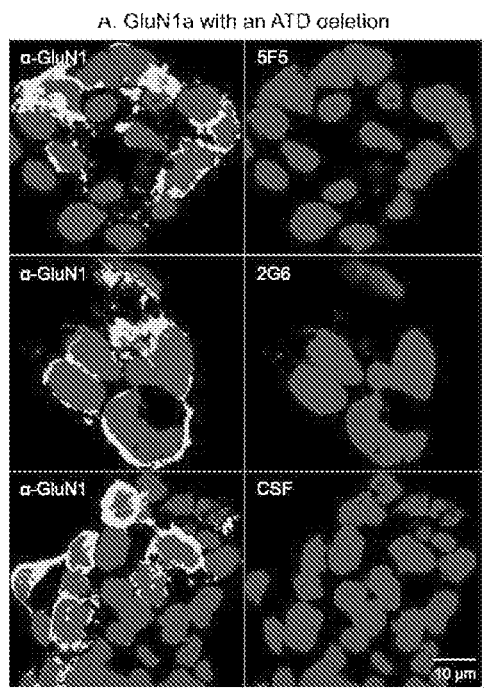
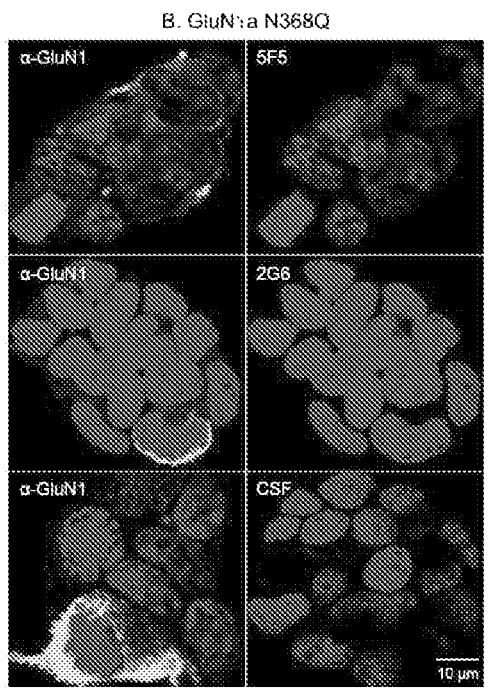

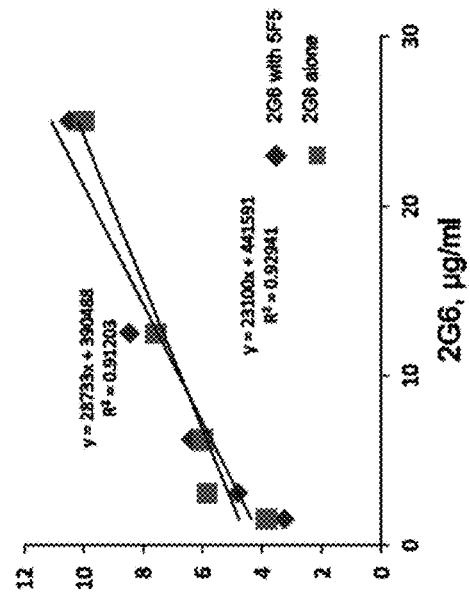
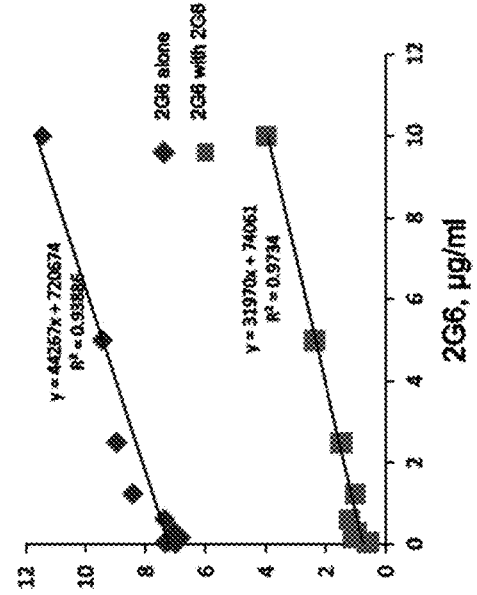
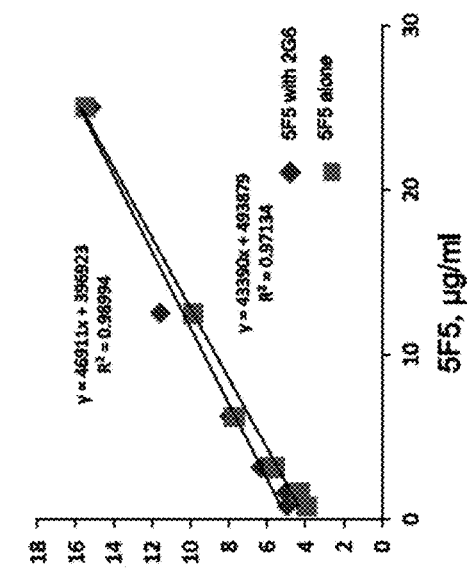
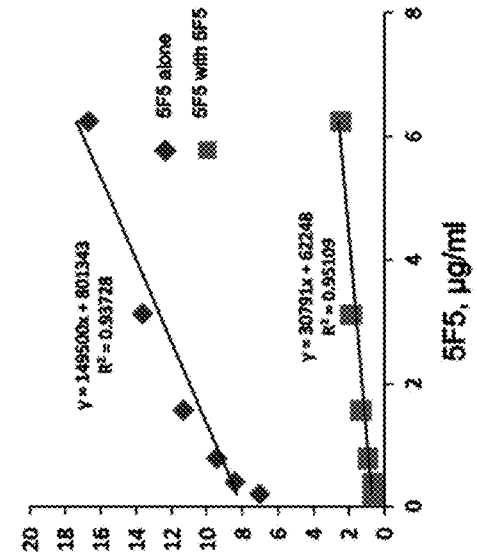

FIG. 9A
FIG. 9B
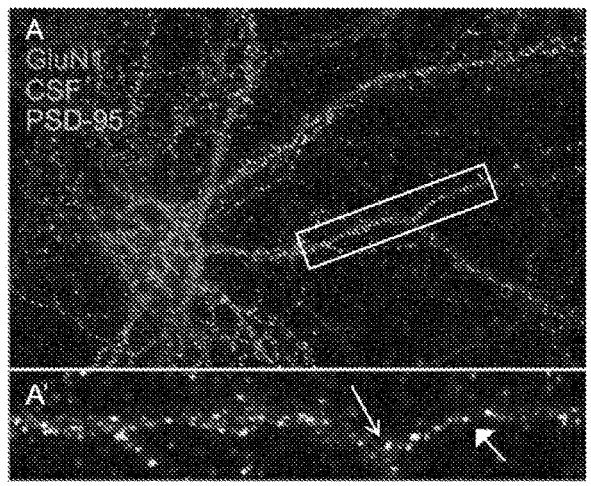
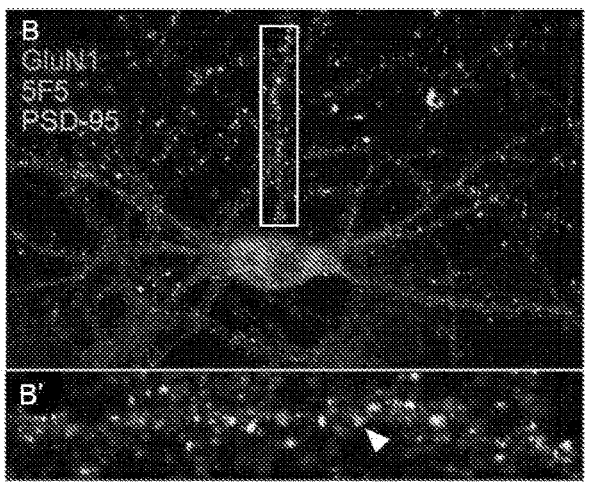
FIG. 9C
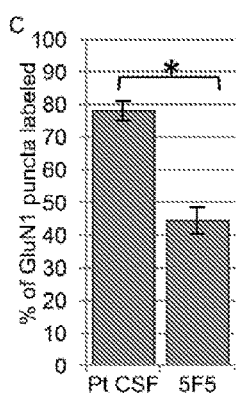
FIG. 9D
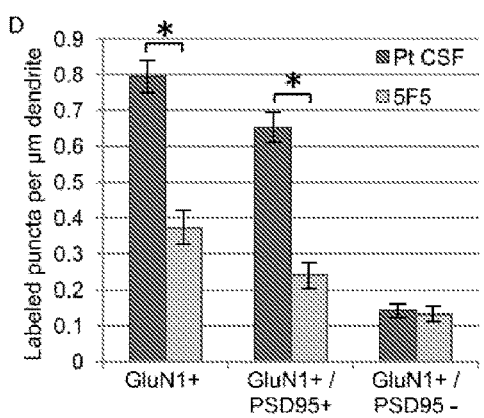

FIG. 12A
FIG. 12B
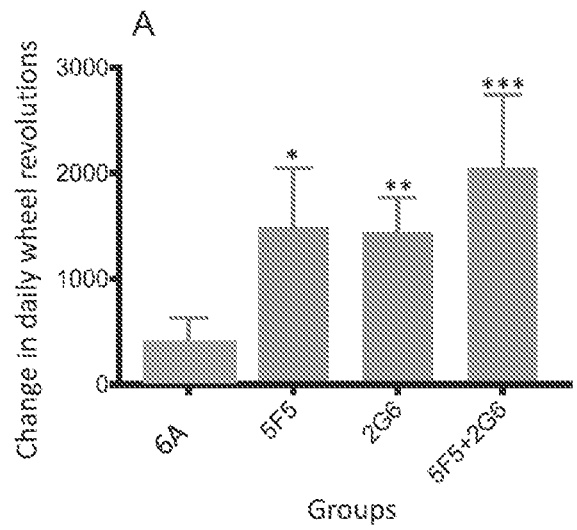
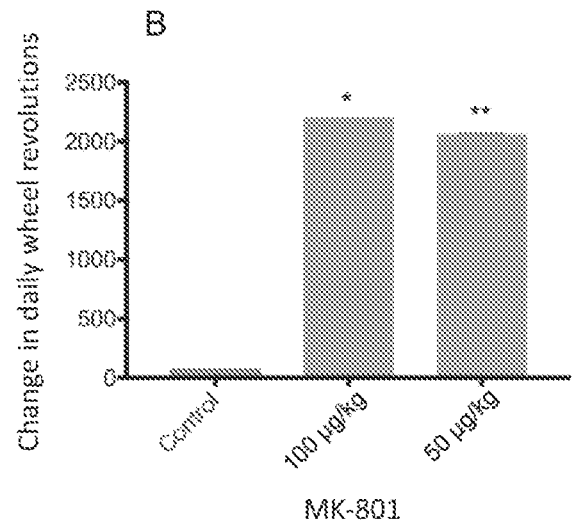

1D1 staining with ATD cells

FIG. 16A
FIG. 16B
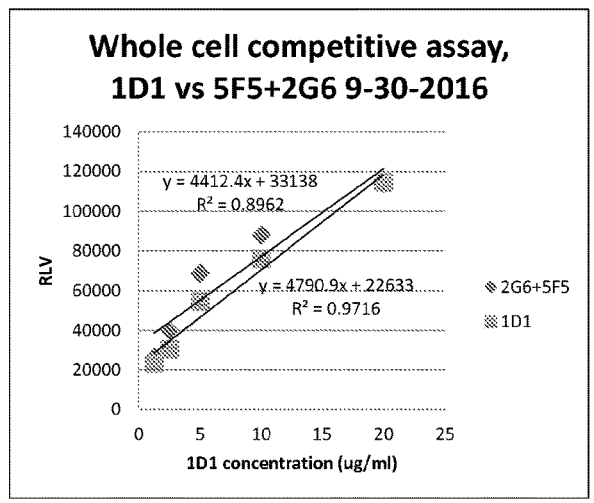
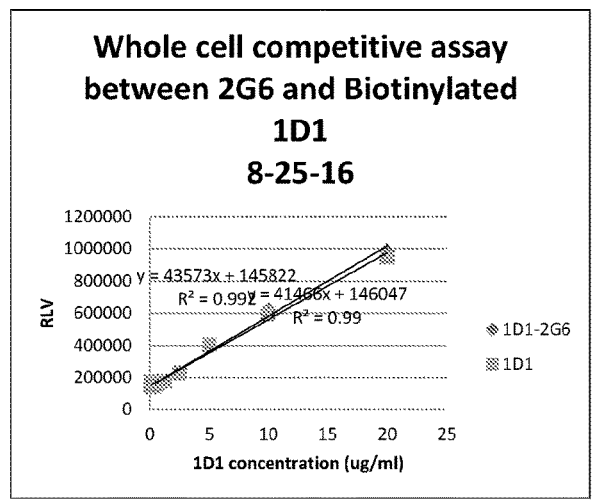

FIG. 22A
FIG. 22B
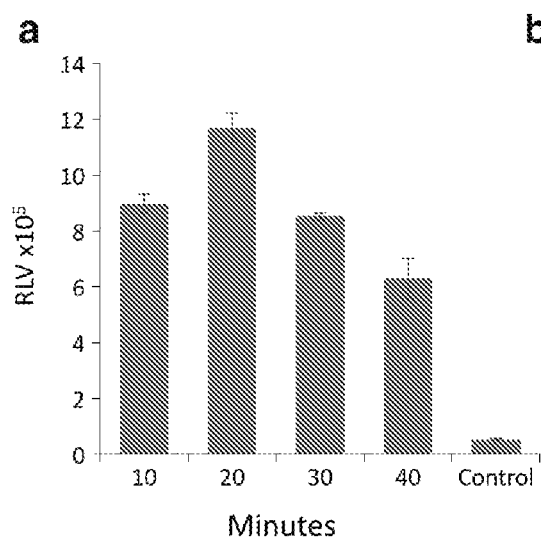
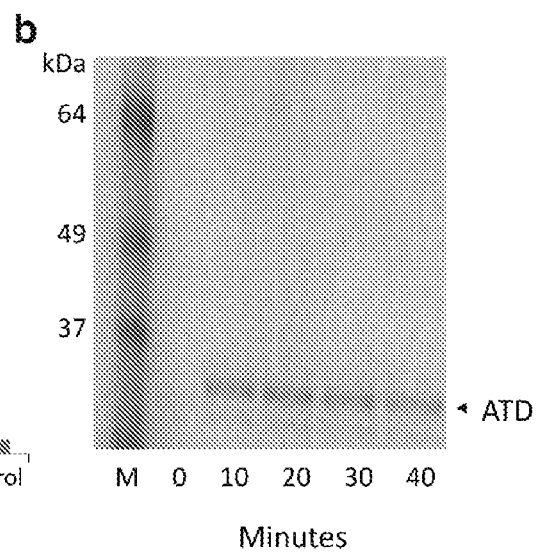

FIG. 23A
FIG. 23B
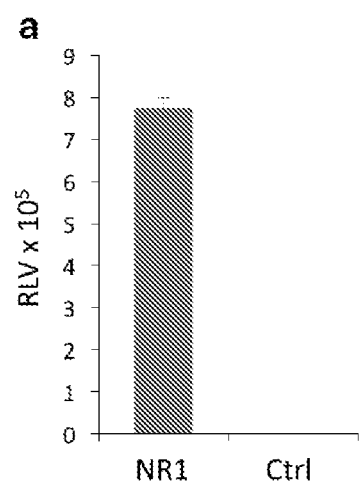
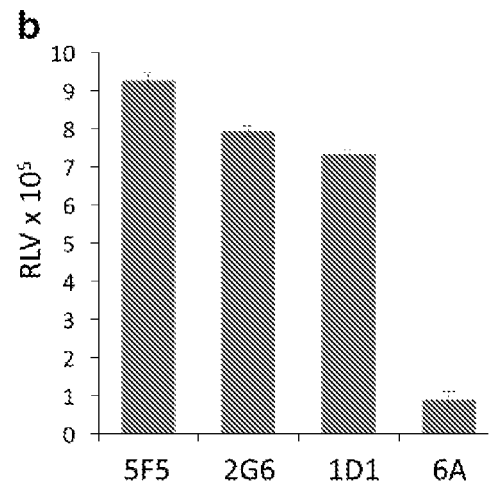

SEQUENCE LISTING

```
<160> NUMBER OF SEQ ID NOS: 17

<210> SEQ ID NO 1
<211> LENGTH: 385
<212> TYPE: DNA
<213> ORGANISM: artificial sequence
<220> FEATURE:
<223> OTHER INFORMATION: 5F5 heavy chain nt sequence

<400> SEQUENCE: 1
caggtgcagc tggtggagtc tggaggaggc gtggtccggc ctgggggtc cctgagactc        60 tcttgtgcag cctctggatt caccttcagt acctatagtc ttcactgggt ccgccaggct      120
ccaggcaagg ggctggagtg ggttggagtt attttatatg atggcagcaa aaaatattat      180
gcagactccg tgagggccg attcaccatc tccagagaca attccaagag cacgctaaat      240
ctggatatga gcagcctgag acctgacgac acggctgtgt attactgtgc gagagaccca      300
atagcagtgg ctcccaggcc cagcggcatg gtcccccagg gatttgacta ttggggccag      360
ggaaccctgg tcaccgtctc ctcag                                             385

<210> SEQ ID NO 2
<211> LENGTH: 331
<212> TYPE: DNA
<213> ORGANISM: Artificial Sequence
<220> FEATURE:
<223> OTHER INFORMATION: 5F5 light chain nt

<400> SEQUENCE: 2
cagtctgtcg tgacgcagcc gccctcagcg tctgggaccc ccgggcagag ggtcaccatc        60
tcctgttctg gaagcagctc caacatcgga agaaattttg tattctggta tcggcagctc      120
ccaggaacgg cccccaaagt cctcatctat aagaatattc agcggccctc aggggtccct      180
gaccgaatct ctggctccag gtctggctcc tcagcctccc tggccatcag tggactccgg      240
```

```
tccgaggatg aggctgatta ttactgtgca tcatgggatg acagcctgag tggtgtggtg     300
ttcggcgggg ggaccaagct gaccgtccta a                                    331

<210> SEQ ID NO 3
<211> LENGTH: 392
<212> TYPE: DNA
<213> ORGANISM: artificial
<220> FEATURE:
<223> OTHER INFORMATION: 2G6 heavy chain nt

<400> SEQUENCE: 3
caggtgcagc tgcaggagtc ggggggaggc gtggtccagc ctgggaggtc cctgagactc      60
tcctgtgcag cctctgggtt cagcttcaat gcctttgcca tgcactgggt ccgccaggct     120
ccaggcaagg ggctggagtg ggtggcacgc atatcacatt atggaagtga tgactactat     180
gcagactctg tgaagggccg attcaccatc tccagagaca attcccagaa cactctgttt     240
ctgcaaatga acagcctgaa agccgaggac acgggtgtgt attactgttg gaggggattt     300
actctggttc ggggagttat ttcgagaaat cccattaatc gattctccgg tatggacgtc     360
tggggccaag ggaccacggt caccgtctct tc                                   392

<210> SEQ ID NO 4
<211> LENGTH: 325
<212> TYPE: DNA
<213> ORGANISM: artificial
<220> FEATURE:
<223> OTHER INFORMATION: 2G6 light chain nt

<400> SEQUENCE: 4
tcctatgagc tgatgcagcc accctcggtg tcagtgtccc caggacaaac ggccaggatc      60
acctgctctg gagatgcatt gccaaaaaaa tatgcttatt ggtaccagca gaagtcaggc     120
caggccccta tactggtcat ctatgaggac aacaaacgac cctccgggat ccctgagaga     180
ttctctggct ccagctcagg gacaatggcc accttgacta tcagtggggc caggtggag      240 gatgaagctg actacttctg ttattcaaca gacagcagtg gtaatcatgg ggtattcggc     300
ggagggacca agctgaccgt cctaa                                           325

<210> SEQ ID NO 5
<211> LENGTH: 361
<212> TYPE: DNA
<213> ORGANISM: Artificial Sequence
<220> FEATURE:
<223> OTHER INFORMATION: 1D1 heavy chain nt

<400> SEQUENCE: 5
ttggtgcagc tggtggagtc cggggggagc gtggtccagt ctgggaggtc cctgagactc      60
tcctgtgcag cctctggatt cgccttccat acctttacta tacactgggt ccgccaggct     120
ccaggcaagg ggctggactg ggtaacagct atatatttg atggaaccaa aaaatactac     180
gcagactccg tgaagggccg attcaccgtc tccagagaca ctccaagaa cacggtatat     240 ctgcaaatga acggcctgag aggtgaggac acggctgtct attactgtgc gagagcccga     300
tacagctatg gcctttcctt tgactactgg ggccagggaa ccccggtcac cgtctcctct     360
g                                                                     361

<210> SEQ ID NO 6
<211> LENGTH: 331
<212> TYPE: DNA
<213> ORGANISM: Artificial Sequence
```

<220> FEATURE:
<223> OTHER INFORMATION: 1D1 light chain nt

<400> SEQUENCE: 6

```
cagtctgtcg tgacgcagcc gccctcagtg tctgcggccc caggacagaa ggtcaccatc      60
tcctgctctg caagcagctc ctaccttggg agtaattatg tatccttggta ccagcaactc    120
ccaggaacag cccccaaact cctcatttat gacaataata agcgatcctc agggatttct    180
gaccgattct ctggctccaa gtctggcacg tcagccaccc tggacatcac cggcctgcag    240
actggggacg aggccgacta ttactgcgga gcatgggaca gcagcctgag tgtcgtggtt    300
ttcggcggag ggaccaagct gaccgtccta a                                    331
```

<210> SEQ ID NO 7
<211> LENGTH: 561
<212> TYPE: PRT
<213> ORGANISM: Artificial Sequence
<220> FEATURE:
<223> OTHER INFORMATION: NMDAR amino terminal domain

<400> SEQUENCE: 7

```
Met Ser Thr Met Arg Leu Leu Thr Leu Ala Leu Leu Phe Ser Cys Ser
1               5                   10                  15

Val Ala Arg Ala Ala Cys Asp Pro Lys Ile Val Asn Ile Gly Ala Val
            20                  25                  30

Leu Ser Thr Arg Lys His Glu Gln Met Phe Arg Glu Ala Val Asn Gln
        35                  40                  45

Ala Asn Lys Arg His Gly Ser Trp Lys Ile Gln Leu Asn Ala Thr Ser
    50                  55                  60

Val Thr His Lys Pro Asn Ala Ile Gln Met Ala Leu Ser Val Cys Glu
65                  70                  75                  80

Asp Leu Ile Ser Ser Gln Val Tyr Ala Ile Leu Val Ser His Pro Pro
                85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
        115                 120                 125

Ser Asp Lys Ser Ile His Leu Ser Phe Leu Arg Thr Val Pro Pro Tyr
    130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ala Glu
            180                 185                 190

Lys Val Leu Gln Phe Asp Pro Gly Thr Lys Asn Val Thr Ala Leu Leu
        195                 200                 205

Met Glu Ala Lys Glu Leu Glu Ala Arg Val Ile Ile Leu Ser Ala Ser
    210                 215                 220

Glu Asp Asp Ala Ala Thr Val Tyr Arg Ala Ala Met Leu Asn Met
225                 230                 235                 240

Thr Gly Ser Gly Tyr Val Trp Leu Val Gly Glu Arg Glu Ile Ser Gly
                245                 250                 255

Asn Ala Leu Arg Tyr Ala Pro Asp Gly Ile Leu Gly Leu Gln Leu Ile
            260                 265                 270

Asn Gly Lys Asn Glu Ser Ala His Ile Ser Asp Ala Val Gly Val Val
```

```
                    275                 280                 285
Ala Gln Ala Val His Glu Leu Leu Glu Lys Glu Asn Ile Thr Asp Pro
            290                 295                 300
Pro Arg Gly Cys Val Gly Asn Thr Asn Ile Trp Lys Thr Gly Pro Leu
305                 310                 315                 320
Phe Lys Arg Val Leu Met Ser Ser Lys Tyr Ala Asp Gly Val Thr Gly
                325                 330                 335
Arg Val Glu Phe Asn Glu Asp Gly Asp Arg Lys Phe Ala Asn Tyr Ser
            340                 345                 350
Ile Met Asn Leu Gln Asn Arg Lys Leu Val Gln Val Gly Ile Tyr Asn
                355                 360                 365
Gly Thr His Val Ile Pro Asn Asp Arg Lys Ile Ile Trp Pro Gly Gly
            370                 375                 380
Glu Thr Glu Lys Pro Arg Gly Tyr Gln Met Ser Thr Arg Leu Lys Ile
385                 390                 395                 400
Val Thr Ile His Gln Glu Pro Phe Val Tyr Val Lys Pro Thr Leu Ser
                405                 410                 415
Asp Gly Thr Cys Lys Glu Glu Phe Thr Val Asn Gly Asp Pro Val Lys
            420                 425                 430
Lys Val Ile Cys Thr Gly Pro Asn Asp Thr Ser Pro Gly Ser Pro Arg
            435                 440                 445
His Thr Val Pro Gln Cys Cys Tyr Gly Phe Cys Ile Asp Leu Leu Ile
            450                 455                 460
Lys Leu Ala Arg Thr Met Asn Phe Thr Tyr Glu Val His Leu Val Ala
465                 470                 475                 480
Asp Gly Lys Phe Gly Thr Gln Glu Arg Val Asn Asn Ser Asn Lys Lys
                485                 490                 495
Glu Trp Asn Gly Met Met Gly Glu Leu Leu Ser Gly Gln Ala Asp Met
            500                 505                 510
Ile Val Ala Pro Leu Thr Ile Asn Asn Glu Arg Ala Gln Tyr Ile Glu
            515                 520                 525
Phe Ser Lys Pro Phe Lys Tyr Gln Gly Leu Thr Ile Leu Val Lys Lys
530                 535                 540
Glu Ile Pro Arg Ser Thr Leu Asp Ser Phe Met Gln Pro Phe Gln Ser
545                 550                 555                 560
Thr

<210> SEQ ID NO 8
<211> LENGTH: 635
<212> TYPE: PRT
<213> ORGANISM: Artificial Sequence
<220> FEATURE:
<223> OTHER INFORMATION: fusion proteinof N-terminal extracellular
      domain of human GluN1 fused to the Myc epitope tag, a 6XHIS tag,
      the Tobacco Etch Virus (TEV) protease cleavage site and TM domain
      of human PDGFR
<220> FEATURE:
<221> NAME/KEY: ATD
<222> LOCATION: (1)..(561)
<223> OTHER INFORMATION: Human NR1 amino terminal domain
<220> FEATURE:
<221> NAME/KEY: Myc
<222> LOCATION: (562)..(571)
<223> OTHER INFORMATION: MYC domain
<220> FEATURE:
<221> NAME/KEY: polyHIS
<222> LOCATION: (572)..(577)
<223> OTHER INFORMATION: polyHis sequence
<220> FEATURE:
<221> NAME/KEY: Tev
```

<222> LOCATION: (578)..(585)
<223> OTHER INFORMATION: Tev protease
<220> FEATURE:
<221> NAME/KEY: DOMAIN
<222> LOCATION: (586)..(635)
<223> OTHER INFORMATION: transmembrane domain of human PDGFR

<400> SEQUENCE: 8

```
Met Ser Thr Met Arg Leu Leu Thr Leu Ala Leu Leu Phe Ser Cys Ser
1               5                   10                  15

Val Ala Arg Ala Ala Cys Asp Pro Lys Ile Val Asn Ile Gly Ala Val
            20                  25                  30

Leu Ser Thr Arg Lys His Glu Gln Met Phe Arg Glu Ala Val Asn Gln
        35                  40                  45

Ala Asn Lys Arg His Gly Ser Trp Lys Ile Gln Leu Asn Ala Thr Ser
    50                  55                  60

Val Thr His Lys Pro Asn Ala Ile Gln Met Ala Leu Ser Val Cys Glu
65                  70                  75                  80

Asp Leu Ile Ser Ser Gln Val Tyr Ala Ile Leu Val Ser His Pro Pro
                85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
        115                 120                 125

Ser Asp Lys Ser Ile His Leu Ser Phe Leu Arg Thr Val Pro Pro Tyr
    130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ala Glu
            180                 185                 190

Lys Val Leu Gln Phe Asp Pro Gly Thr Lys Asn Val Thr Ala Leu Leu
        195                 200                 205

Met Glu Ala Lys Glu Leu Glu Ala Arg Val Ile Ile Leu Ser Ala Ser
    210                 215                 220

Glu Asp Asp Ala Ala Thr Val Tyr Arg Ala Ala Ala Met Leu Asn Met
225                 230                 235                 240

Thr Gly Ser Gly Tyr Val Trp Leu Val Gly Glu Arg Glu Ile Ser Gly
                245                 250                 255

Asn Ala Leu Arg Tyr Ala Pro Asp Gly Ile Leu Gly Leu Gln Leu Ile
            260                 265                 270

Asn Gly Lys Asn Glu Ser Ala His Ile Ser Asp Ala Val Gly Val Val
        275                 280                 285

Ala Gln Ala Val His Glu Leu Leu Glu Lys Glu Asn Ile Thr Asp Pro
    290                 295                 300

Pro Arg Gly Cys Val Gly Asn Thr Asn Ile Trp Lys Thr Gly Pro Leu
305                 310                 315                 320

Phe Lys Arg Val Leu Met Ser Ser Lys Tyr Ala Asp Gly Val Thr Gly
                325                 330                 335

Arg Val Glu Phe Asn Glu Asp Gly Asp Arg Lys Phe Ala Asn Tyr Ser
            340                 345                 350

Ile Met Asn Leu Gln Asn Arg Lys Leu Val Gln Val Gly Ile Tyr Asn
        355                 360                 365

Gly Thr His Val Ile Pro Asn Asp Arg Lys Ile Ile Trp Pro Gly Gly
```

```
                370             375              380
Glu Thr Glu Lys Pro Arg Gly Tyr Gln Met Ser Thr Arg Leu Lys Ile
385                 390                 395                 400

Val Thr Ile His Gln Glu Pro Phe Val Tyr Val Lys Pro Thr Leu Ser
                405                 410                 415

Asp Gly Thr Cys Lys Glu Glu Phe Thr Val Asn Gly Asp Pro Val Lys
            420                 425                 430

Lys Val Ile Cys Thr Gly Pro Asn Asp Thr Ser Pro Gly Ser Pro Arg
        435                 440                 445

His Thr Val Pro Gln Cys Cys Tyr Gly Phe Cys Ile Asp Leu Leu Ile
    450                 455                 460

Lys Leu Ala Arg Thr Met Asn Phe Thr Tyr Glu Val His Leu Val Ala
465                 470                 475                 480

Asp Gly Lys Phe Gly Thr Gln Glu Arg Val Asn Asn Ser Asn Lys Lys
                485                 490                 495

Glu Trp Asn Gly Met Met Gly Glu Leu Leu Ser Gly Gln Ala Asp Met
            500                 505                 510

Ile Val Ala Pro Leu Thr Ile Asn Asn Glu Arg Ala Gln Tyr Ile Glu
        515                 520                 525

Phe Ser Lys Pro Phe Lys Tyr Gln Gly Leu Thr Ile Leu Val Lys Lys
    530                 535                 540

Glu Ile Pro Arg Ser Thr Leu Asp Ser Phe Met Gln Pro Phe Gln Ser
545                 550                 555                 560

Thr Glu Gln Lys Leu Ile Ser Glu Glu Asp Leu His His His His His
                565                 570                 575

His Glu Asn Leu Tyr Phe Gln Gly Gly Asn Ala Val Gly Gln Asp Thr
            580                 585                 590

Gln Glu Val Ile Val Val Pro His Ser Leu Pro Phe Lys Val Val Val
        595                 600                 605

Ile Ser Ala Ile Leu Ala Leu Val Val Leu Thr Ile Ile Ser Leu Ile
    610                 615                 620

Ile Leu Ile Met Leu Trp Gln Lys Lys Pro Arg
625                 630                 635

<210> SEQ ID NO 9
<211> LENGTH: 1926
<212> TYPE: DNA
<213> ORGANISM: Artificial Sequence
<220> FEATURE:
<223> OTHER INFORMATION: DNA sequence encoding the fusion protein of SEQ
      ID NO: 8

<400> SEQUENCE: 9
ggatccgcca ccatgagcac catgcgcctg ctgacgctcg ccctgctgtt ctcctgctcc      60
gtcgcccgtg ccgcgtgcga ccccaagatc gtcaacattg gcgcggtgct gagcacgcgg     120
aagcacgagc agatgttccg cgaggccgtg aaccaggcca caagcggca cggctcctgg     180 aagattcagc tcaatgccac ctccgtcacg cacaagccca cgccatcca gatggctctg     240 tcggtgtgcg aggacctcat ctccagccag gtctacgcca tcctagttag ccatccacct     300 accccaacg accacttcac tcccaccct gtctcctaca cagccggctt ctaccgcata      360
cccgtgctgg ggctgaccac ccgcatgtcc atctactcgg acaagagcat ccacctgagc     420
ttcctgcgca ccgtgccgcc ctactcccac cagtccagct gtggtttga gatgatgcgt     480 gtctacagct ggaaccacat catcctgctg gtcagcgacg accacgaggg ccgggcggct     540
```

```
cagaaacgcc tggagacgct gctggaggag cgtgagtcca aggcagagaa ggtgctgcag    600
tttgacccag ggaccaagaa cgtgacggcc ctgctgatgg aggcgaaaga gctggaggcc    660
cgggtcatca tcctttctgc cagcgaggac gatgctgcca ctgtataccg cgcagccgcg    720
atgctgaaca tgacgggctc cgggtacgtg tggctggtcg gcgagcgcga gatctcgggg    780
aacgccctgc gctacgcccc agacggcatc ctcgggctgc agctcatcaa cggcaagaac    840
gagtcggccc acatcagcga cgccgtgggc gtggtggccc aggccgtgca cgagctcctc    900
gagaaggaga acatcaccga cccgccgcgg ggctgcgtgg caacaccaa catctggaag     960 accgggccgc tcttcaagag agtgctgatg tcttccaagt atgcggatgg ggtgactggt   1020
cgcgtggagt tcaatgagga tggggaccgg aagttcgcca actacagcat catgaacctg   1080
cagaaccgca agctggtgca agtgggcatc tacaatggca cccacgtcat ccctaatgac   1140
aggaagatca tctggccagg cggagagaca gagaagcctc gagggtacca gatgtccacc   1200
agactgaaga ttgtgacgat ccaccaggag cccttcgtgt acgtcaagcc cacgctgagt   1260
gatgggacat gcaaggagga gttcacagtc aacggcgacc cagtcaagaa ggtgatctgc   1320
accgggccca acgacacgtc gccgggcagc ccccgccaca cggtgcctca gtgttgctac   1380
ggcttttgca tcgacctgct catcaagctg gcacggacca tgaacttcac ctacgaggtg   1440
cacctggtgg cagatggcaa gttcggcaca caggagcggg tgaacaacag caacaagaag   1500
gagtggaatg ggatgatggg cgagctgctc agcgggcagg cagacatgat cgtggcgccg   1560
ctaaccataa acaacgagcg cgcgcagtac atcgagtttt ccaagcccct caagtaccag   1620
ggcctgacta ttctggtcaa gaaggagatt ccccggagca cgctggactc gttcatgcag   1680
ccgttccaga gcacagaaca aaaactcatc tcagaagagg atctgcatca tcaccatcac   1740
cacgaaaacc tgtattttca gggcggcaac gctgtgggcc aggacacgca ggaggtcatc   1800
gtggtgccac actccttgcc ctttaaggtg gtggtgatct cagccatcct ggccctggtg   1860
gtgctcacca tcatctccct tatcatcctc atcatgcttt ggcagaagaa gccacgttag   1920
gaattc                                                              1926
```

<210> SEQ ID NO 10
<211> LENGTH: 128
<212> TYPE: PRT
<213> ORGANISM: Artificial Sequence
<220> FEATURE:
<223> OTHER INFORMATION: 5F5 heavy chain AA
<220> FEATURE:
<221> NAME/KEY: CDR
<222> LOCATION: (97)..(117)
<223> OTHER INFORMATION: CDR region
<400> SEQUENCE: 10

```
Gln Val Gln Leu Val Glu Ser Gly Gly Gly Val Arg Pro Gly Gly
1               5                   10                  15

Ser Leu Arg Leu Ser Cys Ala Ala Ser Gly Phe Thr Phe Ser Thr Tyr
            20                  25                  30

Ser Leu His Trp Val Arg Gln Ala Pro Gly Lys Gly Leu Glu Trp Val
        35                  40                  45

Gly Val Ile Leu Tyr Asp Gly Ser Lys Lys Tyr Tyr Ala Asp Ser Val
    50                  55                  60

Arg Gly Arg Phe Thr Ile Ser Arg Asp Asn Ser Lys Ser Thr Leu Asn
65                  70                  75                  80

Leu Asp Met Ser Ser Leu Arg Pro Asp Asp Thr Ala Val Tyr Tyr Cys
                85                  90                  95
```

Ala Arg Asp Pro Ile Ala Val Ala Pro Arg Pro Ser Gly Met Val Pro
            100                 105                 110

Gln Gly Phe Asp Tyr Trp Gly Gln Gly Thr Leu Val Thr Val Ser Ser
        115                 120                 125

<210> SEQ ID NO 11
<211> LENGTH: 110
<212> TYPE: PRT
<213> ORGANISM: Artificial Sequence
<220> FEATURE:
<223> OTHER INFORMATION: 5F5 light chain AA
<220> FEATURE:
<221> NAME/KEY: CDR
<222> LOCATION: (88)..(101)
<223> OTHER INFORMATION: CDR region

<400> SEQUENCE: 11

Gln Ser Val Val Thr Gln Pro Pro Ser Ala Ser Gly Thr Pro Gly Gln
1               5                   10                  15

Arg Val Thr Ile Ser Cys Ser Gly Ser Ser Asn Ile Gly Arg Asn
            20                  25                  30

Phe Val Phe Trp Tyr Arg Gln Leu Pro Gly Thr Ala Pro Lys Val Leu
        35                  40                  45

Ile Tyr Lys Asn Ile Gln Arg Pro Ser Gly Val Pro Asp Arg Ile Ser
    50                  55                  60

Gly Ser Arg Ser Gly Ser Ser Ala Ser Leu Ala Ile Ser Gly Leu Arg
65                  70                  75                  80

Ser Glu Asp Glu Ala Asp Tyr Tyr Cys Ala Ser Trp Asp Asp Ser Leu
                85                  90                  95

Ser Gly Val Val Phe Gly Gly Gly Thr Lys Leu Thr Val Leu
            100                 105                 110

<210> SEQ ID NO 12
<211> LENGTH: 130
<212> TYPE: PRT
<213> ORGANISM: Artificial Sequence
<220> FEATURE:
<223> OTHER INFORMATION: 2G6 heavy chain AA
<220> FEATURE:
<221> NAME/KEY: CDR
<222> LOCATION: (97)..(120)
<223> OTHER INFORMATION: CDR region

<400> SEQUENCE: 12

Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Ser Phe Asn Ala Phe
            20                  25                  30

Ala Met His Trp Val Arg Gln Ala Pro Gly Lys Gly Leu Glu Trp Val
        35                  40                  45

Ala Arg Ile Ser His Tyr Gly Ser Asp Tyr Tyr Ala Asp Ser Val
    50                  55                  60

Lys Gly Arg Phe Thr Ile Ser Arg Asp Asn Ser Gln Asn Thr Leu Phe
65                  70                  75                  80

Leu Gln Met Asn Ser Leu Lys Ala Glu Asp Thr Gly Val Tyr Tyr Cys
                85                  90                  95

Trp Arg Gly Phe Thr Leu Val Arg Gly Val Ile Ser Arg Asn Pro Ile
            100                 105                 110

Asn Arg Phe Ser Gly Met Asp Val Trp Gly Gln Gly Thr Thr Val Thr
        115                 120                 125

```
Val Ser
    130

<210> SEQ ID NO 13
<211> LENGTH: 108
<212> TYPE: PRT
<213> ORGANISM: Artificial Sequence
<220> FEATURE:
<223> OTHER INFORMATION: 2G6 light chain AA
<220> FEATURE:
<221> NAME/KEY: CDR
<222> LOCATION: (87)..(99)
<223> OTHER INFORMATION: CDR region

<400> SEQUENCE: 13

Ser Tyr Glu Leu Met Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Tyr Trp Tyr Gln Gln Lys Ser Gly Gln Ala Pro Ile Leu Val Ile Tyr
        35                  40                  45

Glu Asp Asn Lys Arg Pro Ser Gly Ile Pro Glu Arg Phe Ser Gly Ser
    50                  55                  60

Ser Ser Gly Thr Met Ala Thr Leu Thr Ile Ser Gly Ala Gln Val Glu
65                  70                  75                  80

Asp Glu Ala Asp Tyr Phe Cys Tyr Ser Thr Asp Ser Ser Gly Asn His
                85                  90                  95

Gly Val Phe Gly Gly Gly Thr Lys Leu Thr Val Leu
            100                 105

<210> SEQ ID NO 14
<211> LENGTH: 120
<212> TYPE: PRT
<213> ORGANISM: Artificial Sequence
<220> FEATURE:
<223> OTHER INFORMATION: 1D1 heavy chain AA
<220> FEATURE:
<221> NAME/KEY: CDR
<222> LOCATION: (97)..(109)
<223> OTHER INFORMATION: CDR region

<400> SEQUENCE: 14

Leu Val Gln Leu Val Glu Ser Gly Gly Gly Val Val Gln Ser Gly Arg
1               5                   10                  15

Ser Leu Arg Leu Ser Cys Ala Ala Ser Gly Phe Ala Phe His Thr Phe
            20                  25                  30

Thr Ile His Trp Val Arg Gln Ala Pro Gly Lys Gly Leu Asp Trp Val
        35                  40                  45

Thr Ala Ile Tyr Phe Asp Gly Thr Lys Lys Tyr Ala Asp Ser Val
    50                  55                  60

Lys Gly Arg Phe Thr Val Ser Arg Asp Asn Ser Lys Asn Thr Val Tyr
65                  70                  75                  80

Leu Gln Met Asn Gly Leu Arg Gly Glu Asp Thr Ala Val Tyr Tyr Cys
                85                  90                  95

Ala Arg Ala Arg Tyr Ser Tyr Gly Leu Ser Phe Asp Tyr Trp Gly Gln
            100                 105                 110

Gly Thr Pro Val Thr Val Ser Ser
        115                 120

<210> SEQ ID NO 15
```

```
<211> LENGTH: 110
<212> TYPE: PRT
<213> ORGANISM: Artificial Sequence
<220> FEATURE:
<223> OTHER INFORMATION: 1D1 light chain AA
<220> FEATURE:
<221> NAME/KEY: CDR
<222> LOCATION: (91)..(101)
<223> OTHER INFORMATION: CDR region

<400> SEQUENCE: 15

Gln Ser Val Val Thr Gln Pro Pro Ser Val Ser Ala Ala Pro Gly Gln
1               5                   10                  15

Lys Val Thr Ile Ser Cys Ser Ala Ser Ser Ser Tyr Leu Gly Ser Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Ser Ser Gly Ile Ser Asp Arg Phe Ser
    50                  55                  60

Gly Ser Lys Ser Gly Thr Ser Ala Thr Leu Asp Ile Thr Gly Leu Gln
65                  70                  75                  80

Thr Gly Asp Glu Ala Asp Tyr Tyr Cys Gly Ala Trp Asp Ser Ser Leu
                85                  90                  95

Ser Val Val Val Phe Gly Gly Gly Thr Lys Leu Thr Val Leu
            100                 105                 110

<210> SEQ ID NO 16
<211> LENGTH: 7
<212> TYPE: PRT
<213> ORGANISM: Artificial Sequence
<220> FEATURE:
<223> OTHER INFORMATION: TEV protease site

<400> SEQUENCE: 16

Glu Asn Leu Tyr Phe Gln Gly
1               5

<210> SEQ ID NO 17
<211> LENGTH: 7
<212> TYPE: PRT
<213> ORGANISM: Artificial Sequence
<220> FEATURE:
<223> OTHER INFORMATION: TEV protease site

<400> SEQUENCE: 17

Glu Asn Leu Tyr Phe Gln Ser
1               5
```

ANTI-NMDA RECEPTOR ANTIBODIES AND METHODS OF USE

CROSS-REFERENCE TO RELATED APPLICATIONS

This is a National Stage Entry under 35 U.S.C. 371 of International Patent Application No. PCT/US2019/036185, filed Jun. 8, 2019, which claims the benefit under 35 USC § 119 (e) of U.S. Provisional Patent Application No. 62/826,552, filed Mar. 29, 2019. These applications are incorporated by reference herein.

STATEMENT REGARDING FEDERALLY SPONSORED RESEARCH OR DEVELOPMENT

This invention was made with government support under grant number R21 NS088148 awarded by the National Institutes of Health. The government has certain rights in the invention.

INCORPORATION-BY-REFERENCE OF MATERIAL SUBMITTED IN ELECTRONIC FORM

Applicant hereby incorporates by reference the Sequence Listing material filed in electronic form herewith. This file is labeled "MLH108PCT_ST25.txt", prepared Jun. 6, 2019 and is 28.0 kilobytes in size.

BACKGROUND OF THE INVENTION

Autoimmune brain encephalitis (inflammation) associated with psychiatric manifestations can be difficult to diagnose. One form of such encephalitis, Anti-N-methyl-D-aspartate Receptor Encephalitis (ANRE), is a potentially lethal autoimmune syndrome resulting from autoantibodies targeting the N-methyl-D-aspartate receptor (NMDAR) in the brain.[1] Patients with ANRE exhibit heterogeneous psychiatric and neurologic symptoms including memory loss, psychosis, hallucinations, seizures, autonomic nervous system dysfunction, and catatonia.[2,3] ANRE was originally characterized as a disease of women with ovarian teratomas[3]. However, ANRE can occur without the coexistence of teratomas.

ANRE and its symptoms have been attributed to the presence and activity of IgG antibodies that bind the GluN1 (NR1) subunit of NMDAR in the hippocampus and amygdala. ANRE antibody binding to GluN1 on cultured neurons causes receptor internalization, which is mediated by receptor cross-linking and results in decreased synaptic NMDAR levels, reduced synaptic NMDAR-mediated currents, and impairment of NMDA-dependent processes such as long-term potentiation.[4,35] ANRE IgG binding correlates with the frequency of channel opening, and acute ANRE IgG exposure prolongs the open time of the receptor, suggesting that an open channel configuration is important for pathogenic antibody binding.[6,7]

ANRE IgGs recognize the GluN1 subunit within its extracellular amino-terminal domain (ATD), which regulates NMDAR ion channel function; including channel open probability, deactivation rate, and allosteric regulation.[6,8] The ATD of NR1 is both necessary and sufficient for binding of ANRE patient antibodies[7]. The region required for GluN1 binding to ANRE IgG includes amino acids N368 and G369, which are required for post-translational modifications critical for IgG binding[7].

Current treatment of ANRE includes immunosuppressive therapies that reduce the serum and CSF titers of anti-NMDAR antibodies and surgical removal of ovarian teratomas, when present[3]. Despite aggressive measures, a quarter of patients with anti-NMDAR encephalitis remains severely impaired or die. For those who survive, recovery often takes years. However, full recovery is possible if the disease can be diagnosed and treated early in the disease course.

Detection of ANRE antibodies in the cerebrospinal fluid (CSF) is essential for diagnosis. However, diagnostic testing for anti-NR1 antibodies is technically challenging, especially for assessing anti-NMDAR IgGs in patient sera.[39,40] Pathogenic NMDAR epitopes include post-translational modifications that only occur in mammalian cells. Because over-expression of the native NMDAR can be toxic to cultured cells[7], current cell-based assays (CBA) and enzyme linked immunosorbent assays (ELISAs) for ANRE rely on cells transiently transfected with NMDAR genes[39].

SUMMARY OF THE INVENTION

In one aspect, a recombinant, synthetic or monoclonal human antibody or a fragment thereof that specifically binds to an N-methyl-D-aspartate Receptor (NMDAR) epitope is provided. The antibody or fragment comprises a heavy chain variable domain sequence encoded by a nucleic acid sequence that is at least 85% identical to SEQ ID NOs. 1, 3, or 5; or a light chain variable domain sequence encoded by a nucleic acid sequence that is at least 85% identical to SEQ ID NOs: 2, 4, or 6. Various embodiments of the NMDAR epitope-binding antibodies or fragments are disclosed.

In another aspect, a recombinant, synthetic or monoclonal human antibody or a fragment thereof that specifically binds to an N-methyl-D-aspartate Receptor (NMDAR) epitope is provided. The antibody or fragment comprises a heavy chain variable domain sequence having an amino acid sequence that is at least 85% identical to SEQ ID NOs. 10, 12, or 14; or a light chain variable domain sequence having an amino acid sequence that is at least 85% identical to SEQ ID NOs: 11, 13, or 15. Various embodiments of the NMDAR epitope-binding antibodies or fragments are disclosed.

In another aspect, a diagnostic reagent composition is provided that comprises an antibody or fragment as disclosed herein, optionally bound to a diagnostic label or immobilized on a substrate. In another aspect, a diagnostic reagent composition comprises multiple antibodies or binding fragments thereof that bind non-overlapping epitopes of NMDAR. In one embodiment, the antibodies/fragments bind different epitopes of the NMDAR amino terminal domain (ATD).

In a further aspect, a method for diagnosing encephalitis, e.g., Anti-N-methyl-D-aspartate Receptor Encephalitis (ANRE), involves contacting a biological sample from a patient with a diagnostic reagent as described herein and diagnosing ANRE by detection of a complex formed between certain NMDAR epitopes and antibodies or fragments thereof in the biological sample. In various embodiments, the method can employ the steps of a competition assay, a capture assay, a lateral flow immunoassay, or an ELISA. In yet another embodiment, a method for diagnosing encephalitis (e.g., ANRE) involves using the multi-antibody composition described herein. Still other methods requiring the use of multiple controls can utilize the antibodies described herein.

Still other aspects and advantages of these compositions and methods for making the compositions and using the compositions are described further in the following detailed description of the preferred embodiments thereof.

BRIEF DESCRIPTION OF THE DRAWINGS

FIGS. 4A and 4B show that GluN1 structural changes known to impair antigen binding by ANRE patient CSF IgGs also inhibit MAb 5F5 and 2G6 binding. HEK293T cells expressing mutant GluN1 proteins were stained with a commercial anti-GluN1 antibody (green), followed by 5F5, 2G6, or CSF (red). Nuclei were stained with DAPI. FIG. 4A shows the results using a GluN1 amino terminal deletion mutant protein. FIG. 4B shows the results using GluN1 with the N368Q mutation. Neither mutant GluN1 protein was recognized by 5F5, 2C6, or CSF. Scale bars=10 μm.

FIGS. 6A-6D are graphs showing the lack of antigen binding competition between 5F5 and 2G6 on the HEK293T-ATD cell line. 5F5 and 2G6 mAbs were each biotinylated and tested for binding to the HEK293T-ATD cell line in the presence of increasing concentrations of the other mAb, and relative luminescence values were measured (RLV). In each experiment, potential competition was measured with a value of 100% competition defined as reduction in binding seen with the homologous mAb. FIG. 6A shows 5F5-biotin binding vs. increasing 2G6. FIG. 6B shows SFS biotin vs. increasing SFS. FIG. 6C shows 2G6-biotin vs. increasing SFS. FIG. 6D shows 2G6-biotin vs. increasing 2G6.

FIG. 8A shows neurons that were cultured for 14 days and stained with ANRE CSF or mAbs (red). Top left, 5F5. Top right, 2G6. Bottom left, CSF. Bottom right, 8E1. Nuclei were stained with DAPI. Scale bar=10 μm. FIG. 8B shows neurons stained with ANRE CSF or mAbs (red), and co-stained with murine anti-GluN1 antibody (green). Rows: Top, 5F5. Middle, 2G6. Bottom, CSF. Columns: Left, GluN1. Middle, CSF or mAbs. Right, Merged images. Nuclei were stained with DAPI. Scale bar=10 μm.

FIGS. 9A-9D shows that mAb 5F5 recognizes a subset of GluN1+ puncta on neurons. FIG. 9A (top panel 200× and bottom panel 400×) show live rat hippocampal neurons at 14 population doublings stained with ANRE CSF and then with the commercial anti-GluN1 mAb (red) and an anti-PSD-95 antibody (blue), to label synapses. FIG. 9B (top panel 200× and bottom panel 400×) show live rat hippocampal neurons at 14 population doublings stained with 5F5 (green), and then with the commercial anti-GluN1 mAb (red) and an anti-PSD-95 antibody (blue), to label synapses. ANRE CSF labels almost 80% of GluN1 puncta as shown in FIG. 9A both panels and in the graph of FIG. 9C. Most puncta are colocalized with PSD-95 (blue); white in overlay (open arrow). Some ANRE CSF+/GluN1+ puncta are not colocalized with PSD-95; yellow in overlay (closed arrow). As shown in FIG. 9B (both panels and FIG. 9C, 5F5 labels less than half of the GluN1 puncta. FIG. 9D is a bar graph showing the mean labeled puncta per μm dendrite, SEM *P<0.0001, Student's t-test with Bonferroni correction. N=4 neurons, 10 dendrites, per condition. Less frequent 5F5 binding to neurons, relative to ANRE CSF, reflects different staining frequencies at synaptic sites (GluN1+/PSD-95+), rather than extrasynaptic sites (PSD-95−/GluN1+).

FIG. 10A shows staining with 5F5, 200×. FIG. 10B shows staining with 8E1, 200×. FIG. 10C shows staining with ANRE patient CSF, 200×. FIG. 10D shows staining with 5F5 on cortex, 400×. FIG. 10E shows staining with 5F5 on the pyramidal cell layer, 400×. Ctx, cortex; WM, white matter; SO, stratum oriens; Pyr, pyramidal cell layer; SR, *Stratum radiatum*.

FIG. 11A show rat hippocampal neurons incubated with 5F5, 2G6, or 6A mAbs conjugated to the CYPHER5E™ pH-sensitive fluorescent dye, which is activated by the low pH in endosomes, alone and in the presence of MK-801 or AP5. FIG. 11B shows neurons treated with MK-801 or AP5 assessed for binding of the 5F5, 2G6, or 6A mAbs. Scale bar=5 μm.

FIGS. 12A-12B show alterations in voluntary running activity induced by 5F5 and 2G6 mAbs. FIG. 12A is a bar graph showing that voluntary running activity was measured in mice before and after receiving 5F5, 2G6, or both mAbs. Prior to mAb administration, the mice received a dose of LPS to open the blood brain barrier. Baseline levels were recorded for 4 days prior to LPS/mAb administration and compared to the 4 day steady state period following recovery from LPS toxicity. The differences in the average number of daily wheel revolutions are shown. One-way ANOVA *P=0.026, P=0.033, *P=0.0005. FIG> 12B is a bar graph showing that voluntary running activity was measured in mice before and after receiving MK-801 (100 μg/kg or 50 μg/kg). Baseline levels were recorded for 4 days prior to MK-801 injection and compared to the 4 days following the injection. The differences in the average numbers of daily wheel revolutions are shown. One-way ANOVA *P=0.0001, **P=0.0001. Error bars indicate S.E.M.

FIG. 16A is a graph showing the results of a whole cell competitive assay comparing mAb 1D1 vs. 5F5 and 2G6.

FIG. 16B is a graph showing the results of a whole cell competitive assay comparing mAb 2G6 vs. 2G6 and biotinylated 1D1.

FIGS. 22A and 22B show mobilization of membrane-bound ATD with TEV protease. 293T-ATD cells were washed and then treated with TEV protease for 10, 20, 30, or 40 min FIG. 22A shows the expressed and mobilized ATD analyzed by capture ELISA. FIG. 22B shows the ATD analyzed by Coomassie-stained SDS:PAGE. Abbreviations include: ATD, amino-terminal domain; Control, medium-only blank; M, marker; RLV, relative luminescence value. Bars indicate the S.E.M.

FIGS. 23A and 23B show binding of human anti-NR1 mAbs to plate-adherent ATD. ATD mobilized by TEV protease treatment of 293T-ATD cells was captured by a Myc tag antibody and tested for binding by commercial and human mAbs. FIG. 23A used murine anti-NR1 mAb. FIG. 23B used human mAbs, 5F5, 2G6, 1D1, and 6A (isotype control). All samples were tested in triplicate. RLV, relative luminescence value; Ctrl, buffer only. Bars indicate the S.E.M.

DETAILED DESCRIPTION

Figure 1:
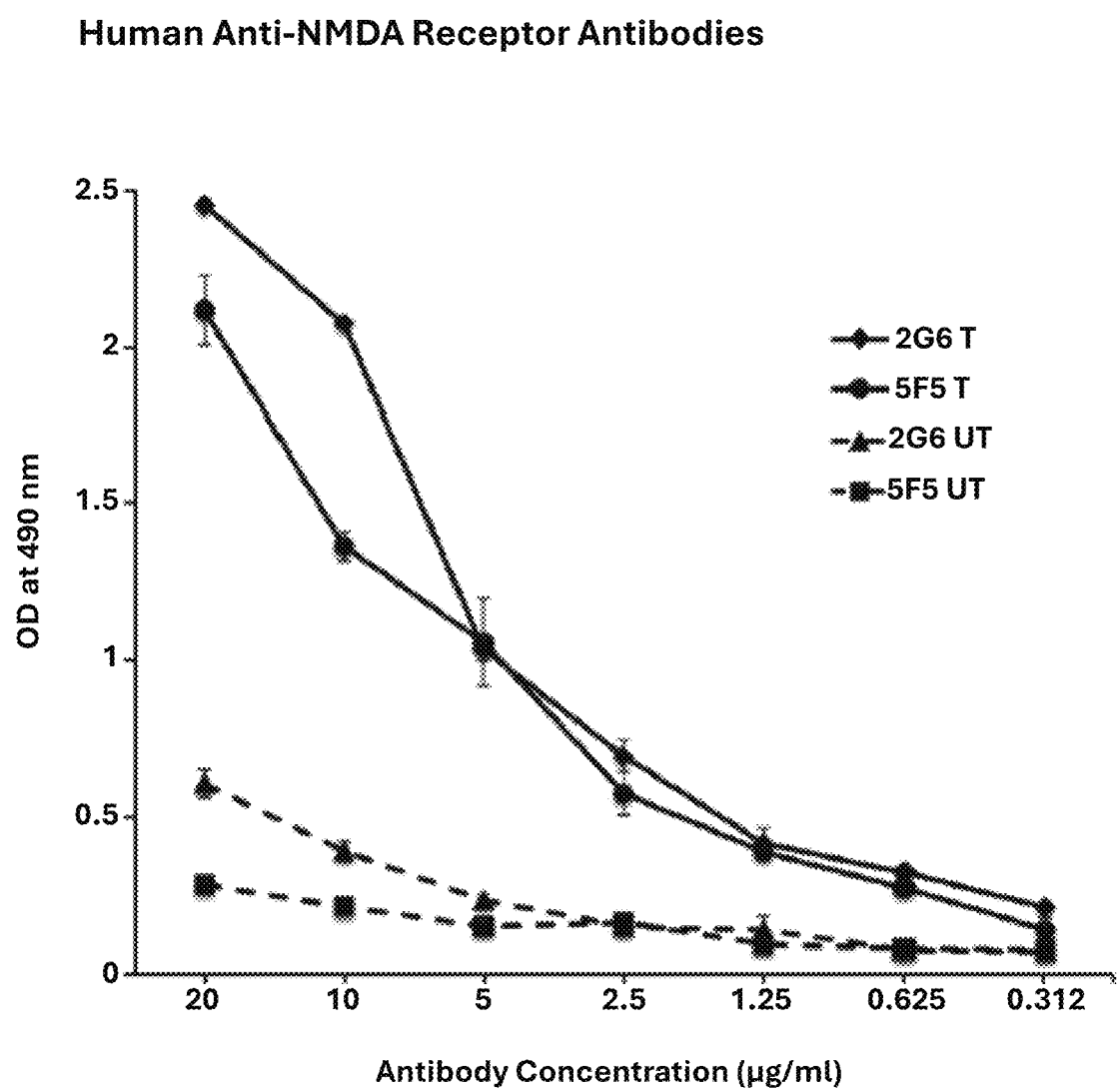
FIG. 1 is a graph showing that monoclonal IgG antibodies 2G6 and 5F5 from ANRE patients bind HEK 293T cells expressing GluN1/2a. Triplicate serial dilutions of the 5F5 and 2G6 mAbs were assessed for binding to HEK293T cells transfected with GluN1a and GluN2a expression plasmids (T) or untransfected (UT) in a whole cell lysate ELISA. Both 5F5 and 2G6 bind preferentially to GluN1/GluN2a expressing cells. OD, optical density.

Diagnostic compositions and methods are disclosed herein that facilitate diagnosis of autoimmune encephalitis.

In a specific embodiment, these methods and diagnostic compositions can support a diagnosis of Anti-N-methyl-D-aspartate Receptor Encephalitis (ANRE) in patients. In certain embodiments, the patients present with psychiatric symptoms.

Without wishing to be bound by theory, the inventors theorized that the varied clinical manifestations of ANRE could be explained by differences in antibody-antigen/epitope binding specificity and regulatory effects, and that monoclonal antibodies isolated from ANRE patients would replicate these features. The inventors have developed monoclonal and recombinant antibodies from B cells isolated from peripheral blood of an ANRE-patient. These antibodies replicate many of the features predicted from the studies of polyclonal CSF IgGs.[9] These new antibodies bind NMDAR on hippocampal neurons in patterns that partly overlap with GluN1 and require the presence of N368 for binding. Furthermore, they downregulate NMDAR from the neuronal membrane.

Using the nucleic acid sequences of the heavy chain and light chain variable regions of the monoclonal antibodies, a variety of NMDAR-binding antibodies and fragments thereof are generated for use in diagnosis of ANRE.

Components Utilized in the Compositions and Methods

In one embodiment, an "antibody" refers to an intact immunoglobulin, such as an IgG, or to an antigen binding portion thereof that competes with the intact antibody for specific binding, unless otherwise specified. In one embodiment, an intact antibody is an IgG1, IgG2, IgG3 or IgG4. An antibody (e.g., an antibody, an antibody heavy chain, an antibody light chain, or any fragment or modification thereof) comprises three Complementarity-Determining Regions (CDRs, also known as HV, hypervariable regions, namely CDR1, CDR2, CDR3, from N-terminal to C-terminal, or 5' to 3' when corresponding nucleic acid sequence is referred to), and four framework regions (FRs, namely FR1, FR2, FR3 and FR4, from N-terminal to C-terminal, or 5' to 3' when corresponding nucleic acid sequence is referred to). See, e.g., Janeway, Charles A Jr; Travers, Paul; Walport, Mark; Shlomchik, Mark J (2001). Immunobiology: The Immune System in Health and Disease (5 ed.). New York: Garland Science. ISBN 0-8153-3642-X, which is incorporated herein by its entirety. It would be understood that in the antibody construct, CDRs are arranged non-consecutively, not immediately adjacent to each other, and may be separated by an FR. As part of the variable chain in an antibody construct and T cell receptors generated by B-cells and T-cells respectively, CDRs are where an antigen specifically binds.

The antibody or fragment includes a monoclonal antibody, such as the 5F5, 2G6 and 1D1 antibodies which were the sources of the heavy chain and light chain variable domain coding sequences SEQ ID NO: 1-6. Such antibodies can also include a synthetic antibody, a recombinant antibody, a chimeric antibody, a humanized antibody, a human antibody, a CDR-grafted antibody, a multispecific binding construct that can bind two or more epitopes, a dual specific antibody, a bi-specific antibody, a multi-specific antibody, an affinity matured antibody, a single antibody chain or an scFv fragment, a diabody, a single chain comprising complementary scFvs (tandem scFvs) or bispecific tandem scFvs, an Fv construct, a disulfide-linked Fv, a Fab construct, a Fab' construct, a F(ab')2 construct, an Fc construct, a monovalent or bivalent construct from which domains non-essential to monoclonal antibody function have been removed, a single-chain molecule containing one VL (variable region of light chain), one VH (variable region of heavy chain) antigen-binding domain, and one or two constant "effector" domains optionally connected by linker domains, a univalent antibody lacking a hinge region, a single domain antibody, a dual variable domain immunoglobulin (DVD-Ig) binding protein or a nanobody, or any recombinant versions thereof. Definitions and examples of these types of structures are found in the art and in, e.g., U.S. Pat. No. 9,902,772, incorporated by reference herein.

The term "recombinant antibody" refers to an antibody that is generated by cloning the immune-specific heavy and light antibody coding sequences into a vector. In one embodiment, the vector is designed for high-yield mammalian expression. The resulting vectors are introduced into expression hosts (e.g., bacteria, virus, yeast or mammalian) for the manufacturing of high-quality functional antibodies. Generally, the coding sequence is not naturally associated with the host cell. Recombinant antibodies have glycosylation patterns that differ from the glycosylation pattern of an antibody having the same sequence if it were to exist in nature. In one embodiment, a recombinant antibody is expressed in a mammalian host cell which is not a human host cell. Notably, individual mammalian host cells have unique glycosylation patterns. Recombinant antibodies can be constructed in vitro by forming an Ig-framework through cloning of scFV or Fab or can be produced from an existing hybridoma. In hybridoma-based recombinant antibody generation, mouse, rat, and rabbit models are commonly used. However, as long as the appropriate oligonucleotide primers are available, recombinant antibodies can be developed from any species.

As used herein, an "antibody mimic" or an "antibody equivalent" refers to affibodies, i.e., a class of engineered affinity proteins, generally small (~6.5 kDa) single domain proteins that can be isolated for high affinity and specificity to any given target, aptamers, polypeptide molecules that bind to a specific target, an affilin, an affitin, an affimer, an alphabody, an anticalin, an avimer, a DARPin (designed ankyrin repeat proteins), a Fynomer, a Kunitz domain peptide, a monobody, a peptabody and others known in the art.

Unless otherwise indicated, the term "anti-NMDAR antibody" as used herein, includes, the monoclonal IgG immunoglobulins 5G5, 2G6 and 1D1, comprising two full-length heavy chains (each chain comprising a variable region and a constant region) and two full-length light chains (each chain comprising a variable region and a constant region), as well as modifications, antigen/epitope binding fragments, as well as "antibody mimics" or "antibody equivalents" or constructs of fragments encoded by one or more of SEQ ID Nos: 1-6. In one embodiment, the antibody or epitope binding fragments as described herein refers to an anti-NMDAR antibody or fragment encoded by a nucleic acid sequences at least 85% identical to one of SEQ ID NO: 1, 3, and 5. In another embodiment, the antibody or epitope binding fragments as described herein refers to an anti-NMDAR antibody or fragment encoded by nucleic acid sequences at least 85% identical to SEQ ID NO: 2, 4 and 6.

In another embodiment, the "anti-NMDAR antibody" as used herein, includes, the monoclonal IgG immunoglobulins 5G5, 2G6 and 1D1, comprising two full-length heavy chains (each chain comprising a variable region and a constant region) and two full-length light chains (each chain comprising a variable region and a constant region), as well as modifications, antigen/epitope binding fragments, as well as antibody mimics" or "antibody equivalents" or constructs of fragments comprising at least one amino acid sequence of SEQ ID NO: 10-15. In one embodiment, the antibody or epitope binding fragments as described herein refers to an anti-NMDAR antibody or fragment having a heavy chain amino acid sequences at least 85% identical to one of SEQ ID NO: 10, 12, and 14. In another embodiment, the antibody or epitope binding fragments as described herein refers to an anti-NMDAR antibody or fragment having a light chain amino acid sequence at least 85% identical to one of SEQ ID NO: 11, 13 and 15. By "at least 85% identical" encompasses at least 86%, 87%, 88%, 89%, 90%, 91%, 92%, 93%, 94%, 95%, 96%, 97%, 98%, 99%, up to 100% sequence identity with the identified reference SEQ ID NO.

As used herein, a "modification" of an antibody refers to an antibody heavy chain or light chain amino acid sequence, in which wherein one or more amino acid residues are inserted into, deleted from, and/or substituted into the reference amino acid sequence, e.g., any of amino acid sequence encoding the variable light or heavy chains, and/or CDRs of antibodies 5F5, 2G6 or 1D1. One such modification is the replacement of one amino acid in such a sequence, e.g., any of amino acid sequences encoded by SEQ ID NO: 1 to 6, or amino acid sequences of 10 to 15, with a conservative amino acid. Other modifications include, for example, fusion proteins formed by fusing the heavy chain of a selected antibody into an Ig backbone. Still another modification includes an anti-NMDAR antibody that has been modified via conjugation to another chemical moiety (such as, for example, polyethylene glycol or albumin, e.g., human serum albumin), phosphorylation, and glycosylation. In another embodiment, a modification of any of antibodies 5F5, 2G6 or 1D1 is a single chain human antibody, having a variable domain region from a heavy chain and a variable domain region from a light chain and a peptide linker connecting the heavy chain and light chain variable domain regions.

Other modifications include V(D)J recombination/rearrangement, e.g., a process by which T cells and B cells randomly assemble different gene segments—known as variable (V), diversity (D) and joining (J) genes (or regions, or segments, as used herein)—in order to generate unique receptors (known as antigen receptors) that can collectively recognize many different types of antigens. Briefly, the germ line (unrearranged) genomic DNA configuration of the immunoglobulin heavy chain locus comprises the tandem arrays of V, D, and J gene segments. A germ line kappa or lambda light chain locus comprises unrearranged V and J segments. Stepwise rearrangement of the germ line DNA results in the joining of a heavy chain D and J gene segment, followed by joining of a V segment to the D-J product, to generate the DNA encoding the heavy chain variable region. In the process of rearrangement, the ends of the gene segments are subject to variable amounts of exonuclease digestion and randomized non-templated bases are added at the segment ends, to produce additional sequence diversity at the VDJ junctional region that encodes the complementarity-determining region 3 (CDR3), which is often the region of the antibody heavy chain that has the greatest impact on antigen specificity. A similar process of V and J gene rearrangement with diversification of the VJ junction occurs in the light chain locus, to produce the rearranged light chain gene. See, e.g., Boyd et al, High-Throughput DNA Sequencing Analysis of Antibody Repertoires Microbiology Spectrum. 2. 10.1128/microbiolspec.AID-0017-2014, which is incorporated herein by its entirety.

Methods for producing such antibodies and antibody fragments are well-known in the art. Indeed, commercial vectors for certain antibody and antibody fragment constructs are available. The antibody may also be a protein (e.g., a fusion protein) comprising at least one antibody or antibody fragment. In a particular embodiment, the antibody comprises an Fc region.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. An epitope typically includes at least 3, and more usually, at least 5 or 8-10 amino acids in a unique spatial conformation. An antigenic determinant can compete with the intact antigen (i.e., the "immunogen" used to elicit the immune response) for binding to an antibody. The term "NMDAR epitope" as used herein refers to the portion of an NMDAR protein or any naturally occurring or synthetic or recombinant amino acid sequence that is capable of specifically complexing with one or more of the antibodies 5F5, 2G6 or 1D1, or epitope binding fragments or modified antibodies encoded by one or more of SEQ ID NOs: 1 to 6, or by sequences at least 85% identical to SEQ ID NOs: 1-6, or having an amino acid sequence at least 85% identical to one of more of SEQ ID Nos: 10-15, as described herein. In one embodiment, the epitope is within the first 561 amino acids of the amino terminal domain (ATD) of NR1 SEQ ID NO: 7. As noted in the examples shown in FIGS. 6A-6D, 15A, 15B, 16A and 16B, each of the mAbs described herein (5F5, 2G6, and 1D1) bind distinct, non-overlapping epitopes on the NMDAR ATD. It is further established that the 5F5 and 2G6 mAbs bind an epitope that depends on the presence amino acid N368, which mediates post-translational modification required for ANRE patient-derived anti-NMDAR antibodies.

As used herein, the term "immunologically specific" refers to antibodies, that bind to one or more epitopes of a protein or compound of interest, but which do not substantially recognize and bind other molecules in a sample containing a mixed population of antigenic biological molecules.

An antibody, fragment or modification described herein may have a binding affinity and/or immunological specificity to its epitope at about 20%, about 40%, about 50%, about 60%, about 70%, about 80%, about 90%, about 95%, about 97%, about 99%, about 100%, more than about 100%, about 200%, about 300%, or about 500% of that of any known anti NMDAR-antibody. Conventional methods, including enzyme-linked immunosorbent assay (ELISA), radioimmunoassay (RIA), MSD assay, and antibody phage display library, may be used to determine such binding affinity and/or specificity. In certain embodiments, these anti-NMDAR antibodies and fragments have a binding affinity (Ka) for an NMDAR epitope that is sufficient to mediate binding on cultured cells and receptor internalization. In one embodiment, such Ka is between 0.1 to 1.5M.

The term "isolated" designates a biological material (nucleic acid or protein) that has been removed from its original environment (the environment in which it is naturally present). For example, a polynucleotide present in its natural state in a plant or an animal is not isolated, however the same polynucleotide separated from the adjacent nucleic acids in which it is naturally present, is considered "isolated". The term "purified" does not require the material to be present in a form exhibiting absolute purity, exclusive of the presence of other compounds.

The terms "percent (%) identity", "sequence identity", "percent sequence identity", or "percent identical" in the context of amino acid sequences or nucleotide sequences refers to the residues in the two sequences which are the same when aligned for correspondence. Percent identity may be readily determined for amino acid sequences or nucleotide sequences over the full-length of a protein, polypeptide, or encoding region thereof, e.g., about 15 amino acids, about 150 amino acids, or a peptide fragment thereof or the corresponding nucleic acid sequence coding sequences. A suitable amino acid fragment may be at least about 4 amino acids in length and may be up to about 200 or up to about 700 amino acids or nucleotide fragments of from about 12 nucleotides to about 600 to 2100 nucleotides. Generally, when referring to "identity", "homology", or "similarity" between two different sequences, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence. Alignments are performed using any of a variety of publicly or commercially available Multiple Sequence Alignment Programs. Sequence alignment programs are available for amino acid sequences, e.g., the "Clustal Omega", "Clustal X", "MAP", "PIMA", "MSA", "BLOCK-MAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., (THOMPSON et al. 1999).

As used herein, "disease", "disorder" and "condition" are used interchangeably, to indicate an abnormal state in a subject. In one embodiment, the disease is an autoimmune encephalitis. In another embodiment, the disease is ANRE.

"Patient" or "subject" as used herein refer to a mammal, particularly, a human. The patient may have mild, intermediate or severe disease or symptoms of disease. The patient may be treatment naive, responding to any form of treatment, or refractory. The patient may be an individual in need of treatment or in need of diagnosis based on particular symptoms or family history. In one embodiment, the subject of these methods and compositions is a human exhibiting psychiatric symptoms characteristic of, or believed to be suggestive of, ANRE. In some cases, the terms may refer to treatment or diagnosis in experimental animals, in veterinary application, and in the development of animal models for disease, including, but not limited to, rodents including mice, rats, and hamsters; and primates, a veterinary or farm animal, a domestic animal or pet, and animals normally used for clinical research.

The terms "sample," "patient sample," "biological sample," and the like, encompass a variety of sample types obtained from a patient, individual, or subject and can be used in a diagnostic or monitoring assay. The patient sample may be obtained from a healthy subject, a diseased patient or a patient having associated symptoms of encephalitis or ANRE. Moreover, a sample obtained from a patient can be divided and only a portion may be used for diagnosis. Further, the sample, or a portion thereof, can be stored under conditions to maintain sample for later analysis. The definition specifically encompasses blood and other liquid samples of biological origin (including, but not limited to, plasma, serum, peripheral blood, cerebrospinal fluid, urine, saliva, stool and synovial fluid), solid tissue samples such as a biopsy specimen or tissue cultures or cells derived therefrom and the progeny thereof. In a specific embodiment, a sample comprises a blood sample or a cerebrospinal fluid sample. In another embodiment, a serum or plasma sample is used. The definition also includes samples that have been manipulated in any way after their procurement, such as by centrifugation, filtration, precipitation, dialysis, chromatography, treatment with reagents, washing, or enriched for certain cell populations. The terms further encompass a clinical sample, and also include cells in culture, cell supernatants, tissue samples, organs, and the like. Samples may also comprise fresh-frozen and/or formalin-fixed, paraffin-embedded tissue blocks, such as blocks prepared from clinical or pathological biopsies, prepared for pathological analysis or study by immunohistochemistry.

As used herein, the term "comparing" refers to making an assessment of how the proportion, level or cellular localization of an antibody reactive with an NMDAR epitope or antigen in a sample from a patient relates to the proportion, level or cellular localization of the corresponding antibody in a standard or control sample. More specifically, the term may refer to assessing whether the proportion, level, or cellular localization of the NMDAR-reactive antibody in a sample from a patient is the same as, more or less than, different from or otherwise corresponds (or not) to the proportion, level, type, or cellular localization of predefined levels that correspond to, for example, a patient having subclinical encephalitis or ANRE, or a subject not having autoimmune encephalitis, or a patient not having ANRE, or a patient that is responding to treatment for ANRE, or a patient that is not responding to treatment for ANRE, or a patient that is/is not likely to respond to a particular ANRE treatment, or a patient having/not having another disease or condition. For the purposes of calibrating these levels, the 5F5, 2G6, and 1D1 antibodies are suitable as positive controls (for use as standards) because they replicate fundamental features of pathogenic anti-NMDAR antibodies.

As used herein, the terms "indicates" or "correlates" (or "indicating" or "correlating," or "indication" or "correlation," depending on the context) in reference to the level or cellular localization of an antibody reactive with an NMDAR epitope or antigen in a sample from a patient, may mean that the patient has ANRE. A particular level or amount of an antibody reactive with an NMDAR epitope or antigen detected by binding to an NMDAR polypeptide or fragment described herein may indicate that a patient has ANRE (i.e., correlates to a patient having ANRE). In other embodiments, a low or unmeasurable level or amount of the NMDAR-reactive antibody detected by binding to an NMDAR epitope, antigen or fragment described herein indicates that a patient does not have ANRE. In certain embodiments, "indicating," or "correlating," as used herein, may be by any linear or non-linear method of quantifying the relationship between the level or amount of NMDAR-reactive antibody detected by binding to an NMDAR epitope, antigen or fragment described herein, in comparison to a standard, control or comparative value for the assessment of the diagnosis, as may be established by the use of the 5F5, 2G6, and/or 1D1 monoclonal antibodies described herein, as well as prediction of ANRE or ANRE progression, assessment of efficacy of clinical treatment, identification of a patient that may respond to a particular treatment regime or pharmaceutical agent, monitoring of the progress of treatment, and in the context of a screening assay, for the identification of a subject likely to benefit from an anti-ANRE therapeutic or medical treatment.

The terms "measuring" and "determining" are used interchangeably throughout and refer to methods which include obtaining a patient sample and/or detecting the level of an antibody reactive with an NMDAR epitope or antigen detected by binding to an NMDAR polypeptide or fragment as described herein. In one embodiment, the terms refer to obtaining a patient sample and detecting the level of the NMDAR-reactive antibody in the sample. Measuring can be accomplished by methods known in the art and those further described herein. The term "measuring" is also used interchangeably throughout with the term "detecting."

A "suitable control," "appropriate control" or a "control sample" is any control or standard familiar to one of ordinary skill in the art useful for comparison purposes. In one embodiment, a "suitable control" is a value, level, feature, characteristic, property, (e.g., that of the presence or amount of NMDAR-reactive antibody similar to the antibodies described herein), that is determined in a healthy or unaffected patient. Other suitable controls include the same levels, etc., in a patient with early stage ANRE, or in a patient with late stage ANRE, or in a patient or the same patient being treated for ANRE, or in a patient with an encephalitis other than ANRE.

While various embodiments in the specification are presented using "comprising" language, under various circumstances, a related embodiment is also described using "consisting of" or "consisting essentially of" language. "Comprising" is a term meaning inclusive of other components or method steps. When "comprising" is used, it is to be understood that related embodiments include descriptions using the "consisting of" terminology, which excludes other components or method steps, and "consisting essentially of" terminology, which excludes any components or method steps that substantially change the nature of the embodiment or invention.

The terms "a" or "an" refers to one or more. For example, "an expression cassette" is understood to represent one or more such cassettes. As such, the terms "a" (or "an"), "one or more," and "at least one" are used interchangeably herein.

As used herein, the term "about" means a variability of plus or minus 10% from the reference given, unless otherwise specified.

As used herein, the term "increase" "decrease" "elevation" "change" or any variation thereof means a variability of plus or minus 10, 20, 30, 40, 50, 60, 70, 80, 90 or 95% from the reference given, unless otherwise specified.

Technical and scientific terms used herein have the same meaning as commonly understood by one of ordinary skill in the art to which this invention belongs and by reference to published texts, which provide one skilled in the art with a general guide to many of the terms used in the present application. The definitions contained in this specification are provided for clarity in describing the components and compositions herein and are not intended to limit the claimed invention.

Specific Anti-NMDAR Antibodies, Fragments and Methods of Producing Antibodies

As described in detail in the Examples below, using a hybridoma method, the inventors cloned and characterized three monoclonal antibodies (mAbs) from an ANRE patient. The three mAbs are identified as 5F5, 2G6 and 1D1. The nucleic acid sequences encoding the variable heavy and light chains of antibodies 5F5, 2G6 and 1D1 are shown below in Table 1 below. In certain embodiments, variable heavy or light chain refers to variable region of a heavy or light immunoglobulin chain.

TABLE 1

| | mAb 5F5 Nucleic Acid Sequences | |
|---|---|---|
| Variable Heavy Chain | CAGGTGCAGCTGGTGGAGTCTGGAGGAGGCGTGGTCCGG CCTGGGGGGTCCCTGAGACTCTCTTGTGCAGCCTCTGGA TTCACCTTCAGTACCTATAGTCTTCACTGGGTCCGCCAG GCTCCAGGCAAGGGGCTGGAGTGGGTTGGAGTTATTTTA TATGATGGCAGCAAAAAATATTATGCAGACTCCGTGAGG GGCCGATTCACCATCTCCAGAGACAATTCCAAGAGCACG CTAAATCTGGATATGAGCAGCCTGAGACCTGACGACACG GCTGTGTATTACTGTGCGAGAGACCCAATAGCAGTGGCT CCCAGGCCCAGCGGCATGGTCCCCCAGGGATTTGACTAT TGGGGCCAGGGAACCCTGGTCACCGTCTCCTCAG | SEQ ID NO: 1 |
| Variable Light Chain | CAGTCTGTCGTGACGCAGCCGCCCTCAGCGTCTGGGACC CCCGGGCAGAGGGTCACCATCTCCTGTTCTGGAAGCAGC TCCAACATCGGAAGAAATTTTGTATTCTGGTATCGGCAG CTCCCAGGAACGGCCCCCAAAGTCCTCATCTATAAGAAT ATTCAGCGGCCCTCAGGGGTCCCTGACCGAATCTCTGGC TCCAGGTCTGGCTCCTCAGCCTCCCTGGCCATCAGTGGA CTCCGGTCCGAGGATGAGGCTGATTATTACTGTGCATCA TGGGATGACAGCCTGAGTGGTGTGGTGTTCGGCGGGGGG ACCAAGCTGACCGTCCTAA | SEQ ID NO: 2 |
| | mAb 2G6 Nucleic Acid Sequences | |
| Variable Heavy Chain | CAGGTGCAGCTGCAGGAGTCGGGGGGAGGCGTGGTCCAG CCTGGGAGGTCCCTGAGACTCTCCTGTGCAGCCTCTGGG TTCAGCTTCAATGCCTTTGCCATGCACTGGGTCCGCCAG GCTCCAGGCAAGGGGCTGGAGTGGGTGGCACGCATATCA CATTATGGAAGTGATGACTACTATGCAGACTCTGTGAAG GGCCGATTCACCATCTCCAGAGACAATTCCCAGAACACT CTGTTTCTGCAAATGAACAGCCTGAAAGCCGAGGACACG GGTGTGTATTACTGTTGGAGGGGATTTACTCTGGTTCGG GGAGTTATTTCGAGAAATCCCATTAATCGATTCTCCGGT ATGGACGTCTGGGGCCAAGGGACCACGGTCACCGTCTCT TC | SEQ ID NO: 3 |

TABLE 1-continued

| | | |
|---|---|---|
| Variable Light Chain | TCCTATGAGCTGATGCAGCCACCCTCGGTGTCAGTGTCC CCAGGACAAACGGCCAGGATCACCTGCTCTGGAGATGCA TTGCCAAAAAAATATGCTTATTGGTACCAGCAGAAGTCA GGCCAGGCCCCTATACTGGTCATCTATGAGGACAACAAA CGACCCTCCGGGATCCCTGAGAGATTCTCTGGCTCCAGC TCAGGGACAATGGCCACCTTGACTATCAGTGGGCCCAG GTGGAGGATGAAGCTGACTACTTCTGTTATTCAACAGAC AGCAGTGGTAATCATGGGGTATTCGGCGGAGGGACCAAG CTGACCGTCCTAA | SEQ ID NO: 4 |
| mAb 1D1 Nucleic Acid Sequences | | |
| Variable Heavy Chain | TTGGTGCAGCTGGTGGAGTCCGGGGGAGGCGTGGTCCAG TCTGGGAGGTCCCTGAGACTCTCCTGTGCAGCCTCTGGA TTCGCCTTCCATACCTTTACTATACACTGGGTCCGCCAG GCTCCAGGCAAGGGGCTGGACTGGGTAACAGCTATATAT TTTGATGGAACCAAAAAATACTACGCAGACTCCGTGAAG GGCCGATTCACCGTCTCCAGAGACAACTCCAAGAACACG GTATATCTGCAAATGAACGGCCTGAGAGGTGAGGACACG GCTGTCTATTACTGTGCGAGAGCCCGATACAGCTATGGC CTTTCCTTTGACTACTGGGGCCAGGGAACCCCGGTCACC GTCTCCTCTG | SEQ ID NO: 5 |
| Variable Light Chain | CAGTCTGTCGTGACGCAGCCGCCCTCAGTGTCTGCGGCCC CAGGACAGAAGGTCACCATCTCCTGCTCTGCAAGCAGCTC CTACCTTGGGAGTAATTATGTATCTTGGTACCAGCAACTC CCAGGAACAGCCCCCAAACTCCTCATTTATGACAATAATA AGCGATCCTCAGGGATTTCTGACCGATTCTCTGGCTCCAA GTCTGGCACGTCAGCCACCCTGGACATCACCGGCCTGCAG ACTGGGGACGAGGCCGACTATTACTGCGGAGCATGGGACA GCAGCCTGAGTGTCGTGGTTTTCGGCGGAGGGACCAAGCT GACCGTCCTAA | SEQ ID NO: 6 |

The amino acid sequences of the variable heavy and light chains of antibodies 5F5, 2G6 and 1D1 are shown below in Table 2 below, with their respective complementarity-determining region (CDR) regions highlighted in bold print.

TABLE 2

| | | |
|---|---|---|
| mAb 5F5 Amino Acid Sequences | | |
| Variable Heavy Chain | QVQLVESGGGVVRPGGSLRLSCAASGFTFSTYSLHWVRQ APGKGLEWVGVILYDGSKKYYADSVRGRFTISRDNSKST LNLDMSSLRPDDTAVYYCARDPIAVAPRPSGMVPQGEDY WGQGTLVTVSS | SEQ ID NO: 10 |
| Variable Light Chain | QSVVTQPPSASGTPGQRVTISCSGSSSNIGRNFVFWYRQ LPGTAPKVLIYKNIQRPSGVPDRISGSRSGSSASLAISG LRSEDEADYYCASWDDSLSGVVFGGGTKLTVL | SEQ ID NO: 11 |
| mAb 2G6 Amino Acid Sequences | | |
| Variable Heavy Chain | QVQLQESGGGVVQPGRSLRLSCAASGFSFNAFAMHWVRQ APGKGLEWVARISHYGSDDYYADSVKGRFTISRDNSQNT LFLQMNSLKAEDTGVYYCWRGFTLVRGVISRNPINRFSG MDVWGQGTTVTVS | SEQ ID NO: 12 |
| Variable Light Chain | SYELMQPPSVSVSPGQTARITCSGD-ALPKKYAYWYQQK SGQAPILVIYEDNKRPSGIPERFSGSSSGTMATLTISGA QVEDEADYFCYSTDSSGNHGVFGGGTKLTVL | SEQ ID NO: 13 |
| mAb 1D1 Amino Acid Sequences | | |
| Variable Heavy Chain | LVQLVESGGGVVQSGRSLRLSCAASGFAFHTFTIHWVR QAPGKGLDWVTAIYFDGTKKYYADSVKGRFTVSRDNSK NTVYLQMNGLRGEDTAVYYCARARYSYGLSFDYWGQGT PVTVSS | SEQ ID NO: 14 |
| Variable Light Chain | QSVVTQPPSVSAAPGQKVTISCSASSSYLGSNYVSWYQ QLPGTAPKLLIYDNNKRSSGISDRESGSKSGTSATLDI TGLQTGDEADYYCGAWDSSLSVVVFGGGTKLTVL | SEQ ID NO: 15 |

In certain embodiments, a CDR of any one of SEQ ID NOs: 10-15 is the one shown in Table 2 truncated with 1, 2, or 3 amino acids in the N terminal and/or the C terminal. In certain embodiments, a CDR of any one of SEQ ID NOs: 10-15 is the one shown in Table 2 shifted to the N terminal side or the C terminal side by 1, 2, or 3 amino acids. In certain embodiments, provided herein is an antibody, or a variant thereof, or an epitope binding fragment thereof comprising 1, 2, 3, 4, 5, or 6 CDR(s) as described. As used herein, the complementarity-determining region (CDR) refers to part of the variable chains in antibodies or T cell receptors, which binds to the corresponding epitope. Such CDR may be determined via experiments or via various predicating tools, such as www.imgt.org/IMGT_vquest/ analysis. Also provided herein is a nucleic acid sequence encoding an antibody, or a variant thereof, or an epitope binding fragment thereof as described herein. As used herein, an epitope binding fragment refers to a fragment of an antibody which is determined to be bound to an epitope. Such determination may be performed experimentally using for example ELISA or other methods discussed herein or via various predicating tools such as IMGT.org.

The antigen binding and functional features were analyzed in vitro and in vivo. These IgG mAbs were developed from a female patient with ANRE without an associated teratoma. Their binding activities on NMDAR-transfected cell lines, cultured primary rat neurons, and mouse hippocampus, and their effects on voluntary locomotor activity in mice and binding to NMDAR in vivo were assessed as described in Examples 1-6 below.

Figure 7A:
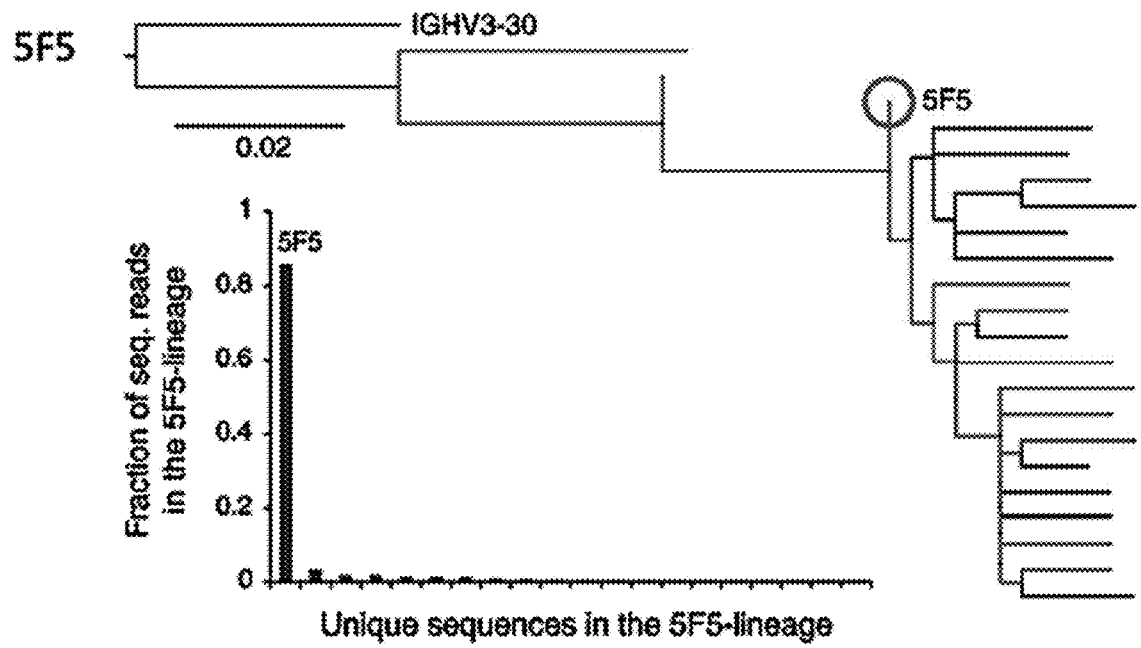
FIGS. 7A and 7B are phylogenetic analyses of the 5F5 and 2G6 mAb lineages, respectively. The patient's peripheral blood B-cell population was sampled, after in vitro proliferation and prior to cell fusion, and analyzed by Ig heavy chain sequencing. Lineages were defined to include sequences with >80% nucleotide sequence homology in CDRH3 domain and were analyzed by Clustal sequence analysis. Sequences with identical CDRH3 domains are shown as dotted lines. Below each dendrogram is plotted the fraction of total sequencing reads for each lineage member.
Figure 7B:
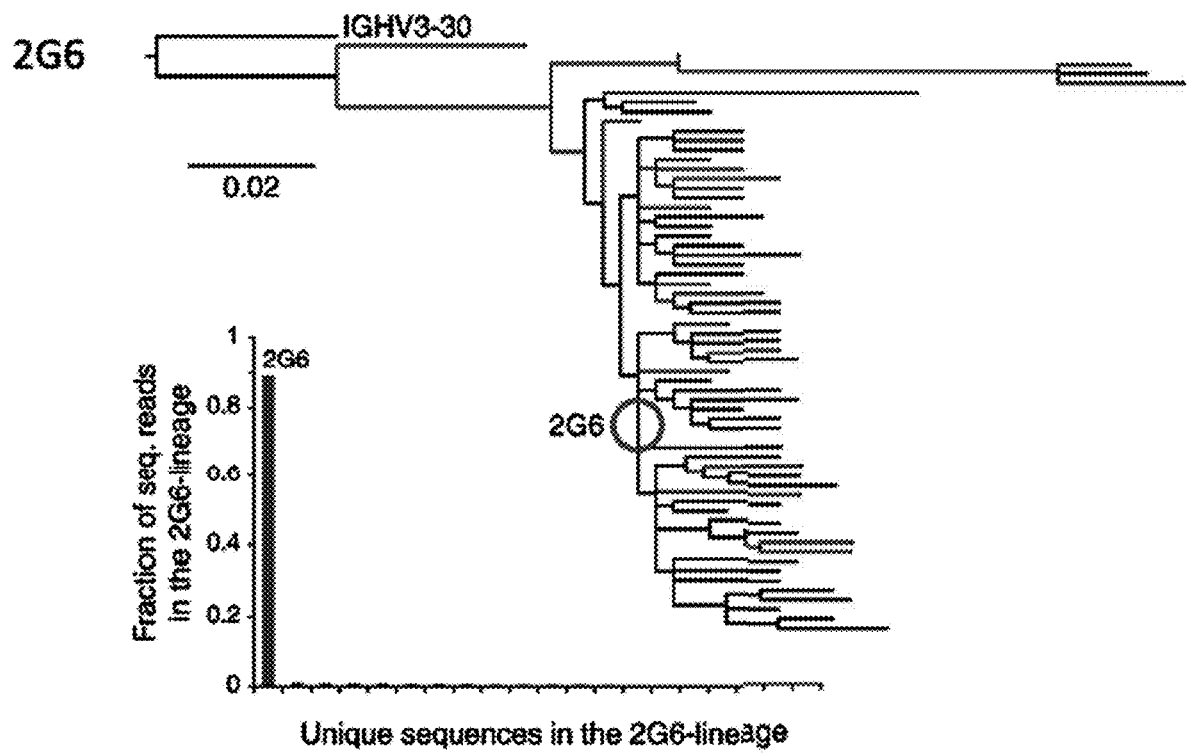

Two of the mAbs, 5F5 and 2G6, are structurally distinct and arose from distinct B-cell lineages (see FIG. 7). These mAbs recapitulate features demonstrated in previous studies of ANRE patient CSF and exert effects on NMDAR in vitro and in vivo consistent with modulation of NMDAR activity. They recognize and bind different non-competing epitopes on the GluN1 amino terminal domain (ATD). They bind specifically to GluN1 in transfected cells and on cultured hippocampal neurons, but only a subset of the synaptic hippocampal GluN1 is recognized by the mAbs. They require amino acids important for post-translational modification. The IgG monoclonal antibodies 5F5 and 2G6 bind GluN1 expressed in HEK293T cells, as well as an isolated NMDAR 561 amino terminal domain (ATD) SEQ ID NO: 7, and they require the GluN1 N368, a site of post-translational modification required for ANRE patient IgG binding. In certain embodiments, the IgG monoclonal antibodies 5F5 and 2G6 bind to the open state/configuration of the NMDAR GluN1 subunit, instead of the closed configuration.

Each mAb binds a subset of GluN1 on cultured rat hippocampal neurons. The 5F5 mAb binds mouse brain hippocampal tissues, and the GluN1 recognized on cultured rat neurons was substantially extra-synaptic. Antibody binding to primary hippocampal neurons was associated with receptor internalization. The NMDAR inhibitor MK-801 inhibited internalization without preventing mAb binding; the NMDAR inhibitor AP5 inhibited both mAb binding and internalization. Exposure of mice to the mAbs following permeabilization of the blood brain barrier increased voluntary wheel running activity, similar to low doses of the NMDAR inhibitor, MK-801. These data suggest that the anti-GluN1 antibodies had a role in the pathogenesis of ANRE in the patient from which they were obtained and provide additional insight into the nature of the pathogenic autoantibody response. In certain embodiments, a pathogenic autoantibody of an ANRE patient binds to the extracellular amino terminal domain (ATD) of NMDAR GluN1 subunit. In certain embodiments, a pathogenic autoantibody of an ANRE patient binds to the extracellular amino terminal domain (ATD) of NMDAR GluN1 subunit in open state/configuration. Such state can be stabilized by MK-801 and prevented by AD5.

As used herein, the term "autoantibody" or any variation thereof refers to an antibody produced by the immune system that is directed against one or more of the subject's/patient's own proteins, for example, NMDAR, NMDAR GluN1 subunit, or ATD of NMDAR GluN1 subunit. Such autoantibodies may exist in a patient's/subject's biological sample, for example, CSF or serum.

Figure 21:
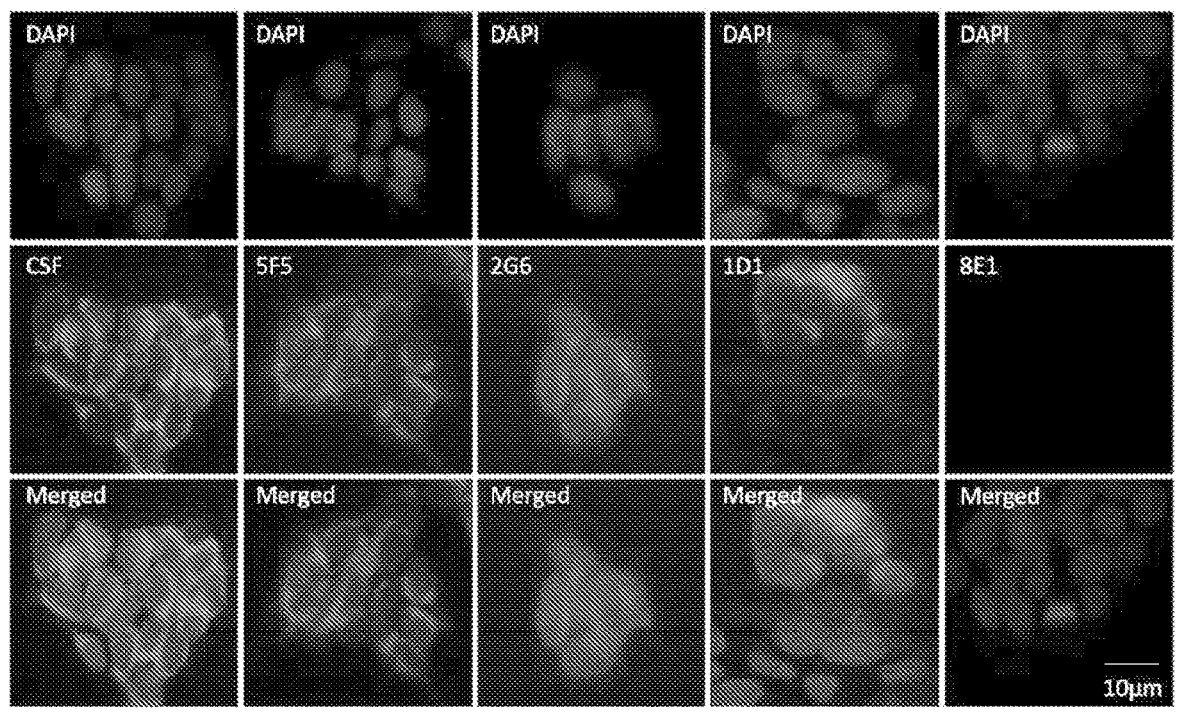
FIG. 21 shows the binding of human ANRE patient CSF and mAbs to 293T-ATD cells by immunofluorescence. 293T-ATD cells were stained with ANRE patient CSF, human ANRE mAbs 5F5, 2G6, and 1D1, or the 8E1 isotype control mAb (red). Nuclei were stained with DAPI (blue) and the cells were visualized by confocal microscopy. Scale bar=10 μm

Native membrane-bound forms of the NMDA receptor are reliably detected in CNS tissue by these antibodies, and methods for their use have been generated as a tool to diagnose autoimmune encephalitis caused by the production of anti-NMDA receptor antibodies. These antibodies have the unique ability to recognize native configurations of the NMDA receptor on the tissue cell surfaces not visualized by other antibodies available to this antigen. These configurations overlap with those recognized by the autoimmune antibodies produced in the disease, enabling a diagnostic test based on using these antibodies as a standard for comparison, to identify whether similar antibodies exist in serum or CSF obtained from suspected ANRE patients. Based on their unique attributes, these antibodies enable a diagnostic test for autoimmune encephalitis caused by autoantibodies that bind the NMDA receptor. Clinical proof of concept was demonstrated for the antibodies and methods in diagnosis of a patient confirmed to have anti-NMDA receptor-dependent autoimmune encephalitis (see data in FIGS. 21 and 25A-25D). In FIG. 21, CSF of an ANRE is immunoreactive with the 293T-ATD cell line, which indicates the presence of anti-NMDAR IgGs. In this experiment, the 5F5, 2G6, and 1D1 antibodies are used as positive controls that demonstrate how a human IgG reactive with NMDAR will behave in the assay, and furthermore confirm expression of the ATD antigen by the 293T-ATD cells. 8E1 is a human IgG that does not bind to NMDAR and is used as a negative control in the assay. Additional clinical samples were tested in this same assay, as shown in FIGS. 25A-25D. Three of four ANRE CSF samples and four of four ANRE serum samples tested were found to contain IgG immunoreactive with NMDAR, whereas none of four CSF samples or four serum samples from normal individuals contained an IgG reactive with NMDAR. In this way, the antibodies described herein can be used as comparators or positive controls in diagnostic assays useful for detecting antibodies reactive with NMDAR, the presence of which supports a diagnosis of ANRE.

Utilizing any of the nucleotide sequences encoding the heavy chain variable region of 5F5 (SEQ ID NO: 1), 2G6 (SEQ ID NO: 3) and 1D1 (SEQ ID NO: 6), the light chain variable region of 5F5 (SEQ ID NO: 2), 2G6 (SEQ ID NO: 4) and 1D1 (SEQ ID NO: 6), their encoded amino acid sequences for the heavy chain variable region of 5F5 (SEQ ID NO: 10), 2G6 (SEQ ID NO: 12) and 1D1 (SEQ ID NO: 14), the light chain variable region of 5F5 (SEQ ID NO: 11), 2G6 (SEQ ID NO: 13) and 1D1 (SEQ ID NO: 15), or nucleotide or amino acid sequences sharing at least about 80% (for example, about 80%, about 85%, about 90%, about 95%, about 96%, about 97%, about 98%, or about 99%), at least about 85%, at least about 90%, at least about 95%, at least about 96%, at least about 97%, at least about 98%, at least about 99%, or at least about 99.9% sequence identity therewith, other antibodies or fragments that specifically bind to the same NMDAR epitope(s), can be generated. In certain embodiments, the antibody or epitope binding fragment thereof as described herein comprise one or more of the CDRs as illustrated in Table 2. In certain embodiments, a described amino acid sequence sharing a certain percentage (which is less than 100%) identity to any one of SEQ ID NOs: 10, 11, 12, 13, 14, and 15 is different from the sequence with the corresponding SEQ ID NO in the region other than the CDR illustrated in Table 2. In certain embodiments, a described amino acid sequence sharing a certain percentage (which is less than 100%) identity to any one of SEQ ID NOs: 10, 11, 12, 13, 14, and 15 is able to bind to the NMDAR domain at an affinity of at least 10%, 20%, 30%, 40%, 50%, 60%, 70%, 80%, 90%, 95%, 100%, 1.5 fold, 2 fold, 3 fold, 4 fold, 5 fold, 10 fold of the affinity of 5F5 or 2G6 or 1D1. As used herein, affinity of an antibody or peptide binding fragment thereof refers to the strength with which an epitope binds to the antibody or peptide binding fragment thereof. Such strength may be measured as described in the Example.

Antibodies or fragments that bind to an NMDAR epitope include, in one embodiment a heavy chain variable domain and/or light chain variable domain sequence encoded by SEQ ID NOs: 1 and 2 (antibody 5F5), or sequences at least 85% identical thereto. In certain embodiments, the encoded variable domain has a sequence of SEQ ID NOs: 10 and/or 11, or a sequence at least 85%, at least 90%, at least 95%, at least 98% or at least 99% identical thereto. Antibodies or fragments that bind to an NMDAR epitope include, in one embodiment a heavy chain variable domain and/or light chain variable domain sequence having a sequence of SEQ ID NOs: 10 and/or 11, or sequences at least 85% identical thereto. Antibodies or fragments that bind to one or more NMDAR epitopes include, in one embodiment a heavy chain variable domain and/or light chain variable domain sequence encoded by sequences at least 90% identical to SEQ ID NOs: 1 and 2, or has/have a sequence at least 90% identical to a heavy chain variable domain and/or light chain variable domain sequence of SEQ ID NOs: 10 and 11. Antibodies or fragments that bind to one or more NMDAR epitope include, in one embodiment a heavy chain variable domain and/or light chain variable domain sequence encoded by sequences at least 95% identical to SEQ ID NOs: 1 and 2. Antibodies or fragments that bind to one or more NMDAR epitope include, in one embodiment a heavy chain variable domain and/or light chain variable domain sequence having sequences at least 95% identical to SEQ ID NOs: 10 and 11. Antibodies or fragments that bind to one or more NMDAR epitopes include, in one embodiment a heavy chain variable domain and/or light chain variable domain sequence encoded by sequences at least 98% identical to SEQ ID NOs: 1 and 2. Antibodies or fragments that bind to NMDAR epitopes include, in one embodiment a heavy chain variable domain and/or light chain variable domain sequence encoded by sequences at least 99% identical to SEQ ID NOs: 1 and 2. Antibodies or fragments that bind to one or more NMDAR epitopes include, in one embodiment a heavy chain variable domain and/or light chain variable domain sequence having sequences at least 98% identical to SEQ ID NOs: 10 and 11. Antibodies or fragments that bind to NMDAR epitopes include, in one embodiment a heavy chain variable domain and/or light chain variable domain sequence having sequences at least 99% identical to SEQ ID NOs: 10 and 11. Antibodies or fragments that bind to NMDAR epitopes include, in one embodiment a heavy chain variable domain and/or light chain variable domain sequence encoded by sequences of SEQ ID NOs: 1 and 2.

Antibodies or fragments that bind to an NMDAR epitope include, in one embodiment a heavy chain variable domain and/or light chain variable domain sequence encoded by SEQ ID NOs: 3 and 4 (antibody 2G6), or sequences at least 85% identical thereto. In certain embodiments, the encoded domain has a sequence of SEQ ID NOs: 12 and 13, or a sequence at least 85%, at least 90%, at least 95%, at least 98% or at least 99% identical thereto. Antibodies or fragments that bind to one or more NMDAR epitopes include, in one embodiment a heavy chain variable domain and/or light chain variable domain sequence encoded by sequences at least 90% identical to SEQ ID NOs: 3 and 4. Antibodies or fragments that bind to one or more NMDAR epitope include, in one embodiment a heavy chain variable domain and/or light chain variable domain sequence encoded by sequences at least 95% identical to SEQ ID NOs: 3 and 4. Antibodies or fragments that bind to one or more NMDAR epitopes include, in one embodiment a heavy chain variable domain and/or light chain variable domain sequence encoded by sequences at least 98% identical to SEQ ID NOs: 3 and 4. Antibodies or fragments that bind to one or more NMDAR epitopes include, in one embodiment a heavy chain variable domain and/or light chain variable domain sequence encoded by sequences at least 99% identical to SEQ ID NOs: 3 and 4. Antibodies or fragments that bind to one or more NMDAR epitopes include, in one embodiment a heavy chain variable domain and/or light chain variable domain sequence encoded by sequences of SEQ ID NOs: 3 and 4.

Antibodies or fragments that bind to an NMDAR epitope include, in one embodiment a heavy chain variable domain and/or light chain variable domain sequence having SEQ ID NOs: 12 and 13 (antibody 2G6), or sequences at least 85% identical thereto. Antibodies or fragments that bind to one or more NMDAR epitopes include, in one embodiment a heavy chain variable domain and/or light chain variable domain sequence having sequences at least 90% identical to SEQ ID NOs: 12 and 13. Antibodies or fragments that bind to one or more NMDAR epitope include, in one embodiment a heavy chain variable domain and/or light chain variable domain sequence having sequences at least 95% identical to SEQ ID NOs: 12 and 13. Antibodies or fragments that bind to one or more NMDAR epitopes include, in one embodiment a heavy chain variable domain and/or light chain variable domain sequence having sequences at least 98% identical to SEQ ID NOs: 12 and 13. Antibodies or fragments that bind to one or more NMDAR epitopes include, in one embodiment a heavy chain variable domain and/or light chain variable domain sequence having sequences at least 99% identical to SEQ ID NOs: 12 and 13.

Antibodies or fragments that bind to an NMDAR epitope include, in one embodiment a heavy chain variable domain and/or light chain variable domain sequence encoded by SEQ ID NOs: 5 and 6 (antibody 1D1), or sequences at least 85% identical thereto. In certain embodiments, the encoded domain has a sequence of SEQ ID NOs: 14 and 15, or a sequence at least 85%, at least 90%, at least 95%, at least 98% or at least 99% identical thereto. Antibodies or fragments that bind to one or more NMDAR epitopes include, in one embodiment a heavy chain variable domain and/or light chain variable domain sequence encoded by sequences at least 90% identical to SEQ ID NOs: 5 and 6. Antibodies or fragments that bind to one or more NMDAR epitope include, in one embodiment a heavy chain variable domain and/or light chain variable domain sequence encoded by sequences at least 95% identical to SEQ ID NOs: 5 and 6. Antibodies or fragments that bind to one or more NMDAR epitopes include, in one embodiment a heavy chain variable domain and/or light chain variable domain sequence encoded by sequences at least 98% identical to SEQ ID NOs: 5 and 6. Antibodies or fragments that bind to one or more NMDAR epitopes include, in one embodiment a heavy chain variable domain and/or light chain variable domain sequence encoded by sequences at least 99% identical to SEQ ID NOs: 5 and 6. Antibodies or fragments that bind to one or more NMDAR epitopes include, in one embodiment a heavy chain variable domain and/or light chain variable domain sequence encoded by sequences of SEQ ID NOs: 5 and 6.

Antibodies or fragments that bind to an NMDAR epitope include, in one embodiment a heavy chain variable domain and/or light chain variable domain sequence having sequences SEQ ID NOs: 14 and 15 (antibody 1D1), or sequences at least 85% identical thereto. Antibodies or fragments that bind to one or more NMDAR epitopes include, in one embodiment a heavy chain variable domain and/or light chain variable domain sequence having sequences at least 90% identical to SEQ ID NO: 14 and 15. Antibodies or fragments that bind to one or more NMDAR epitope include, in one embodiment a heavy chain variable domain and/or light chain variable domain sequence having sequences at least 95% identical to SEQ ID NO: 14 and 15. Antibodies or fragments that bind to one or more NMDAR epitopes include, in one embodiment a heavy chain variable domain and/or light chain variable domain sequence having sequences at least 98% identical to SEQ ID NO: 14 and 15. Antibodies or fragments that bind to one or more NMDAR epitopes include, in one embodiment a heavy chain variable domain and/or light chain variable domain sequence having sequences at least 99% identical to SEQ ID NO: 14 and 15.

The availability of these nucleic acid molecules encoding the heavy and light chains of the antibody enables production of a recombinant antibody, fragment or modifications using in vitro expression methods and cell-free expression systems known in the art. In vitro transcription and translation systems are commercially available, e.g., from Promega Biotech (Madison, WI) or Gibco-BRL (Gaithersburg, MD). The antibodies, epitope-binding fragments or modifications thereof may also be produced by expression in a suitable prokaryotic or eukaryotic system. Similarly, modifications may be inserted into these sequences by use of a variety of CRISPR techniques and other related, e.g., zinc finger, methodologies for modifying amino acid and nucleotide sequences.

These monoclonal antibodies 5F5, 2G6 and 1D1 and their variable chain sequences identified herein can be further used to prepare other forms of antibodies, e.g., chimeric antibodies, humanized antibodies, human antibodies. Other antibody fragments or ligands can be produced by screening phage display libraries, antibody fragments and mixtures thereof. Techniques for generating these types of antibodies and ligands are well-known in the art and the ligands themselves may be generated using the disclosed amino acid sequences of the above-identified monoclonal antibodies.

Chimeric antibodies may similarly be developed using known techniques. Chimeric antibodies are molecules in which different portions are derived from different animal species. Single chain antibodies may also be prepared by conventional methods, such as described in U.S. Pat. Nos. 4,946,778 and 4,704,692 using the variable portions of the polyclonal or monoclonal antibodies produced according to this invention. Antibody fragments, such as the Fab, F(ab)2 and scFv fragments and libraries thereof may also be employed in generation of the selective anti-NMDAR antibodies as described herein.

The production of bi-specific antibodies or ligands that specifically bind to two or more selected epitopes, can employ conventional techniques. See, e.g., Hornig N, Farber-Schwarz A., "Production of bispecific antibodies: diabodies and tandem scFv.", 2012, Methods Mol Biol., 907: 713-27; Speiss, C. et al, "Bispecific antibodies with natural architecture produced by co-culture of bacteria expressing two distinct half-antibodies, Jul. 7, 2013, Nature Biotechnology, 31:753-758; and Jonathan S Martin and Zhenping Zhu, "Recombinant approaches to IgG-like bispecific antibodies", 2005 Acta Pharmacologica Sinica, 26: 649-658.

The antibody and antibody fragment that bind to one of more NMDAR epitopes may comprise at least one CDR domain from the antibodies described above. For example, the antibody or antibody fragment may comprise at least one, two, three, four, five, or all six CDR domains of the anti-NMDR monoclonal antibodies 5F5, 2G6 or 1D1. In a particular embodiment, the antibody or antibody fragment comprises at least one or both of the heavy chain (HC) CDR domains. The HC variable or light chain (LC) variable domains may be encoded by nucleotide sequences longer or shorter than the domains identified in Table 1 by about 3, 6, 9, 12, or 15 nucleotides, particularly 3 or 6 nucleotides, at the 5' terminus and/or the 3' terminus, or longer or shorter than the domains identified in Table 2 by about 1, 2, 3, 4, or 5 amino acids at the amino terminus and/or the carboxy terminus.

The antibodies and antibody constructs may be further modified from those exemplified. For example, the antibodies may be humanized. In a particular embodiment, the selected sequences of the heavy or light chains of any of the antibodies disclosed herein (or a portion thereof) are inserted into the backbone of an antibody or antibody fragment construct. For example, the variable light domain and/or variable heavy domain of the antibodies described herein may be inserted into another antibody construct. Still another embodiment comprises a fully human Fab antibody fragment having a heavy chain variable domain encoded by a sequence of SEQ ID NO: 1, 3 or 5 and/or having a heavy chain sequence of SEQ ID NO: 10, 12 or 14, with a light chain variable domain coding sequence encoded by SEQ ID NO: 2, 4 or 6 or having a light chain amino acid sequence of SEQ ID NO: 11, 13 or 15. Still other modifications of the antibodies are single chain antibodies having a heavy chain variable domain encoded by a sequence at least 80, 85, 90, 95 or 99% identical to an sequence of SEQ ID NO: 1, 3, or 5, and a light chain variable domain encoded by a sequence at least 80, 85, 90, 95 or 99% identity to SEQ ID NO: 2, 4, or 6, and any combination thereof. Still other modifications of the antibodies are single chain antibodies having a heavy chain variable domain sequence at least 80, 85, 90, 95 or 99% identical to an sequence of SEQ ID NO: 10, 12, or 14, and a light chain variable domain sequence at least 80, 85, 90, 95 or 99% identity to SEQ ID NO: 11, 13, or 15, and any combination thereof. These sequences could be linked with a sequence encoding a peptide linker connecting the heavy and light chains/variable domains. These same combinations can be generated by use of the corresponding coding sequences, or sequences having at least 80, 85, 90, 95 or 99% identity thereto.

Still other antibody modifications employing the SEQ ID NOs disclosed herein, e.g., as taught by the techniques referenced in above-cited U.S. Pat. No. 9,902,772, incorporated by reference herein.

ATD Cell Line

Provided herein is a cell line stably expressing the extracellular amino terminal domain (ATD) of the NMDAR GluN1 subunit as well as composition and methods utilizing the cell line. In certain embodiments, the cell line allows post-translational modification (e.g., glycosylation) of the expressed protein. In certain embodiments, the cell line is a mammalian cell line. In further embodiments, the cell line is a human cell line. In yet further embodiments, the cell line is a human embryonic kidney cell line. In certain embodiments, the cell line is a human embryonic kidney 293 (i.e., HEK, or HEK-293 or 293) cell. In certain embodiments, the cell line is 293T cells. In certain embodiments, the NMDAR domain comprises an amino acid sequence of SEQ ID NO: 7 or a truncation thereof. Truncation of the domain may be about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid shorter in the C terminal or the N terminal of SEQ ID NO: 7. In certain embodiments, the NMDAR domain comprises an amino acid sequence of SEQ ID NO: 7 or a truncation thereof with about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 conservative amino acid substitution(s). In certain embodiments, the cell line expressing a fusion protein which comprises a target protein (for example, the NMDAR domain). In certain embodiments, the fusion protein further comprises at least one of: a tag, a cleavage site, and a transmembrane domain. In certain embodiments, the fusion protein comprises more than one tag, for example, 2, 3, 4, 5, 6, 7, 8, 9 or 10 tags. In certain embodiments, the cleavage site located between the transmembrane domain and the target protein (for example, the NMDAR domain). In certain embodiments, the fusion protein comprises the NMDAR domain, Myc-tag, 6×His tag, a TEV protease site, and a transmembrane domain of the human platelet-derived growth factor receptor (PDGFR). In certain embodiments, the fusion protein comprises, from N terminal to C terminal or from C terminal to N terminal, the NMDAR domain, one or more optional tags (for example, Myc-tag and 6×His tag), a cleavage site (for example, a TEV protease site), and a transmembrane domain of a transmembrane protein (for example, transmembrane domain of human platelet-derived growth factor receptor (PDGFR)).

As used herein, the terms "protein tag" "polypeptide tag" or "tag", which are used interchangeably herein, refer to a peptide sequence genetically grafted onto a protein, e.g., NMDAR ATD domain, resulting in a fusion protein, so that the tag alone or in concert with other components (for example, an antibody which specifically binds to the tag) enables the detection or production or purification of the fusion protein. Such tags include, without limitation, an affinity tag which are appended to a protein so that they can be purified from their crude biological source (for example, chitin binding protein (CBP) tag, maltose binding protein (MBP) tag, Strep-tag, glutathione-S-transferase (GST) tag, poly(His) tag, 6×Hist tag), epitope tags which are peptide sequence that might be specifically recognized by a high-affinity reliable antibody (for example, V5-tag, Myc-tag, HA-tag, Spot-tag and NE-tag), fluorescence tags (for example, Green Fluorescent protein (GFP) and its variants), chromatography tags which are used to alter chromatographic properties of the protein to afford different resolution across a particular separation methods, or a solubilization tags for expressing a protein in chaperone-deficient species to assist in the proper folding in proteins and keep them from precipitating.

As used herein, the term "cleavage site" refers to peptide sequences or peptide motifs at which a site-specific protease cleaves or cuts the protein. In certain embodiments, a cleavage site is used to cleave off the transmembrane domain or the target protein from the fusion protein, so that the target protein can be released from the cell. Such cleavage site includes, but is not limited to, TEV cleavage site (or TEV protease site, recognizing a peptide sequence of Glu-Asn-Leu-Tyr-Phe-Gln↓Gly, SEQ ID NO: 16, or Glu-Asn-Leu-Tyr-Phe-Gln↓Ser, SEQ ID NO: 17, wherein the arrow indicates the site where a TEV protease cleaves), HIV-1 protease cleavage site, myristoylation signal sequence fused to Tobacco Etch Virus (TEV) protease cleavage site, or preScission protease cleavage site. Additional cleavage sites are available in the art. See, for example, parts.igem.org/Protein_domains/Cleavage.

As used herein, the term "transmembrane domain" refers to a membrane-spanning region of the protein, use of which allows anchoring the NMDAR ATD domain and/or the fusion protein to the outer cell plasma membrane. In certain embodiments, it denotes the presence of both alpha-helical transmembrane regions and the membrane spanning regions of beta-barrel transmembrane protein. The transmembrane domains can be experimentally determined or predicted by different tools, for example, www.cbs.dtu.dk/services/TMHMM/. In certain embodiments, the helices are visible in structures of membrane proteins determined by X-ray diffraction. They may also be predicted on the basis of hydrophobicity scales. Because the interior of the bilayer and the interiors of most proteins of known structure are hydrophobic, it is presumed to be a requirement of the amino acids that span a membrane that they be hydrophobic as well. However, membrane pumps and ion channels also contain numerous charged and polar residues within the generally non-polar transmembrane segments. In certain embodiments, the transmembrane domain is the transmembrane domain of PDGFR.

In certain embodiments, the cell line comprises a nucleic acid sequence encoding the NMDAR domain as described herein. In certain embodiments, the nucleic acid encoding a fusion protein as described herein.

In certain embodiments, the nucleic acid sequence which encodes a fusion protein as described herein is introduced into the cell line as a vector. Such vector may be a nanoparticle, a liposome, a viral vector (for example, a lentivirus, a retrovirus, an adenovirus, an adeno-associated virus or any hybrid thereof), or a non-viral vector (for example, a plasmid, or an artificial chromosome). Such introduction may be performed by transfection or transduction which may be performed by one of skill in the art.

We developed a stable cell line that homogeneously expresses the ATD epitope(s). The 293T-ATD cell line expresses the amino terminal domain (ATD) (SEQ ID NO: 7) of the GluN1 NMDAR subunit (NR1) as a fusion protein (SEQ ID NO: 8) on the outer plasma membrane of 293T cells, thereby creating a stable cell population (293T-ATD) that is recognized by ANRE patient monoclonal antibodies, for example, in flow cytometry and immunofluorescence assays. The ATD fusion protein also contains a Myc tag useful as a positive control for antigen expression and a 6×HIS tag, which provide functionality for immunoassays and antigen purification, and a TEV protease site, which allows the ATD domain to be specifically released from the cells in essentially pure form, and the PDGF receptor transmembrane domain, which anchors the ATD to the outer plasma membrane.

Retroviral transduction of the fusion gene SEQ ID NO: 9, followed by FACS selection of cells recognized by the murine anti-GluN1 mAb, resulted in a population of 293T-ATD cells with uniform expression levels. The 293T-ATD cell line specifically bound a commercial anti-GluN1 mAb, CSF from an ANRE patient, and the three anti-NMDAR mAbs in both flow cytometry and immunofluorescence microscopy experiments.

Specifically, as demonstrated in the Examples below, inventors assessed ATD binding in cell-based assays and ELISAs with a commercial NR1 mAb, ANRE patient CSF, three human anti-NR1 IgG mAbs from an ANRE patient (5F5, 2G6 and 1D1), and an additional panel of ANRE and normal patient sera and CSF samples. ATD mobilized from the 293T ATD cell line maintained the pathogenic ANRE epitopes in ELISA binding assays. CSF (3/4) and sera (4/4) from ANRE patients also bound the 293T-ATD cell line, whereas normal CSF and sera did not. These experiments demonstrate that pathogenic ANRE epitopes on the ATD are preserved when displayed on the outer plasma membrane.

Because the ATD fusion protein contained to a TEV protease site, it could be released from PBS-washed 293T-ATD cells with TEV protease, resulting in an essentially pure, intact ATD that preserved pathogenic antigens and could be used in ELISAs without additional purification. When adhered to an ELISA plate by an anti-6×HIS antibody, the ATD was specifically recognized by the commercial NR1 and human ANRE mAbs. In soluble form, the ATD demonstrated linear binding activity to a plate-adherent 5F5 anti-NMDAR mAb.

A panel of ANRE and normal patient CSF and sera was tested for IgG antibodies reactive with the 293T-ATD cells. Four of five ANRE patient CSF (including the standard positive control sample shown in FIG. 21) and all four ANRE patient sera bound the cell line, whereas none of the normal samples did. Additional clinical studies of ANRE patient IgGs will determine the spectrum of pathogenic antibodies that recognize the ATD in these assay formats.

Taken together, these assays in Examples 5-6 demonstrate that the soluble ATD maintains ANRE pathogenic epitopes. It is therefore potentially adaptable to a variety of non-cell-based test formats to diagnose ANRE, including ELISAs and lateral flow assays. In addition, the soluble ATD is useful for anti-NMDAR mAb screening, epitope mapping, and affinity measurement.

The 293T-ATD cell line is adaptable to a variety of assay formats to identify antibodies associated with ANRE, including cell-based and soluble antigen formats, and is useful in a method to produce complex proteins for research, drug discovery, and clinical diagnosis. This cell line may be useful in improving standardization of the assays and providing antigen that could be used in commercial solid state assay systems. The 293T-ATD cell line is also potentially suitable for use in cell-based assays to diagnose ANRE. The 293T-ATD cell line may potentially substitute for transiently transfected cells in clinical diagnostic testing.

Our method of expressing proteins in a membrane-tethered, cleavable form offers advantages for the production of a wide variety of proteins in mammalian cells. First, stable, high-expressing cells can be readily identified and isolated, and the Myc tag can be used as a positive control for protein expression. Isolating pure protein is straightforward, because the cells themselves provide a solid phase for separating the antigen from the culture medium, and the precise activity of the TEV protease releases essentially pure recombinant protein from the cells. The 6×HIS tag in the fusion protein can be used for additional column chromatography, if necessary, especially if large or very pure protein preps are required, and both the Myc and 6×HIS tags can be used to capture the secreted protein for solid phase binding assays. Furthermore, any protein can potentially be sorted to the outer plasma membrane by incorporating a heterologous N-terminal signal peptide[41].

Also provided herein is a method of producing a target protein optionally with a tag. This method comprises steps of culturing cells as described herein, and cleaving and releasing the protein from the cell.

The 293T-ATD cell line enables improved diagnostic tests for ANRE and studies of antibodies associated with ANRE. For example, it is suitable for use in diagnostic assays in which the antibodies of the present invention are used as standards, comparators, or positive controls. As demonstrated in FIGS. 21 and 25A-25D, the assays show very low background signal with an isotype control monoclonal antibody (8E1) and with normal CSF or serum. Ectopic expression of proteins in a tagged, cleavable form, on the outer plasma membrane of cultured mammalian cells, has the potential to expand the spectrum of antigens available for research, drug discovery, and clinical diagnosis.

Assays and Methods

ANRE is a potentially fatal auto-immune encephalitis mediated by antibodies that bind NR1 (i.e., the amino terminal domain (ATD) of the GluN1 NMDAR subunit), in one embodiment, in the hippocampus. Definitive diagnosis of ANRE requires detection of anti-NR1 IgG in patient CSF. The antigens recognized by the pathogenic IgGs 5F5, 2G6 and 1D1 in ANRE are conformational and depend on post-translational glycosylation that can only be produced in a mammalian cell. Because NMDAR over-expression can be toxic to cultured cells, the first-line clinical tests for ANRE are a CBA or ELISA that uses 293T cells transiently expressing NMDAR. The need for transfected cells to test anti-NMDAR IgG introduces variability into the assay and limits the types of tests that can be used for ANRE diagnosis.

Thus, novel diagnostic assays are provided using the ATD fusion protein cell line described herein described above. Additionally, an antibody, or a variant thereof, or an epitope binding fragment thereof may also be used.

Thus, a novel diagnostic reagent composition comprises a cell line as described herein, for example, the ATD fusion protein cell line. Also provided is a method using the cell line as described herein or fusion protein expressed by the cell line for use in diagnosing ANRE.

In certain embodiments, the reagent composition comprises at least one recombinant, synthetic or monoclonal human antibody or fragment thereof as described herein. In certain embodiment, the reagent composition comprises at least one recombinant, synthetic or monoclonal human antibody or fragment thereof that binds to an N-methyl-D-aspartate Receptor (NMDAR) epitope, wherein said antibody or fragment comprises at least one heavy chain variable domain sequence encoded by a nucleic acid sequence that is at least 85% identical to SEQ ID NOs. 1, 3, or 5; or a light chain variable domain sequence encoded by a nucleic acid sequence that is at least 85% identical to SEQ ID NOs: 2, 4, or 6. In another aspect, said antibody or fragment comprises at least one heavy chain variable domain sequence having a sequence that is at least 85% identical to SEQ ID NOs. 10, 12, or 14; or a light chain variable domain sequence having a sequence that is at least 85% identical to SEQ ID NOs: 11, 13, or 15. Any of the antibodies described above and based on these sequences can be used in diagnostic assays for ANRE. In one embodiment, a diagnostic composition contains a mixture of two or more of said antibodies or epitope binding antibody fragments described herein. In still another embodiment, a diagnostic composition contains an additional anti-NMDAR antibody or antibody fragment that binds to a different NMDAR epitope than do the antibodies and fragments described here.

In certain embodiments, such diagnostic reagent compositions can include a target protein, for example as part of a fusion protein and/or expressed on the cell surface of a cell line as described herein. In certain embodiments, such diagnostic reagent compositions can include an antibody, or an epitope binding fragment, as described herein. In certain embodiments, a target protein (for example, ATD) of a fusion protein expressed by the cell line is cleaved at the cleavage site, released from the cell line, and coupled covalently or non-covalently to a detectable label. In certain embodiments, the fusion protein is coupled covalently or non-covalently to a detectable label. In certain embodiments, the antibody, or a variant thereof, or an epitope binding domain thereof, is coupled covalently or non-covalently to a detectable label. In certain embodiments, the diagnostic reagent composition further comprises a ligand which specifically binds to a human antibody (for example, a human autoantibody, or a human autoantibody which specifically binds to ATD). In a further embodiment, the ligand does not bind to a target protein, a fusion protein, or an antibody/variant/fragment as described herein, if such protein/antibody/variant/fragment is present with the ligand. For example, the ligand specifically binds to an Fc fragment of human Immunoglobulin (such as IgG). Alternatively, the site on the protein/antibody/variant/fragment which may bind to the ligand has been blocked via another protein or a substrate for immobilization or has been mutated. In certain embodiments, the ligand is coupled covalently or non-covalently to a detectable label. In a further embodiment, such ligand is an antibody, a variant thereof, or an epitope binding fragment thereof. In yet a further embodiment, such ligand is an anti-human IgG antibody, which specifically binds to an anti-human IgG, for example, www.abcam.com/goat-human-igg-hl-fitc-ab6854.html. Further, one of skill in the art would understand that in a diagnostic reagent composition comprising more than one component (such as antibody, or a target protein) which is coupled with a detectable label, each component may have a detectable label which is different from any one of the other components. For example, a diagnostic reagent may comprise an ATD which is labeled with a first detectable label (such as a green fluorescent protein) and an anti-human IgG ligand which is labeled with a second detectable label (such as a red fluorescent protein). Colocalization of the different detectable labels indicates binding of the target protein (e.g., ATD in open state, ATD, NMDAR GluN1 subunit, NMDAR) and autoantibodies in a patient's biological sample, such as serum or CSF.

As used herein, the target protein may refer to a NMDAR epitope, a polypeptide/protein comprising a NMDAR epitope, ATD in open state, ATD, NMDAR GluN1 subunit, NMDAR, or the NMDAR domain as described herein.

As used herein, detectable labels can include one or more of an enzyme label, a fluorescent label, a radioisotope, or a chemiluminescent label. As used herein, "labels" or "reporter molecules" or "detectable label components" are chemical or biochemical moieties useful in association with an antibody or binding fragment, that alone or in concert with other components enable the detection of binding between the antibody and its target. Such labels or components include, without limitation, a protein tag, fluorescent agents, chemiluminescent agents, chromogenic agents, quenching agents, radionucleotides, enzymes, enzymatic substrates, cofactors, inhibitors, radioactive isotopes, magnetic particles, and other moieties known in the art. In certain embodiments, the "labels" or "reporter molecules" are covalently or non-covalently associated with the antibody. Such labels are capable of generating a measurable signal alone, e.g., radioactivity, or in association with another component, e.g., an enzymatic signal in the presence of a substrate.

In certain embodiments, such diagnostic reagent compositions can include the antibody, or a variant thereof, or an epitope-binding fragment thereof as described herein which is immobilized on a substrate. In certain embodiments, a target protein (for example, ATD) of a fusion protein expressed by the cell line is cleaved at the cleavage site, released from the cell line, and is immobilized on a substrate. In certain embodiments, the target protein is immobilized on a substrate which is coated with a ligand. Such ligand may be the antibody, or a variant thereof, or an epitope binding fragment thereof, as described herein (for example, 5F5 or 2G6), so that the antibody, variant thereof, or epitope binding fragment thereof binds to the target protein (for example, ATD in open state, ATD, NMDAR GluN1 subunit, or NMDAR) and immobilized the target protein on a substrate.

In certain embodiments, the cell line is immobilized on a substrate (for example, a magnetic bead).

In certain embodiments, the fusion protein is immobilized on a substrate. In certain embodiments, the fusion protein is immobilized on a substrate which is coated with a ligand. Such ligand specifically binds to the fusion protein. In certain embodiments, the ligand specifically binds to the target protein in the fusion protein. Such ligand may be the antibody, or a variant thereof, or an epitope binding fragment thereof, as described herein, so that the antibody, variant thereof, or epitope binding fragment thereof binds to the target protein (for example, ATD in open state, ATD, NMDAR GluN1 subunit, or NMDAR) and immobilized the target protein on a substrate. In certain embodiments, the ligand specifically binds to a tag of the fusion protein, for example, an anti-Flag antibody, an anti-Myc antibody, or an anti-6× His tag antibody, so that the fusion protein is immobilized on a substrate.

In certain embodiments, the antibody, or a variant thereof, or an epitope binding domain thereof, is immobilized on a substrate.

In certain embodiments, the diagnostic reagent composition further comprises a ligand which specifically binds to a human antibody (for example, a human autoantibody, or a human autoantibody which specifically binds to ATD). In a further embodiment, the ligand does not bind to a target protein, a fusion protein, or an antibody/variant/fragment as described herein, if such protein/antibody/variant/fragment is present with the ligand. Alternatively, the site on the protein/antibody/variant/fragment which may bind to the ligand has been blocked via another protein or a substrate for immobilization or has been mutated. In certain embodiments, the ligand is immobilized on a substrate. In a further embodiment, such ligand is an antibody, a variant thereof, or an epitope binding fragment thereof. In yet a further embodiment, such ligand is an anti-human IgG antibody, which specifically binds to an anti-human IgG, for example, www.abcam.com/goat-human-igg-hl-fitc-ab6854.html. In certain embodiments, such ligand specifically binds to Fc fragment of a human immunoglobulin (such as IgG).

In certain embodiments, the substrate is a plate, a slide, a pipette, a bead, a magnetic bead, a gel, a membrane (for example, a nitrocellulose membrane), a chip, or a microchip, for an enzyme linked immunosorbent assay (ELISA), a lateral flow assay, a radioimmunoassay (RIA), Fluorescence-activating cell sorting (FACS), a western blot, an immunoprecipitation or another immunoassay. In certain embodiments, the substrate may refer to the cell line on which the fusion protein is expressed and/or the target protein portion of the fusion protein that presents on the outer cell membrane.

The diagnostic reagents described herein can be used separately, provided in a mixture or provided in a kit with all necessary components to practice the assay of choice. In one embodiment, the reagent is a mixture of two or three of the anti-NMDAR antibodies that bind to different, non-overlapping, NMDAR ATD epitopes, e.g., the mAbs 5F5, 2G6 and 1D1 or recombinant or synthetic antibodies or fragments that bind the same epitopes as the mAbs.

An assay method for diagnosis of encephalitis (for example, ANRE) can utilize the diagnostic reagents and kits as described herein. In one embodiment an assay method for diagnosis of autoimmune encephalitis comprises contacting a biological sample obtained from a subject or patient who is suspected of having encephalitis with a target protein (for example, ATD in open state, ATD, NMDAR GluN1 subunit, or NMDAR). In certain embodiments, the method may further comprise contacting an antibody, or variant thereof, or an epitope binding domain thereof, or a mixture of different antibody/variant/fragments, as described herein with the target protein, serving as a positive control. In certain embodiments, the method may further comprise contacting a biological sample from a subject who does not have encephalitis, or a biological sample pooled from subjects who do not have encephalitis with a target protein, serving as a negative control. In certain embodiments, the method comprises contacting a biological sample obtained from a subject or patient who is suspected of having encephalitis with a target protein with or without presence of an antibody, or variant thereof, or an epitope binding domain thereof, or a mixture of different antibody/variant/fragments as described herein. The presence of the antibody/variant/fragment/mixture provides competitive binding to the target protein. In certain embodiments, the method comprises contacting a biological sample obtained from a subject or patient who is suspected of having encephalitis with a target protein with different concentrations of an antibody, or variant thereof, or an epitope binding domain thereof, or a mixture of different antibody/variant/fragments as described herein. Various concentrations of the antibody/variant/fragment/mixture provide different level of a competitive binding to the target protein.

In certain embodiments, the method further comprises detecting the level of binding between the biological sample or a component thereof (for example, an human antibody, a human autoantibody, a human anti-NMDAR antibody, or a human anti-ATD antibody) and the target protein (for example, ATD in open state, ATD, NMDAR GluN1 subunit, or NMDAR). In a further embodiment, the method further comprises diagnosing the patient as having encephalitis when said level is greater than a negative control. Alternatively or additionally, the method further comprises diagnosing the patient as having encephalitis when said level is at least about 10%, about 20%, about 30%, about 40%, about 50%, about 60%, about 70%, about 80%, about 90%, about 100%, about 1 fold, about 2 fold, about 5 fold, or about 10 fold of that of a positive control. In certain embodiments, such detection may be performed via detecting the competitive binding of the antibody/variant/fragment/mixture as described herein with the target protein when the biological sample also is contacted with the target protein. In certain embodiments, the method further comprises diagnosing the patient as having encephalitis when competitive binding using the antibody/variant/fragment/mixture as described herein reduces the level of binding between components of the tested biological sample with a target protein to at least about 10%, about 20%, about 30%, about 40%, about 50%, about 60%, about 70%, about 80%, about 90%, about 95% of the one without competitive binding. In certain embodiments, the method further comprises diagnosing the patient as having encephalitis when an increase in competitive binding (for example, an increase in the concentration of the antibody/variant/fragment/mixture) leads to a decreased level of binding between component of the tested biological sample and the target protein. In certain embodiments, such method may be used for detecting presence of pathogenic autoantibody in the tested biological sample. In certain embodiments, such method may be used for determining affinity between the pathogenic autoantibody in the tested biological sample and the target protein.

In certain embodiments, such detection may be performed by detecting level of colocalization of detectable labels of the target protein and the ligand (for example, an anti-human immunoglobulin antibody) which specifically binds to the component of the biological sample (for example, a human autoantibody). In a further embodiment, the method further comprises diagnosing the patient as having encephalitis when such colocalization is detected, while no colocalization is detected in a negative control. In yet a further embodiment, the method further comprises diagnosing the patient as having encephalitis when such colocalization is detected at a level greater than that in a negative control. Alternatively or additionally, the method further comprises diagnosing the patient as having encephalitis when such colocalization is detected at a level which is at least about 10%, about 20%, about 30%, about 40%, about 50%, about 60%, about 70%, about 80%, about 90%, about 100%, about 1 fold, about 2 fold, about 5 fold, or about 10 fold of that of a positive control. In certain embodiments, such detection may be performed via detecting the competitive binding of the antibody/variant/fragment/mixture as described herein with the target protein when the biological sample also is contacted with the target protein. In certain embodiments, the method further comprises diagnosing the patient as having encephalitis when competitive binding using the antibody/variant/fragment/mixture as described herein reduces colocalization level between components of the tested biological sample with a target protein to at least about 10%, about 20%, about 30%, about 40%, about 50%, about 60%, about 70%, about 80%, about 90%, about 95% of the one without competitive binding. In certain embodiments, the method further comprises diagnosing the patient as having encephalitis when an increase in competitive binding (for example, an increase in the concentration of the antibody/variant/fragment/mixture) leads to a decreased level of colocalization between components of the tested biological sample and the target protein. In certain embodiments, the ligand does not bind to a target protein, a fusion protein, or an antibody/variant/fragment as described herein, if such protein/antibody/variant/fragment is present with the ligand. Alternatively, the site on the protein/antibody/variant/fragment which may bind to the ligand has been blocked via another protein or a substrate for immobilization or has been mutated. In certain embodiments, such method may be used for detecting presence of pathogenic autoantibody in the tested biological sample. In certain embodiments, such method may be used for determining affinity between the pathogenic autoantibody in the tested biological sample and the target protein.

In certain embodiments, such detection may be performed via detecting colocalization of detectable labels of the antibody/variant/fragment as described herein and the ligand (for example, an anti-human IgG antibody) which specifically binds to the component of the biological sample (for example, a human autoantibody). In a further embodiment, the method further comprises diagnosing the patient as having encephalitis when such colocalization is detected while no colocalization is detected in a negative control. In yet a further embodiment, the method further comprises diagnosing the patient as having encephalitis when such colocalization is detected at a level greater than that in a negative control. Alternatively or additionally, the method further comprises diagnosing the patient as having encephalitis when such colocalization is detected at a level which is at least about 10%, about 20%, about 30%, about 40%, about 50%, about 60%, about 70%, about 80%, about 90%, about 100%, about 1 fold, about 2 fold, about 5 fold, or about 10 fold of that of a positive control. In certain embodiments, such detection may be performed via detecting the competitive binding of the antibody/variant/fragment/mixture as described herein with the target protein when the biological sample also is contacted with the target protein. In certain embodiments, the method further comprises diagnosing the patient as having encephalitis when competitive binding using the antibody/variant/fragment/mixture as described herein reduces colocalization level between components of the tested biological sample with the antibody/variant/fragment/mixture to at least about 10%, about 20%, about 30%, about 40%, about 50%, about 60%, about 70%, about 80%, about 90%, about 95% of the one without competitive binding. In certain embodiments, the method further comprises diagnosing the patient as having encephalitis when an increase in competitive binding (for example, an increase in the concentration of the antibody/variant/fragment/mixture) leads to a decreased level of colocalization between component of the tested biological sample and the antibody/variant/fragment/mixture. In certain embodiments, the ligand does not bind to a target protein, a fusion protein, or an antibody/variant/fragment as described herein, if such protein/antibody/variant/fragment is present with the ligand. Alternatively, the site on the protein/antibody/variant/fragment, which may bind to the ligand, has been blocked via another protein or a substrate for immobilization or has been mutated. In certain embodiments, such method may be used for detecting presence of pathogenic autoantibody in the tested biological sample. In certain embodiments, such method may be used for determining affinity between the pathogenic autoantibody in the tested biological sample and the target protein.

In certain embodiments, such detection may be performed by detecting level of the detectable label of the ligand (for example, an anti-human immunoglobulin antibody) which specifically binds to component of the biological sample (for example, a human autoantibody) while the target protein or the target protein of the fusion protein, or the target protein expressed in the cell line is immobilized on a substrate. In a further embodiment, the method further comprises diagnosing the patient as having encephalitis when the detectable label is detected at a level greater than that in a negative control. Alternatively or additionally, the method further comprises diagnosing the patient as having encephalitis when the detectable label is detected at a level which is at least about 10%, about 20%, about 30%, about 40%, about 50%, about 60%, about 70%, about 80%, about 90%, about 100%, about 1 fold, about 2 fold, about 5 fold, or about 10 fold of that of a positive control. In certain embodiments, such detection may be performed via detecting the competitive binding of the antibody/variant/fragment/mixture as described herein with the target protein when the biological sample is contacted with the target protein. In certain embodiments, the method further comprises diagnosing the patient as having encephalitis when competitive binding using the antibody/variant/fragment/mixture as described herein reduces the level of the detectable label to at least about 10%, about 20%, about 30%, about 40%, about 50%, about 60%, about 70%, about 80%, about 90%, about 95% of the one without competitive binding. In certain embodiments, the method further comprises diagnosing the patient as having encephalitis when an increase in competitive binding (for example, an increase in the concentration of the antibody/variant/fragment/mixture) leads to a decreased level of the detectable label. In certain embodiments, the ligand does not bind to a target protein, a fusion protein, or an antibody/variant/fragment as described herein, if such protein/antibody/variant/fragment is present with the ligand. Alternatively, the site on the protein/antibody/variant/fragment, which may bind to the ligand, has been blocked via another protein or a substrate for immobilization or has been mutated. In certain embodiments, such method may be used for detecting presence of pathogenic autoantibody in the tested biological sample. In certain embodiments, such method may be used for determining affinity between the pathogenic autoantibody in the tested biological sample and the target protein.

In certain embodiments, the methods as described herein are performed in the format of ELISA, RIA, FACS or lateral flow assay. For example, the target protein (for example, ATD in open state, NMDAR GluN1 subunit, NMDAR, NMDAR domain as described herein) may be immobilized on an ELISA plate via the antibody/variant/fragment/mixture as described thereof or via an antibody which specifically binds to the protein tag of the fusion protein. A biological sample of a subject/patient who is suspected of having the disease is optionally diluted with appropriate solution or concentrated, then applied to the target protein coated ELISA plate, and incubated and washed as appropriate. A ligand which specifically binds to anti-human immunoglobin antibody and is coupled with a detectable label (for example, a fluorescent protein) is then applied to the ELISA plate. Detection of the detectable label indicates presence of pathogenic autoantibody in the tested sample, showing the patient has the disease. Another example is lateral flow assay. See, e.g., en.wikipedia.org/wiki/Lateral_flow_test. A possible assay includes the following steps: (a) a detectable tag is added to the tested biological sample in the conjugate pad, for example, via a ligand which specifically binds to a human immunoglobulin/antibody; (b) in the nitrocellulose membrane section of the lateral flow assay, the target protein is provided for potential binding; and (c) the test line provides immobilized antibody/variant/fragment/mixture as described herein. If pathogenic autoantibody which specifically binds to the target protein exists in the tested biological sample, a complex would form at the test line, wherein the complex comprises the pathogenic autoantibody, the target protein, the antibody/variant/fragment as described herein, and the ligand with detectable label.

More specifically, the biological sample, e.g., whole blood, plasma, serum, CSF, or a neuronal tissue, specifically binds or forms a complex with the NMDAR domain, thus labels the NMDAR domain, or immobilizes the NMDAR domain, or binds to the NMDAR domain in a competitive manner to a pathogenic autoantibody in a tested biological sample. However, other NMDAR antibodies or a mixture of the NMDAR antibodies/variants/fragments can be used in a similar fashion. The resulting complexes of antibody-bound NMDAR on cells in the sample may be detected. Such detection can be based upon separation of the bound cells from unbound cells in the sample. In certain embodiments, the antibodies are associated with a detectable label component. In still other embodiments, the antibody is immobilized on a substrate. The detection and measurement of the antibody bound cells or antigen-antibody complexes in the sample may be accomplished by a physical characteristic, such as the difference in size or weight of the bound cells vs. the unbound cells which do not have NMDAR on their surfaces. Such detection and/or separation techniques can thus employ appropriately sized filtration units, or the use of flow cytometry, or chromatographic or centrifugation techniques (size exclusion or weight exclusion), among others known to the art. Alternatively, where the antibody is associated with a detectable label component, the detection and separation may employ methods of detecting independently detectable labels by radioactivity, light wavelength, or similar methods. Where the antibody is associated with a label which is capable of generating a measurable detectable signal when contacted with another label component, these methods employ the addition of such components and suitable detection methods dependent upon the signal generated.

Where the antibody is immobilized on a physical substrate, the separating step can include washing the unbound cells and other debris in the sample from the substrate and detecting, or measuring, the bound cells on the substrate. In another embodiment, the separating step comprises treating the sample with a reagent, such as an enzymatic substrate, where the label is an enzyme. The interaction of the label and enzymatic substrate or cofactor identifies labeled complexes from unbound cells to permit enumeration of levels of NMDAR in the sample.

This method may be useful in diagnosing encephalitis as Anti-N-methyl-D-aspartate Receptor Encephalitis (ANRE). In one embodiment, the method permits diagnosis to occur at an early stage of said autoimmune encephalitis. In another embodiment, the diagnosis is useful in situations in which the patient presents with psychiatric symptoms that may have broad differential diagnoses.

In another embodiment, the assay method can detect and measure competitive binding to the NMDAR epitope(s) with autoimmune antibodies in the patient's biological sample.

Such assay methods can detect antibody to NMDAR binding by an enzyme linked immunosorbent assay (ELISA), a competitive-binding assay, a capture assay, a Western blot, a radioimmunoassay, or a fluorescence-activated cell sorting (FACS) assay. One desirable assay is described in Example 7. Still other assay formats may be similarly adapted to use of the non-overlapping NMDAR epitope binding antibodies and fragments. In one embodiment, patient serum or CSF can be tested for binding to the ATD cell line described above in comparison to a combination of anti-NMDAR mAbs. The data in FIGS. 15 and 16 were performed with the ATD cell line, and clearly support this embodiment. This defined human anti-NMDAR antibody combination (5F5, 2G6 and 1D1), whether polyclonal, monoclonal, recombinant or synthetic, is anticipated to be superior to a single anti-NMDAR mAb in certain diagnostic indications. Combined with the ATD antigen system, these mAbs to non-overlapping epitopes enable types of assays that cannot be done with existing antibodies. See Example 7.

Different ANRE antibodies differ substantially in their pathogenic effects. The fact that 5F5, 2G6 and 1D1 bind non-overlapping epitopes on NMDAR suggests that some cases of ANRE may integrate the effects of multiple antibodies. No one mAb completely colocalized with the GluN1 detected by patient IgGs or non-human, commercial antibodies in any of the tissues or cell lines that were examined as described in the examples below. Furthermore, 5F5 preferentially bound extrasynaptic NMDAR, while ANRE patient IgGs as a whole bind more to synaptic receptors.[4] Although synaptic NMDAR signaling is crucial for synaptic plasticity, learning, and memory; extrasynaptic NMDAR signaling links to excitotoxicity and cell death.[8] This supports a model in which the symptoms of ANRE reflect the integration of excitatory/inhibitory imbalances of neuronal circuit function and the balance between synaptic and extrasynaptic NMDAR. These effects depend on the types and titers of different antibodies expressed in each patient.

Our studies of GluN1 binding in ANRE showed that the antibodies preferentially bind to the NMDAR in its open state.[4,7] Consistent with these results, 5F5 and 2G6 both bind in the presence of MK-801, which stabilizes NMDAR in the open state, but not AP5, which prevents NMDAR opening.[30] Our observation that MK-801 inhibits internalization, but not binding, suggests that receptor activation by 5F5 or 2G6 is required for internalization. This contrasts with the previous observation that AP5 did not impede receptor down modulation induced by ANRE CSF.[31] However, important methodological differences exist, in that Moscato et al. measured NMDAR internalization induced by CSF over 12 h, whereas we measured mAb internalization at 45 min. In ANRE, chronic anti-NMDAR IgG treatment of neurons is proposed to lead to internalization and destruction of NMDARs, resulting in reduced synaptic NMDAR currents and impairment of NMDAR-dependent processes such as long-term potentiation (LTP).[4,5,32]

Without wishing to be bound by theory, a reasonable hypothesis is that ANRE patient antibodies directly cause their symptoms through NMDAR hypofunction, resulting in the amnesia and psychosis seen in anti-NMDAR encephalitis. The examples using the mAbs described here suggest that these antibodies can result from NMDAR antigen-dependent somatic hypermutation, even in the absence of a teratoma. NMDAR antagonists induce psychosis in humans[33] and NMDAR hypofunction has been associated with schizophrenia in mouse models.[33-36] However, other features of ANRE, such as seizures and dyskinesias, are not readily explained by global NMDAR hypofunction, as these can also reflect overactivation of NMDAR.[37] If NMDAR internalization by IgGs requires receptor activation, it follows that the initial presentation of ANRE may reflect overactivation prior to hypofunction. In the case of the 5F5 mAb, this may reflect overactivation primarily at extrasynaptic sites. The availability of the antibodies and fragments derived from ANRE patients also offers the opportunity to explore the mechanisms that underlie the protean manifestations of ANRE and to create immune assays that detect specific types of anti-NMDAR antibodies in patients and may have prognostic importance. The antibodies and fragments described herein may be useful in any assay, in addition to those described above, as selected by one of skill in the art from among the many known assay formats.

EXAMPLES

The following examples disclose specific embodiments of recombinant NMDA antibodies and methods of use thereof. These examples should be construed to encompass any and all variations that become evident as a result of the teaching provided herein.

Example 1: Materials and Methods

A. Cell Culture, Hybridoma Generation and Antibody Purification

Peripheral blood was obtained from an 18 year-old female who presented to the Children's Hospital of Philadelphia with emotional lability, paranoia, and temporal lobe seizures, with anti-GluN1 IgG detectable in her CSF. Peripheral blood mononuclear cells (PBMCs) were processed and cryopreserved as previously described.[10] We performed a cell fusion following standard methods.[10]

Briefly, PBMCs expressing the CD27 antigen were isolated with anti-CD27 magnetic beads (Miltenyi Biotec, Auburn, Calif.) and cultured for 8 days in the presence of human UltraCD40L (Multimeric Biotherapeutics, San Diego, Calif.) in advanced RPMI supplemented with 10% fetal bovine serum (FBS), cytokines and other growth factors. On day 8, cultured cells were electrofused to the B5-6T cell line and selected with HAT. Hybridoma supernatants were screened for secretion of IgGs that bind GluN1 by whole cell ELISA (with GluN1-GluN2a transfected HEK293T cells). Positive clones were subcloned 3 times to isolate stable hybridomas expressing GluN1-reactive IgGs. The hybridomas were cultured in RPMI with ULTRA LOW IgG Fetal Bovine Serum US origin (Thermo Fisher Scientific, Waltham, Mass.) and IgGs were purified from the supernatants using Protein G Sepharose columns (GE Healthcare Life Sciences, Pittsburgh, Pa.). MAb concentrations were measured with a NANODROP spectrophotometer (NanoDrop Technologies, Wilmington, Del.). HEK293T cells were cultured in DMEM 10% fetal calf serum with pen/strep/glutamine.

B. DNA and Antibody Reagents for Immunocytochemistry

For HEK293T cell transfections, we used the previously described plasmids encoding GluN1a, GluN2a, AMPA receptor type 1 (GluA1), AMPA receptor type 2 (GluA2), GluN1a with the amino terminal residues 26-382 deleted (GluN1a-ATD) and GluN1a containing a N368Q mutation (GluN1-N368Q).[3,7,11] The HEK293T-ATD cell line contains the amino terminal domain of GluN1a, fused to a MYC tag, TEV protease site, and the PDGF receptor transmembrane domain, and expressed in HEK293T cells by retroviral transduction using pBabePuro vector (See Example 5).[7,12,44]

For detection of GluN1, we used the clone 54.1 mAb, which binds the extracellular loop between transmembrane regions III & IV (Millipore Cat #MAB363 RRID: AB94946), and a rabbit mAb that binds the GluN1 C terminal domain (Millipore Cat #AB9864 RRID: AB2112158). For detection of GluR1 or GluR2, we used rabbit anti-GluR1 (Millipore Cat #AB1504 RRID: AB11212863) or rabbit anti-GluR2 (Millipore Cat #07-598 RRID:AB11213931) polyclonal antibodies, followed by secondary anti-rabbit IgG conjugated to ALEXA 488 (Thermo Fisher Scientific Cat #A-11034 also A11034 RRID: AB2576217). For rat neuron immunostaining, we used the anti-MAP2 murine mAb (Thermo Fisher Scientific Cat #13-1500 RRID:AB2533001), mouse anti-GluN1 (BD Biosciences Cat #556308 RRID:AB396353) or mouse anti-PSD95 (BD Biosciences Cat #610496 RRID: AB397862) and rabbit anti-GluN1 (Millipore Cat #AB9864 RRID: AB2112158). For internalization testing, mAbs were conjugated to CYPHERSE NHS Ester dye (GE Healthcare Life Sciences) following the manufacturer's instructions. Cells were seeded on coverslips and maintained in PBS at 37° C. in a humidified $CO_2$ incubator, and visualized at the indicated time points by confocal microscopy.

C. Whole Cell ELISA

To identify IgGs immunoreactive with GluN1, we used a whole-cell ELISA.[13] We plated $5\times10^5$ HEK293T cells onto wells of 6 cm plates in 4 ml DMEM containing 10% FBS and 1% penicillin/streptomycin. One day later, we transfected 1 µg each of the GluN1a plasmids using X-TREME-GENE 9 DNA transfection reagent (Roche, Basel, Switzerland). Medium was supplemented with 100 µmol/L MK-801 (SigmaAldrich, St. Louis, Mo.). The next day, we fed the cells with 4 mL fresh medium with MK-801. 48 h after transfection, we trypsinized the cells, washed them with PBS, and plated them in Corning 96 Well EIA/RIA clear flat bottom polystyrene high bind microplates (Corning, N.Y.) at $1\times10^5$ cells/well in 100 µL PBS. The plates were spun at 350 g for 10 min, supernatants were discarded, and the plates were dried at 37° C. for 20 min, then fixed with 100 µL per well of 2% paraformaldehyde in PBS for 15 min at room temp. The plates were washed three times with PBS pH 7.8 containing 0.05% Tween-20 (PBST), then blocked with 5% bovine serum albumin (BSA) in PBST (PBST:BSA) overnight at 4° C., followed by 3 washes with PBST. Patient samples or purified mAbs were diluted in PBST:BSA and applied to the plates 1 h at 37° C. (hybridoma supernatants were used without dilution). As positive and negative controls, we used an anti-NMDAR1 rabbit mAb at 1:100 dilution (Millipore Cat #AB9864 RRID:AB2112158) and an isotype control human mAb (6A).[14] After 1 h, the plates were washed 3× with PBST. As secondary antibodies, we used an HRP-conjugated anti-human IgG mAb (1:1500) (SouthernBiotech, Cat #4030-05, RRID: AB2687483) and an HRP-conjugated, polyclonal goat anti-rabbit IgG (1:1500) Southern Biotech, Cat #9040-05, RRID: AB2687484). OPD was used as substrate and optical density (OD) was measured at 490 nm using SYNERGY II plate reader (Biotek Instruments, Winooski, VT).

To determine whether 5F5 and 2G6 mAbs could simultaneously bind to GluN1, we tested binding to the HEK293T-ATD cell line ($10^5$ cells/well) in the Whole Cell ELISA and used a luminescent detection method. We biotinylated the 5F5 and 2G6 or 5F5 using the EZLINK™ Hydrazide-Biotin kit (Thermo Fisher), then generated dilution series of 2G6 or 5F5 (50 µg/mL to 0.2 µg/mL) and added to them the plate for 1 h at 37° C., followed by three washes with PBST. We then added the biotinylated 5F5 or 2G6 mAbs at 5 µg/mL, or PBS, and incubated for 1 h at 37° C. followed by three washes with PBST. The PIERCE Streptavidin Poly-HRP substrate (Thermo Fisher) was added at 1:2000 dilution and incubated for 1 h at 37° C. This was followed by SUPERSIGNAL ELISA Femto Substrate, (1:1 ratio) (Thermo Fisher) and relative luminescence values were measured using the SYNERGY II plate reader. Duplicate binding curves were plotted and the linear portions were used for analysis using Excel.

D. Immunofluorescence Studies with Cultured Cells

HEK293T cells were cultured and transfected with plasmids expressing GluN1a, GluN2a, GluR1, GluR2, GluN1-ATD (deleted amino acids 26-382), and GluN1-N368Q as described above, except that $10^4$ cells/well were cultured on round CORNING™ BIOCOAT™ 12 mm #1 German Glass Coverslips in 24 well plates.[7] 48 h after transfection, cells were stained as described.[3] The cells were fixed in PBS with 4% paraformaldehyde for 10 min at room temperature, then washed with PBS, treated with 0.3% TritonX-100 in PBS for 10 min at room temp, and washed again with PBST. The cells were blocked with 10% Goat serum+1% BSA in PBS (PBS+G+B) for 1 h at 37° C., then washed with PBST. Cells were incubated with mAbs (5F5, 2G6, or an isotype control mAb 8E1 or 6A) at a concentration of 5 µg/mL in PBS+G+B for 1 h at room temp. ANRE patient CSF were used at 1:100 dilutions. GluN1 expression was detected with the commercial antibodies noted above. After 1 h, cells were washed twice with PBST and incubated with secondary antibodies in PBS+G+B for 1 h, 1:1000 ALEXA 488 goat anti-mouse (Thermo Fisher Scientific Cat #A-11029 RRID: AB2534088), 1:1000 ALEXA 568 goat anti-human (A21090, Thermo Fisher) or 1:200 goat anti-rabbit ALEXA 488 (Thermo Fisher Scientific Cat #A-11034 also A11034 RRID:AB2576217). Cells were washed once with PBS followed by dH2O and then their coverslips were mounted with PROLONG GOLD Antifade reagent with DAPI (Thermo Fisher) and imaged with a C2+ Nikon confocal microscope with 63×/1.3 NA oil objective; images were analyzed with ImageJ software (https://imagej.nih.gov/ij/).

E. High-Throughput Sequencing of VH—Encoding Genes and Phylogenetic Analyses of the 5F5 AND 2G6 MAb Lineages Total RNA was isolated from a subset of the CD27+ selected peripheral blood mononuclear cells that had undergone in vitro culture prior to cell fusion (see above). 500 ng RNA was used for reverse transcription according to the manufacturer's instructions using SUPER-SCRIPT III Enzyme (Life Technologies) and oligo-dT primer, following standard protocols.[15] After cDNA construction, VH transcripts were PCR-amplified using FASTSTART Taq DNA polymerase (Sigma-Aldrich) under the following conditions: 2 min at 95° C.; 4 cycles of 92° C. for 1 min, 50° C. for 1 min, 72° C. for 1 min; 4 cycles of 92° C. for 1 min, 55° C. for 1 min, 72° C. for 1 min; 24 cycles of 92° C. for 1 min, 63° C. for 1 min, 72° C. for 1 min; 72° C. for 7 min; held at 4° C. The final sequencing library was sequenced using the ILLUMINA MISEQ platform. Raw MISEQ sequence reads were stitched using PEAR,[16] and then quality filtered and annotated using MiXCR.[17] Productive, full-length VH sequences with IGHV3-30 gene usage were grouped into 5F5- and 2G6-lineages by clustering on the CDRH3 nucleotide sequences of 5F5 and 2G6 mAbs at 80% identity, respectively. Sequences in each lineage were further clustered on the full-length nucleotide sequence at 98% identity to reduce PCR and sequencing error, and sequences with only 1 read were removed. The resulting sequences were aligned by MAFFT,[18] and the maximum likelihood phylogenetic trees analysis was performed using RAxML.[19]

F. Primary Rat Neuron And Brain Immunostaining

Primary rat or murine neurons were obtained from Thermo Fisher (A10841-01) or from the Cellular Neuroscience Core Facility at the Children's Hospital of Pennsylvania. Cells were grown in Neurobasal Medium supplemented with 200 mmol/L GLUTAMAX and 2% B-27 Supplement (Thermo Fisher). A total of $10^5$ cells/well were plated in 24-well plate containing coverslips and kept at 37° C. for culture. After 24 h, half of the medium in each well was replaced with fresh medium and cells were grown for 14 days. The cells were then washed, fixed, and blocked as mentioned above. Cells were then incubated with 5 µg/mL 5F5, 2G6, or CSF (1:100) in PBS+G+B. After 1 h at 37° C., cells were washed, incubated with fluorescent secondary antibodies (BD Biosciences Cat #556308 RRID:AB396353) or mouse anti-PSD95 (BD Biosciences Cat #610496 RRID: AB397862) and rabbit anti-GluN1 (Millipore Cat #AB9864 RRID: AB2112158). In the experiments with the mAbs labeled with CYPHER 5E dye, neurons were incubated with additional 10 mmol/L glycine, 30 mmol/L glutamate, with or without either MK-801 (50 µm) or AP5 (100 µm) for 15 min Labeled mAbs were then added, and after 45 min the neurons were fixed and processed as noted above. Images were acquired using a Carl Zeiss LSM 510 UV META inverted confocal microscope with a PLAN-APO 60× oil immersion lens at room temperature and processed using AIM 4.2 SP1 software (Zeiss Microimaging, Thornwood, N.Y.).

Adult mouse brains were fixed for 24 h in 4% paraformaldehyde, then stored in PBS. Brains were embedded in a 4% agarose block, sectioned using a vibratome (20 µm sections), and collected in anti-freeze (30% ethylene glycol, 30% glycerol, 30% MilliQ water, 10% 10× PBS) as floating sections, washed 5× in PBST, and blocked with 5% normal goat serum. Before staining, mouse sections were incubated with Vector M.O.M. diluent prepared in M.O.M mouse IgG Blocking Reagent (Vector Laboratories cat #BMK-2202), then incubated overnight with patient CSF (1:5) or mAb (100 µg/mL) and mouse-anti GluN1 (BD Biosciences cat #556308) prepared in Blocking Reagent. Sections were washed five times with Blocking Reagent and incubated with secondary antibodies (goat anti-human IgG ALEXA FLUOR 488 and goat anti-mouse 568) prepared in Blocking Reagent. Sections were washed four times in PBST, once with PBS, and then mounted on slides for visualization on a LEICA DMi8 confocal microscope.

G. Effect of NMDAR Antibodies on Mouse Wheel Running Activity

Female Swiss Webster mice 6-8 weeks of age (Taconic Biosciences; Germantown, N.Y.) were housed at the AAALAC-certified animal facility at the Lankenau Institute for Medical Research. Experiments were approved by the Main Line Health Institutional Animal Care and Use Committee (IACUC). Mice were housed in pairs, in cages fitted with running wheels connected to a microchip and a magnetic wheel revolution counter (Mini-Mitter Co. Inc., Bend, Oreg.). They were acclimated to the cages 10-14 days, during which time their baseline daily wheel revolutions were recorded. The mice then received (i.p) injections of 1.5 mg/kg Lipopolysaccharide (Sigma-Aldrich). Three hours later, pairs of mice each received i.p injections of one or two human IgG, either 500 µg 6A, 500 µg 5F5, 500 µg 2G6, or 250 µg 5F5 with 250 µg 2G6. Twenty mice were tested in each group (ten cages), except for 10 mice tested in the 6A group (5 cages).

The wheel running activity was counted daily following the injection for up to 25 days. The LPS significantly reduced mouse activity for ~3 days. Therefore, we compared the average daily revolutions from the 4 days prior to the LPS injection with the new steady state level following recovery from the LPS (also averaged over a 4 day period). Statistical significance was estimated by one-way ANOVA (GraphPad). Groups of four mice (two per cage) were also tested for voluntary wheel running activity following i.p. administration of low doses of MK-801 (100 µg/kg or 50 µg/kg), 21 comparing the 4 day period prior to injection with the 4 day period afterwards.

H. Assessment of MAb Binding to Murine Hippocampus Following Intravenous Injection To assess binding of the 5F5 and 2G6 mAbs to hippocampal tissues in vivo, Swiss Webster mice aged 6-8 weeks were injected i.p with LPS (1.5 mg/kg) and 15 min later, i.v. with 250 µg 5F5 and 250 µg 2G6 combined, or 500 µg 6A. One hour later, mice were euthanized with CO2. The hippocampal and cerebellar tissues were dissected, embedded in freezing media (Tissue Tek O.C.T, Sakura Finetek, Torrance, Calif.), and frozen in liquid N2. Seven µm sections were cut with Microm HM505E microtome. Slides were fixed with cold acetone (Fisher Scientific, cat #A18P-4) for 10 min at 4° C. and then stored at 20° C. For staining, slides were washed with PBS then blocked with 1% PBS-BSA, 5% goat serum for 2 h at room temperature. ALEXA FLUOR 555 Goat antihuman IgG (Invitrogen, Eugene, Oreg., cat #A21433) at 10 lg/mL was added, incubated for 1 h at room temperature. Slides were washed and mounted with PROLONG GOLD Antifade reagent with DAPI (Thermo Fisher) and imaged with a C2+ Nikon confocal microscope with 63×1.3NA lenses. The confocal microscope setting was optimized according to the signal intensity of the negative control mAb (6A). The images were analyzed using Image J software (http://imagej.nih.gov/ij).

I. Methods to Prevent Bias

Cell binding experiments were repeated multiple times using duplicate and triplicate samples. Mice were randomly selected to receive antibody and drug treatments. DNA sequence analysis was performed in two laboratories. Neuron staining and internalization studies were performed in two laboratories with neurons from different sources.

Example 2: Isolation of ANRE Patient-Derived Monoclonal Antibodies that are Immunoreactive with Glun1

Figure 2:
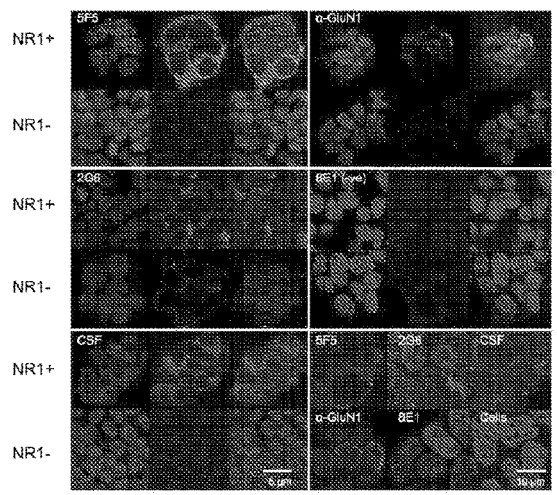
FIG. 2 shows fluorescent immunostaining by the 5F5 and 2G6 mAbs of HEK293T cells expressing GluN1/2a. HEK293T cells with (NR1+) or without (NR1−) transient expression of GluN1 and GluN2a were immunostained with SFS (top left panel), 2G6 (middle left panel), ANRE patient CSF (bottom left panel), murine anti-GluN1 (top right panel), or 8E1 non-specific control IgG (middle right panel), followed by the corresponding anti-human or anti-mouse Alexa 488 secondary antibody (green) and nuclear DAPI stain (blue), and visualized by confocal microscopy. For each antibody are shown, from left to right: DAPI, mAb-only, and merged images. Scale bar=5 μm. The bottom right panel shows higher magnification merged images of 5F5, 2G6, ANRE CSF, anti-GluN1, 8E1, as well as a control sample not exposed to human antibody (Cells). 5F5, 2G6, and patient CSF bind preferentially to GluN1/GluN2a expressing cells. Scale bar=10 μm.
Figure 3:
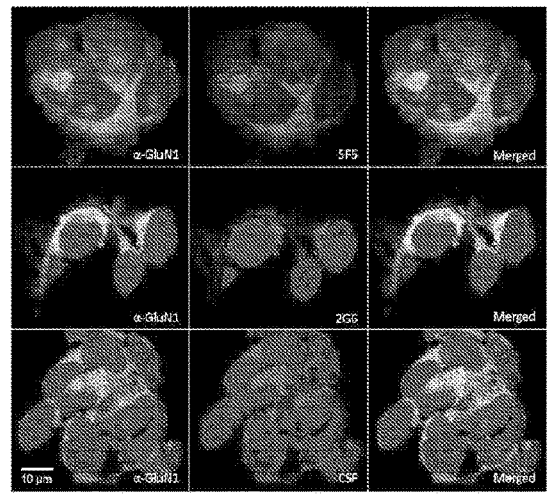
FIG. 3 shows colocalization of the 5F5 and 2G6 human mAbs with a murine anti-GluN1 mAb on HEK293T cells expressing GluN1/GluN2a. HEK 293T cells expressing GluN1 and GluN2a were co-immunostained with either 5F5, 2G6 or CSF (red) and the murine anti-GluN1 antibody (green). In each row, from left to right are shown cells stained with the anti-GluN1 mAb, human mAb or CSF, and merged images. Nuclei were visualized by DAPI staining. Colocalization of the GluN1 antigens recognized by the mAbs is demonstrated by the yellow fluorescence in the merged images. Scale bar=10 μm.

We obtained peripheral mononuclear cells from an 18 year-old female who presented with emotional lability, paranoia, and temporal lobe seizures, without an ovarian teratoma, and was found to have anti-NMDAR IgG antibodies in her CSF. We used standard hybridoma methods to obtain two IgG mAbs reactive with the NMDAR expressing 293T cells.[7,14] Following purification, we tested 5F5 and 2G6 for binding to N1a/N2b-transfected HEK293T by ELISA, confirming that binding depended on the expression of N1a/N2b (FIG. 1). We further assessed 5F5 and 2G6 binding to N1a/N2b-transfected HEK293T cells by immunofluorescence microscopy, in comparison to ANRE patient CSF, a murine anti-GluN1 mAb, and a control human IgG (8E1) (FIG. 2). 5F5 and 2G6 both showed diffuse, bright, punctate staining in the N1a/N2b-transfected cells only, whereas 8E1 did not stain. The ANRE patient CSF stained the cells in a similar, but more diffuse pattern. We co-stained these cells with the commercial anti-GluN1 mAb and either 5F5, 2G6, or ANRE patient CSF (FIG. 3). The two mAbs and the patient CSF (red) both colocalized substantially with the commercial mAb (green).

Figure 5:
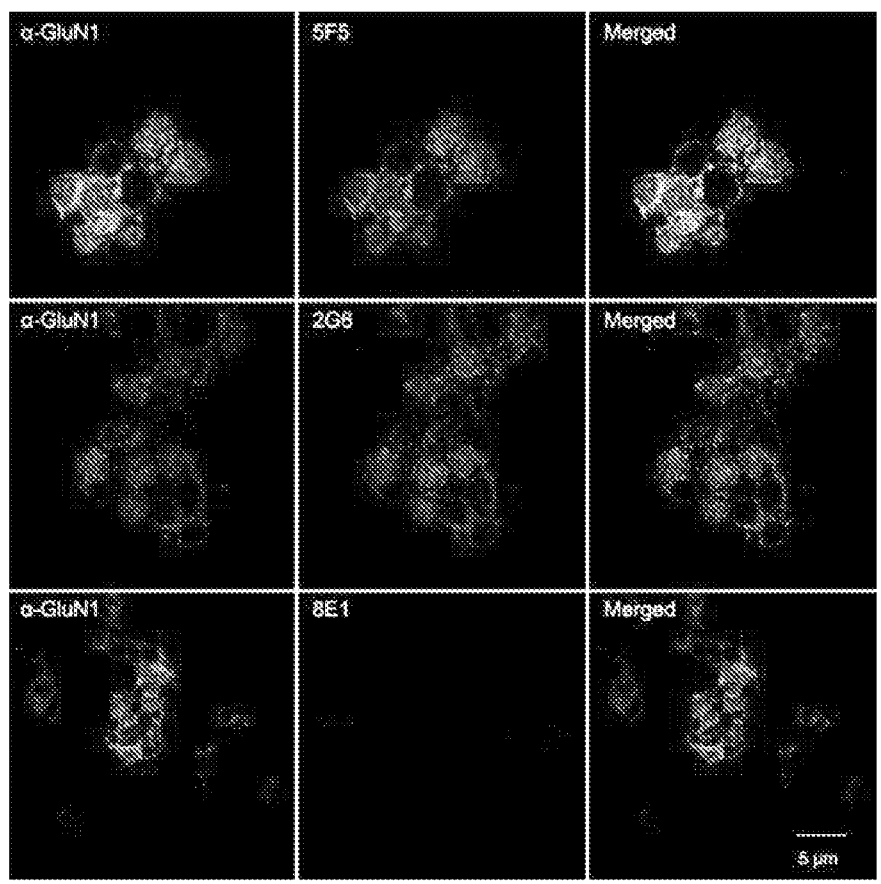
FIG. 5 shows binding of the 5F5 and 2G6 mAbs to the GluN1 Amino Terminal Domain (ATD). The GluN1-ATD, fused to the PDGF receptor transmembrane domain, was stably expressed on the surface of HEK 293T cells. Cells were immunostained with a commercial anti-GluN1 antibody (green), followed by 5F5, 2G6, or the 8E1 negative control mAb (red). Both 5F5, 2C6 mAbs bind to the GluN1 ATD, whereas the 8E1 does not. Scale bar=5 μm.

ANRE patient IgGs bind a conformational epitope on the GluN1 ATD.[1,7] We assessed mAb binding to two GluN1 mutants known to affect pathogenic IgG binding: an almost complete ATD deletion (aa 1-382) and the GluN1-N368Q mutant, and tested binding of 5F5, 2G6, and patient CSF (FIGS. 4A-4B, respectively). We saw no binding to either of the altered GluN1 proteins, whereas a C-terminal specific antibody did bind. We next tested binding to an ATD fusion protein SEQ ID NO: 8, which contains the 541 amino acid ATD fused to the transmembrane domain of the PDGF receptor in HEK293T cells (FIG. 5) described in Example 5. Both the 5F5 and 2G6 mAbs bound the ATD fusion, whereas the 8E1 negative control did not. Furthermore, none of the mAbs bound to the AMPA class of ionotropic NMDA receptors, GluA1 or GluA222 (data not shown).

A. DNA Sequence and Competitive Binding Analysis of the 5F5 and 2G6 mAbs

We next assessed the relatedness of the 5F5 and 2G6 mAbs. We tested whether they bind overlapping epitopes on GluN1, using a competitive binding assay with HEK293T-ATD cells. We measured binding of one mAb, biotinylated, in the presence of increasing concentrations of the other (FIGS. 6A-6D).[23] In this assay, each mAb competed with itself for binding, but neither mAb interfered with the binding of the other, even at fivefold excess, indicating that themAbs bind to different sites on the GluN1 ATD.

We sequenced the Ig heavy chain (HC) and light chain (LC) variable regions of the 5F5 and 2G6 mAbs and analyzed them using the IMGT program[24] as shown below in Table 3.

TABLE 3

Assignment of the 5F5, 1D1 and 2G6 variable domain DNA sequences to their closest germline counterparts.

| | CDR3 | Heavy Chain | | | |
|---|---|---|---|---|---|
| Antibody | Length | VH gene | % identity | J-gene | D-gene |
| 5F5 | 21 | IGHV3-30*03, IGHV3-30*18, IGHV3-30-3*01 or IGHV3-30-5*01 | 90.97 | IGHJ4*02 | IGHD6-19*01 |
| 2G6 | 24 | IGHV3-30*03, IGHV3-30*18, IGHV3-30-3*01 or IGHV3-30-5*01 | 91.32 | IGHJ6*02 | GHD3-10*01 |
| 1D1 | 13 | IGHV3-30-3*01 | 90.62 | IGHJ4*02F | IGHD5-18*01 |

| | CDR3 | Light Chain | | |
|---|---|---|---|---|
| Antibody | Length | VH gene | % identity | J-gene |
| 5F5 | 11 | GLV1-47*01 | 93.68 | IGLJ2*01 or IGLJ3*01 |
| 2G6 | 10 | IGLV3-10*01 | 97.49 | IGLJ2*01 or IGLJ3*01 |
| 1D1 | 11 | IGLV3-10*01 | 94.39 | IGLJ2*01 or IGLJ3*01 |

Both 5F5 and 2G6 are IgG lambda mAbs, derived from the IGHV3-30 HC gene family, but with different light chain (LC) genes. They do not share any substantial similarity to each other in their variable domains, or to any of the previously published anti-NMDAR mAbs.[9] Both mAbs are heavily mutated. 5F5 and 2G6 showed somatic hypermutation rates of 9.0% and 8.7% in their heavy chain (HC) variable regions, and rates of 6.3% and 2.5% in their LC variable regions, respectively. Both have relatively long CDR-H3 (complementarity determining region 3): 21 amino acids in 5F5 and 24 amino acids in 2G6.

We performed a lineage analysis of the 5F5 and 2G6 mAbs by sequencing the Ig heavy chain repertoire of CD27+ B cells assessed at the time of cell fusion (i.e. following in vitro expansion) (See, e.g., FIG. 7 in reference 45). The patient's peripheral blood B-cell population was sampled, after in vitro proliferation and prior to cell fusion, and analyzed by Ig heavy chain sequencing. Lineages were defined to include sequences with >80% nucleotide sequence homology in CDRH3 domain and were analyzed by Clustal sequence analysis. The resulting phylogenetic analyses of the 5F5 and 2G6 mAb lineages (not shown) indicated sequences with identical CDRH3 domains, the fraction of total sequencing reads for each lineage member. We defined potential common mAb lineage members as those that used the IGHV3-30 gene and had >80% nucleotide sequence identity in their CDR-H3 regions. We excluded incomplete IgG sequence reads, as well as those with only one sequence read, leaving 271,896 reads, of which 3300 were related to 5F5 and 8934 to 2G6. Sequence alignment analysis reveals that the 5F5 and 2G6 mAbs arose from independent lineages, and that they are single members of two diverse families, including 9 (5F5) and 19 (2G6) relatives that have exactly the same CDR-H3 sequences, which is the predominant determinant of IgG binding specificity.[25] These data indicate that the 5F5 and 2G6 mAbs arose from independent B-cell clones that have undergone multiple rounds of antigen-driven somatic hypermutation.

Figure 8A:
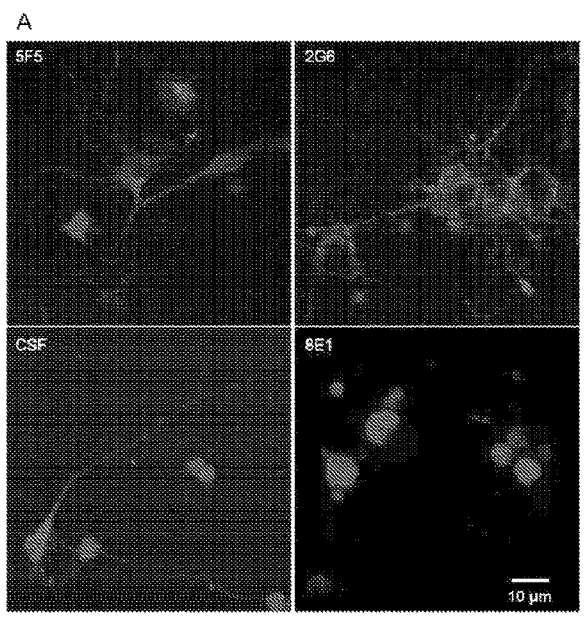
FIGS. 8A and 8B show that the 5F5 and 2G6 mAbs bind GluN1 on rat hippocampal neurons.
Figure 8B:
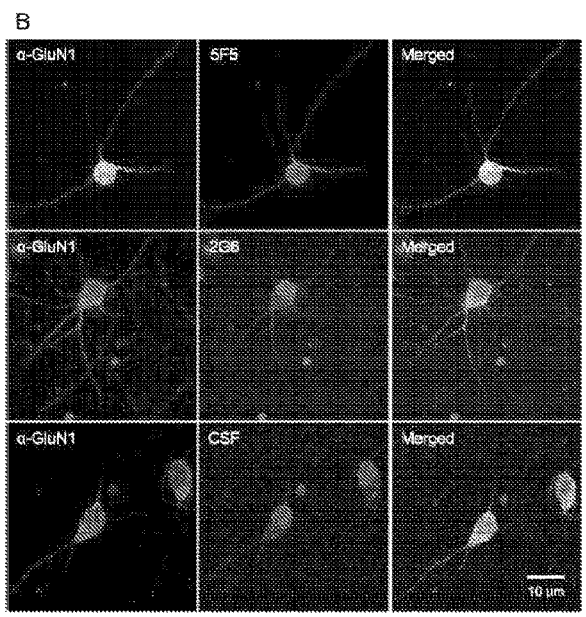
Figure 10A:
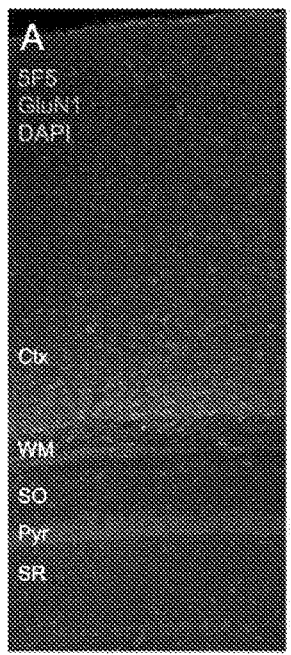
FIGS. 10A-10E show staining of murine brain with the 5F5 mAb. Murine hippocampal sections were immunostained with the 5F5 or 8E1 mAbs, or ANRE CSF (green), in combination with the commercial anti-GluN1 mAb (red), and DAPI.
Figure 10B:
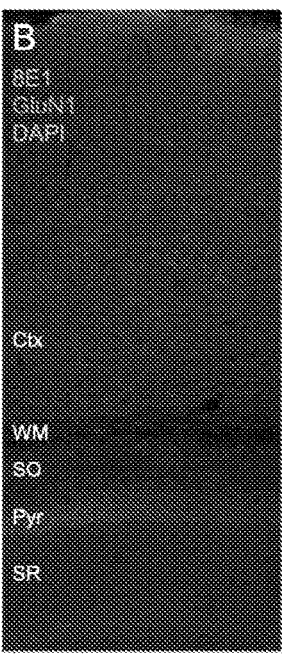
Figure 10C:
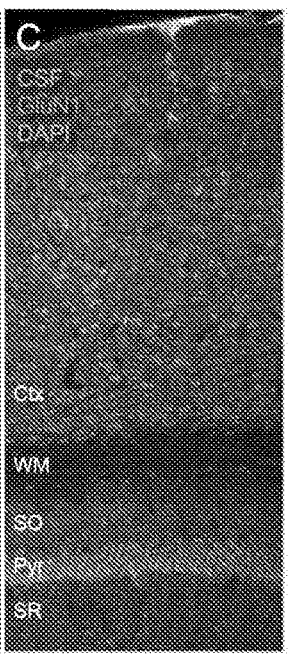
Figure 10D:
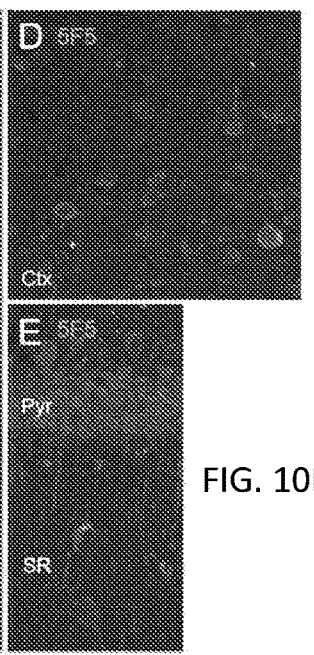
Figure 10E:
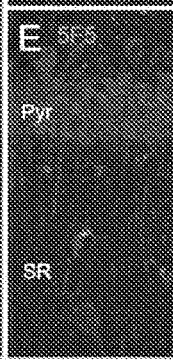

Example 3: Binding of the 5F5 and 2G6 Mabs to Primary Hippocampal Neurons and Murine Brain We next explored interaction of the mAbs with native NMDAR on primary tissues and in vivo. We tested binding of the 5F5 and 2G6 mAbs to cultured rat hippocampal neurons. Commercially obtained hippocampal neurons were cultured for 14 days and confirmed to express MAP2 and GluN1 (data not shown). We fixed the neurons and stained them with 5F5, 2G6, 8E1, or ANRE patient CSF (FIG. 8A). The CSF and the 5F5 and 2G6 mAbs bound to the neurons, whereas 8E1 did not. Coimmunostaining of the neurons indicated substantial overlap between the signals from the 5F5 and 2G6 mAbs and the murine anti-GluN1 mAb (FIG. 8B).

We next assessed the sites of 5F5 binding on murine primary hippocampal neurons that had not undergone fixation. Double-labelling images showed overlapping patterns with a rabbit GluN1 antibody, though to a lesser degree than IgG from ANRE patient CSF. In contrast to patient CSF, 5F5 immunoreactivity did not consistently colocalize with PSD-95, suggesting that it labels a subgroup of NMDAR that are primarily presynaptic or extrasynaptic (FIGS. 9A-9D). We next stained floating sections of murine cortex and hippocampus with the 5F5 mAb, CSF (FIGS. 10A-10E). 5F5 mAb colocalized with GluN1, particularly in the lower levels of the cortex. Less colocalization was noted in the hippocampus. No staining was noted for 8E1, but high levels of colocalization were found between patient IgG and GluN1. Taken together, the binding activities of the 5F5 and 2G6 mAbs are consistent with recognition of a subset of GluN1 in cultured neurons and in murine brain.

Figure 11A:
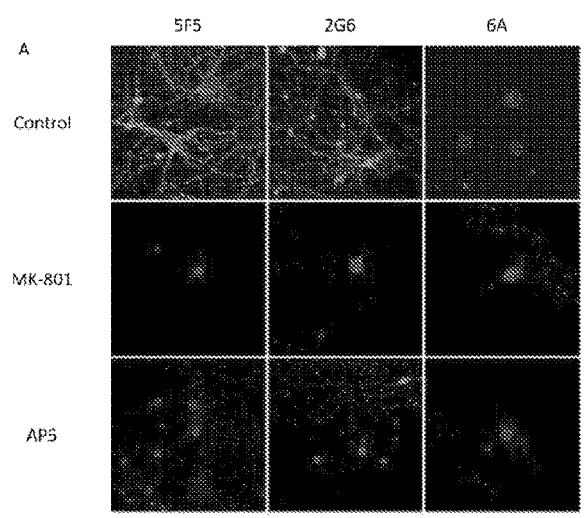
FIGS. 11A-11B show the internalization of the 5F5 and 2G6 mAbs by hippocampal neurons and the effects of MK-801 and AP5.
Figure 11B:
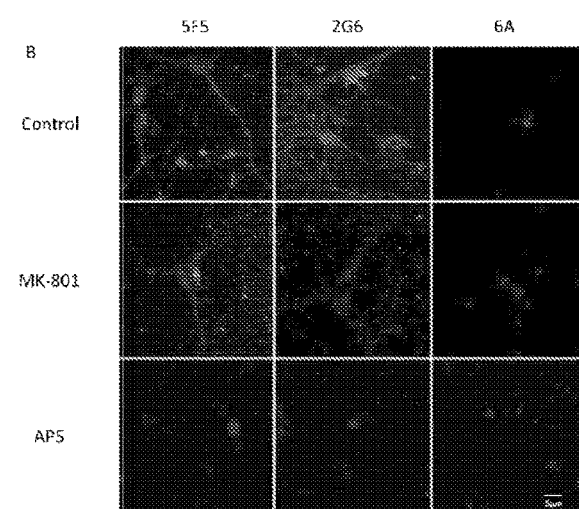

ANRE patient CSF reduces the surface density of NMDAR on cultured neurons.[3,4] We conjugated the 5F5, 2G6, and 6A mAbs with CypHer5E, a pH-sensitive dye that fluoresces upon internalization into acidic endosomes[26] and incubated the mAbs with cultured neurons (FIG. 11A). Cells were first exposed to supplemental glycine and glutamine, with or without the NMDAR inhibitors, MK-801 or AP5, for 15 min, and then exposed to the mAbs for 45 min. Both of the ANRE mAbs were internalized, whereas the control 6A mAb was not. Internalization was inhibited by treatment with the NMDAR inhibitors MK-801 and AP5 (FIG. 11A). Notably, MK-801 did not inhibit binding of the mAbs to the neurons, whereas AP5 did (FIG. 11B). This suggests that 5F5 and 2G6 binding alone is not sufficient for internalization, in the absence of receptor activation. Furthermore, it indicates that the closed configuration induced by AP5 masks the 5F5 and 2G6 binding epitopes.

Example 4: In Vivo Effects of the 5F5 and 2G6 Mabs

We measured the effects of the mAbs on mouse voluntary locomotor activity using the mouse wheel-running test, a relatively nonspecific study. We used it to assess whether global effects on behavior would be altered in a manner consistent with NMDAR hypofunction. In this crude assessment, following an injection of LPS, both mAbs increased the total daily running activity, which was sustained for several days and reflected the increase in activity experienced by mice receiving low-dose MK-801. This suggests that the antibodies identified here may down-regulate NMDAR activity, consistent with the primary state observed in ANRE.

We assessed the effects mAbs on mouse voluntary locomotor activity by measuring the distance traveled by mice on a running wheel.[27] Groups of 10 mice, housed in pairs, received i.p. injections of lipopolysaccharide (LPS), which induces blood brain barrier permeability.[28] Three hours later, they received i.p. injections of 6A, 5F5, 2G6, or 5F5 and 2G6 combined. Because the LPS causes approximately 3 days of hypo-activity, we compared pre and post-injection steady state activity levels and plotted the average change in the number of daily revolutions for the mice (FIG. 12A). The post-injection increase in wheel running activity for three of the mAb intervention groups were substantially higher than for the LPS alone group. Baseline activity did not differ among the groups, at approximately 14,000 revolutions per day (approximately 5 km). Daily wheel revolutions increased by 313 revolutions for the 6A control group (P=0.6), 1490 for 5F5 (P=0.026), 1448 for 2G6 (P=0.033), and 2051 for 5F5+2G6 (P=0.0005). To compare against the effects of specific NMDAR inhibition, we treated additional mice with low doses of MK-801 (FIG. 12B). Similar to the ANRE mAbs, MK-801 increased voluntary activity by over 2000 revolutions per day at both 2.5 μg and 1.25 μg/kg doses, compared to untreated mice (P<0.0001).

Figure 13:
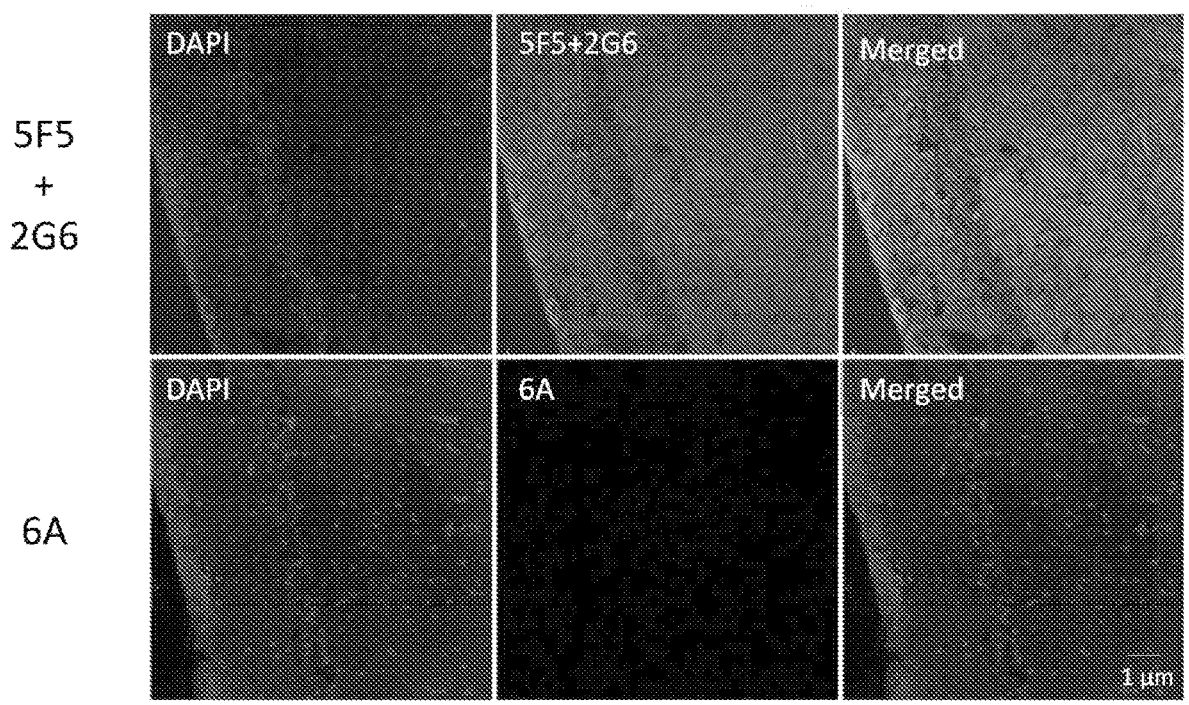
FIG. 13 shows the interaction of the 5F5 and 2G6 mAbs with murine hippocampus following intravenous injection. Mice received a dose of LPS, followed 15 min later by either the 6A mAb or a combination of 5F5 and 2G6. One hour later, hippocampal frozen sections were prepared and stained for human IgG (red). Top row, 5F5 and 2G6. Bottom row, 6A. Scale bar=1 μm.
Figure 14:
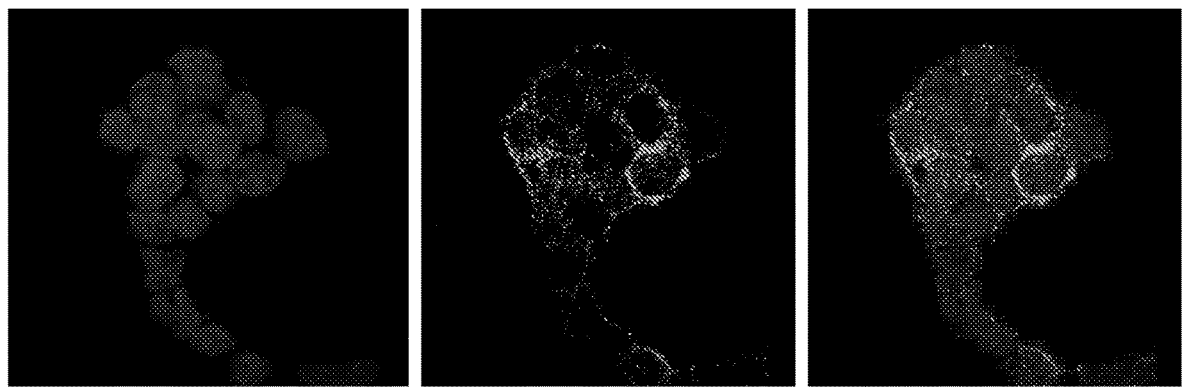
FIG. 14 shows immunostaining of the HEK293T-ATD cell line with mAb 1D1 specifically immunofluorescence imaging of the NR1 ATD fusion protein on 293T-ATD cells. 293T-ATD cells were immunostained with a murine anti-NR1 mAb (red color, middle panel) and the nuclei were stained with DAPI (blue color, left panel). A merged image is also shown (right panel). Cells were visualized by confocal microscopy.
Figure 15A:
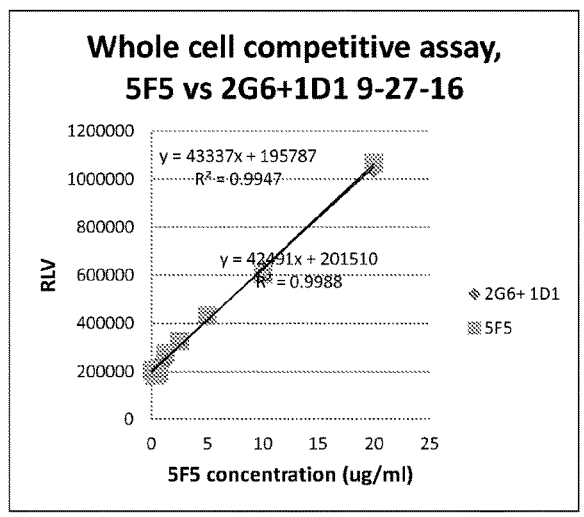
FIG. 15A is a graph showing the results of a whole cell competitive assay comparing mAb 5F5 vs. 2G6 and 1D1.
Figure 15B:
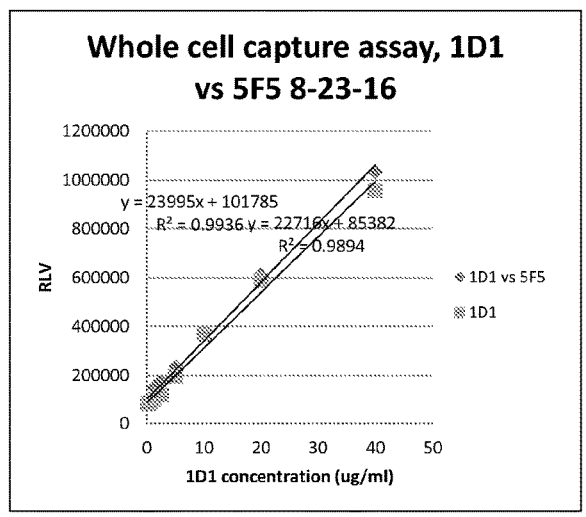
FIG. 15B is a graph showing the results of a whole cell capture assay comparing mAb 1D1 vs. 5F5 and 1D1.
Figure 17:
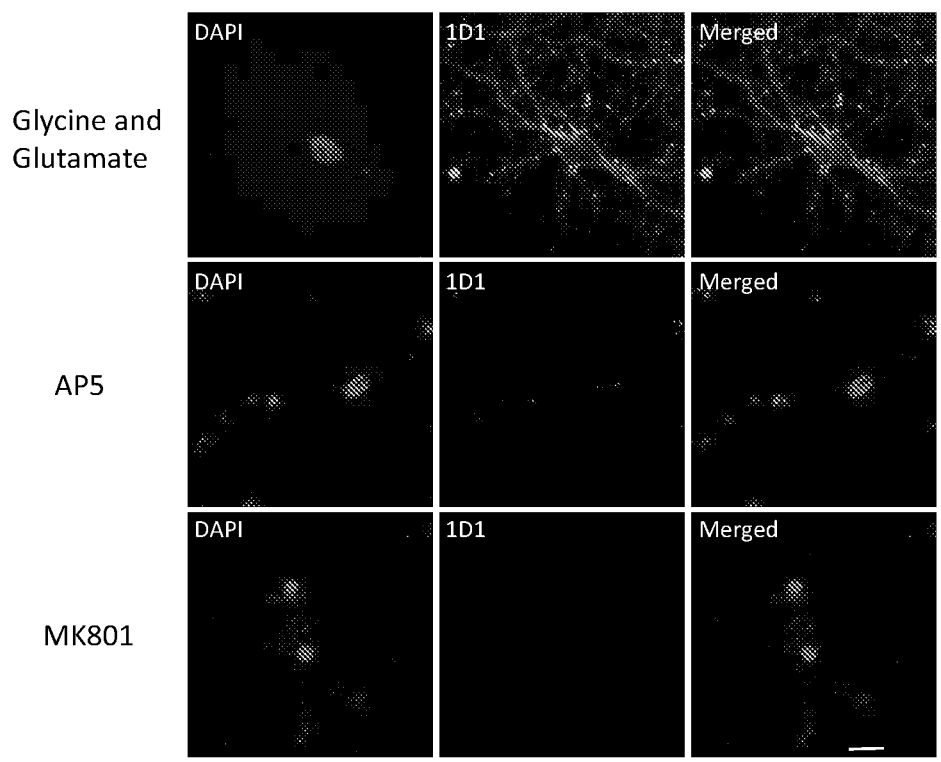
FIG. 17 shows internalization of CYPHER5E™ fluorescent dye labeled 1D1 by hippocampal neurons in vitro in the presence of glycine and glutamate. Left column, DAPI stained nuclei (blue). Middle column, 1D1 CYPHER5E™ (maroon). Right column, merged images. Middle three panels, cells were pre-treated with AP5. Bottom panels, cells pre-treated with MK801. Maroon fluorescent signal is only seen in cells that internalize 1D1. Internalization is inhibited in cells treated with the NMDAR inhibitors (AP5 or MK801), indicating that 1D1 functionally interacts with NMDAR on hippocampal neurons.

We next assessed whether these biological effects correlated with the ability of the mAbs to bind hippocampal tissues following an intravenous injection. Groups of 6 mice received an LPS injection, followed 15 min later by 6A or 5F5 with 2G6. One hour later, the mice were euthanized; frozen sections of the dissected hippocampi were stained for human IgG. Representative images are shown in FIG. 13. No human IgG was detected in the 6A-injected mice, whereas widespread human IgG staining was seen in the mice that received 5F5+2G6.

Example 5—Materials and Methods

Figure 18A:
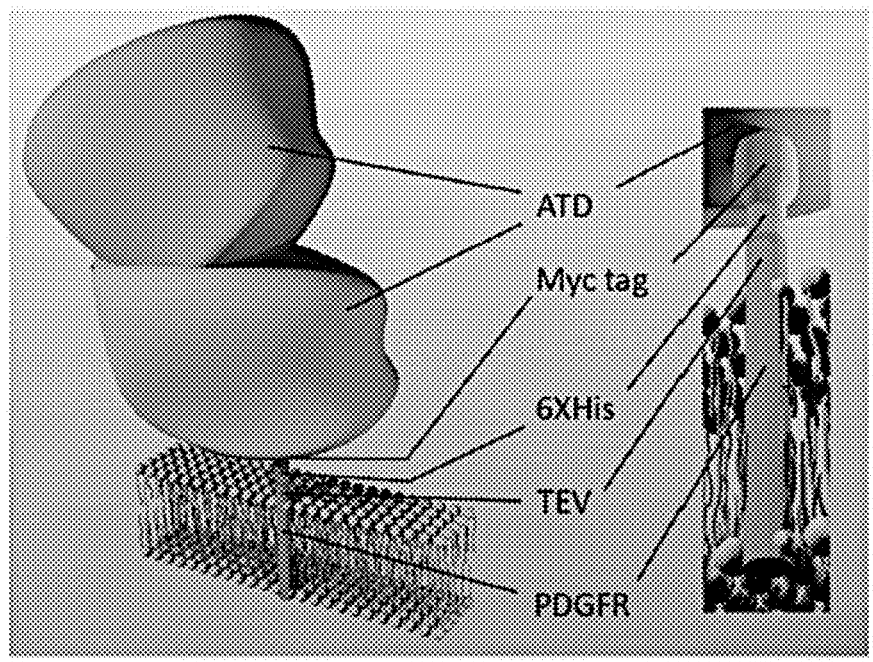
FIGS. 18A-18B are schematic graphs of the structure of the NR1 Amino Terminal Domain (ATD) fusion protein on 293 T cells. The ATD fusion protein consists of the entire 561 N-terminal amino acid extracellular domain, which includes the bi-lobed NR1 ATD, fused in sequence to the Myc tag, the 6×HIS tag, the Tobacco Etch Virus (TEV) protease site, and the platelet derived growth factor receptor (PDGFR) transmembrane domain. The DNA sequence of the ATD fusion gene has been deposited in Genbank Accession #MH460863 on Jun. 8, 2018 and has SEQ ID NO: 9. The amino acid sequence of the protein is SEQ ID NO: 8.
Figure 18B:
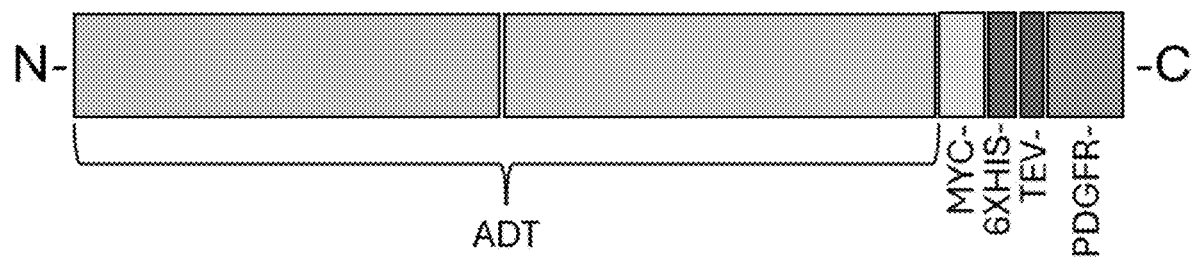

A. Human Subjects
CSF and patient sera were collected with full informed consent and protocols.
B. Expression of the ATD Fusion Protein in 293T Cells
We designed a recombinant gene SEQ ID NO: 9 encoding the entire 561 amino acids of the N-terminal extracellular domain of human GluN1 (NR1) (UniProtKB—Q05586), including the amino terminal domain (ATD), fused to the Myc epitope tag (EQKLISEEDL SEQ ID NO: 10), a 6×HIS tag, the Tobacco Etch Virus (TEV) protease cleavage site (ENLYFQGG SEQ ID NO:11), fused to the transmembrane domain of the human platelet-derived growth factor receptor (PDGFR)[12] (FIGS. 18A-18B). We deposited the fusion gene as Genbank Accession #MH460863[12,42].

The gene was synthesized and inserted into the retroviral vector, pBabe puro by Genscript (Piscataway, NJ)[43]. Amphotropic retroviruses were produced in 293T cells under puromycin selection following standard protocols, except that X-TREMEGENE 9 DNA Transfection Reagent was used (354,087, Roche, Germany), and the cells were cultured in Advanced DMEM, 1% IFS, penicillin/streptomycin (Invitrogen, Carlsbad, Calif.)[14]. The retroviral supernatant was used to transduce 293T cells ($2.5 \times 10^6$ in a 10 cm dish), with 4 µg/ml polybrene (TR1003G, Thermo Fisher Scientific, Waltham, Mass.), for 6 h. 48 h later, cells were selected with 1 µg/ml puromycin (P9620, Sigma-Aldrich, St. Louis, Mo.).

Figure 18C:
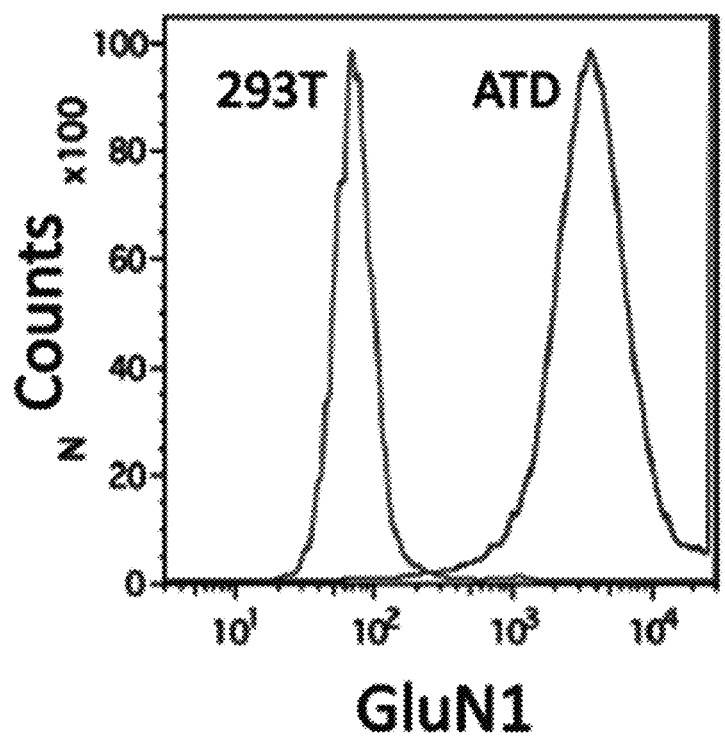
FIG. 18C is a graph showing the expression of the ATD fusion protein on the surface of 293T cells analyzed by flow cytometry with a commercial anti-GluN1 mAb.
Figure 18D:
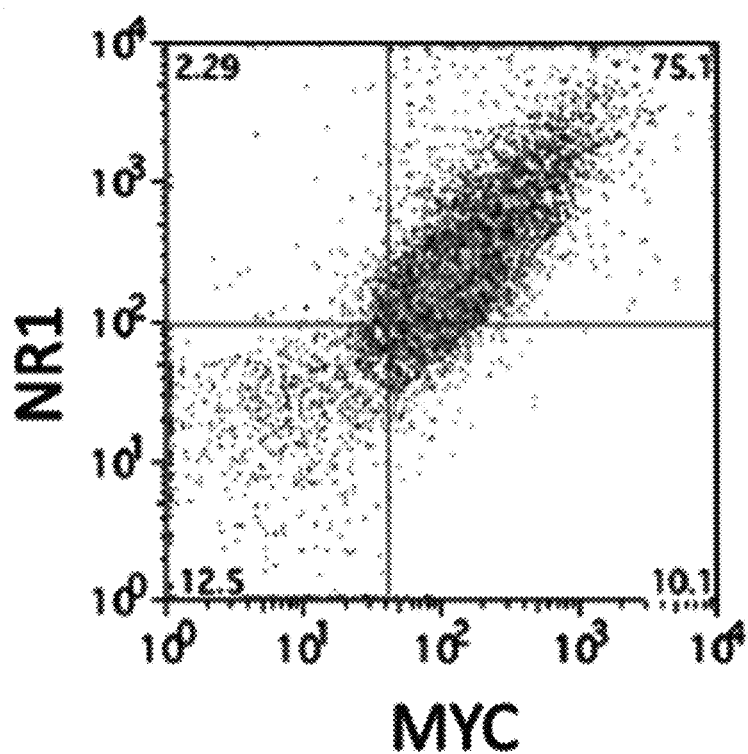
FIG. 18D is a graph showing the expression of the ATD fusion protein on the surface of 293T cells analyzed by flow cytometry with a commercial anti-GluN1 mAb with an anti-Myc tag mAb.
Figure 19A:
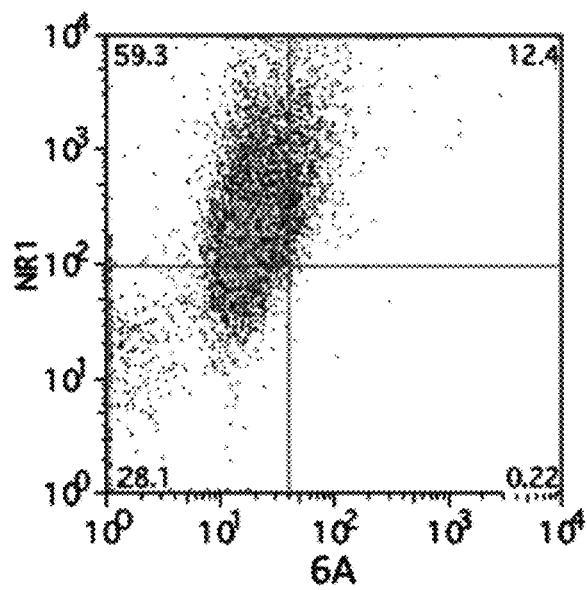
FIGS. 19A-19D show binding of human ANRE mAbs to 293T-ATD cells by flow cytometry. Cells were immunostained with a commercial anti-NR1 mAb and a human mAb and analyzed by flow cytometry. Human mAbs were either the isotype control IgG 6A (FIG. 19A), or ANRE patient mAbs 5F5 (FIG. 19B), 2G6 (FIG. 19C), or 1D1 (FIG. 19D).
Figure 19B:
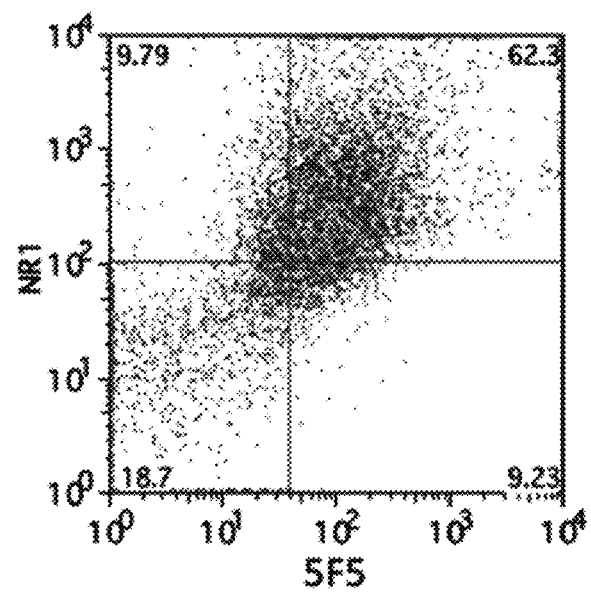
Figure 19C:
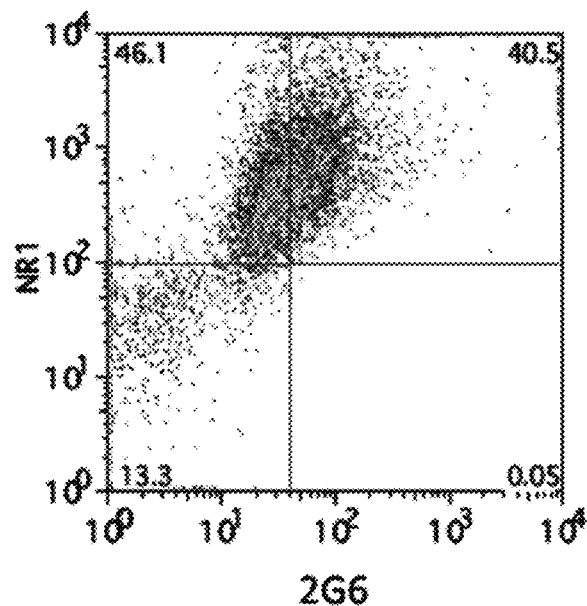
Figure 19D:
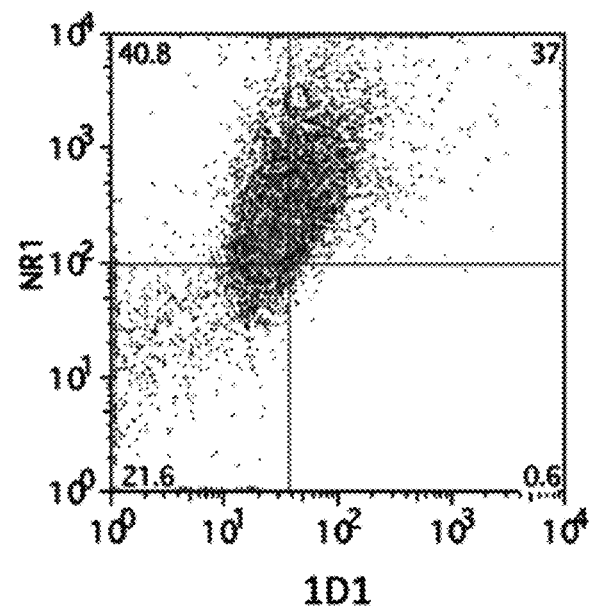

One week later, expressing cells were isolated by FACS staining with the murine anti-NR1 APC mAb (orb149996, Biorbyt, San Francisco, CA) on the BD FACSCANTO II (Becton Dickson, Franklin Lakes, NJ). A stable, homogeneous population of cells (293T-ATD) was isolated by flow cytometry (FACS) over four rounds of selection using a commercial murine NR1 mAb, over four weeks, resulting in the cell population 293T-ATD (FIG. 18C).

C. Flow Cytometry, Facs, and Immunofluorescence Studies

To assess antibody binding to 293T-ATD cells by flow cytometry, cells were harvested using 0.05% trypsin, washed, and resuspended at $1 \times 10^6$ cells/ml in PBS-1% BSA (A7030, Sigma-Aldrich). Primary antibodies included the BIOORBYT APC-labeled NR1 mAb at 10 µg/mL, an ALEXA FLUOR 488 labeled Myc tag mAb at 2 µg/mL (16-308, Millipore, Billerica, MA) three human IgG mAbs (5 µg/mL) isolated from a patient with ANRE (5F5, 2G6, 1D1) and the 6A isotype control mAb[14]. As a secondary antibody for the human mAbs, we used a FITC-conjugated F(ab')2 goat anti-human IgG (109-096-008, Jackson ImmunoResearch, West Grove, Pa.). Cells were assayed with a BD FACSCANTO II (Becton Dickson, Franklin Lakes, N.J.). Data were analyzed using FLOWJO 8.8.7. Software (Tree Star, Ashland, OR).

For immunofluorescence studies, 293T-ATD cells were plated at $5 \times 10^4$ cells/well on round CORNING™ BIOCOAT™ 12 mm #1 German Glass Coverslips (354,087, Corning, NY) in 24 well plates. 24 h later, the cells were fixed with 4% paraformaldehyde in PBS for 10 min at room temperature, washed with PBS 0.05% Tween-20 (PBST), blocked with 10% Goat serum (Invitrogen)+1% BSA in PBS (PBS+G+B) for 1 h at 37° C., and then washed with PBST.

Cells were incubated for one hour at room temp in PBS+G+B with one or more of the following added: a murine anti-NR1 APC mAb (orb149996, Biorbyt, San Francisco, Calif.), an ALEXA FLUOR 488 conjugated anti-Myc-tag-specific mAb (16-308, Millipore) (1:250 dilution), ANRE patient or normal human CSF (1:20), ANRE patient or normal human sera (1:100), human mAbs, 5F5, 2G6, 1D1 or isotype human control mAb 8E1 (5 µg/ml). After one hour, cells were washed twice with PBST and incubated with the ALEXA 568 goat anti-human IgG, 1:1000 (A21090, Thermo Fisher), secondary antibody for the human CSF or mAbs in PBS+G+B for one hour, and then the cells were washed once with PBS and once with dH2O. Coverslips were mounted with PROLONG® GOLD Antifade reagent with DAPI (P36935, Thermo Fisher) and imaged with a C2+ Nikon confocal microscope with 63×/1.3 NA oil objective; images were analyzed with ImageJ software (https://imagej.nih.gov/ij/). All immunofluorescence studies were performed at least twice.

D. Mobilization of Membrane-Bound ATD with TEV Protease

The 293T-ATD cells were plated at $2 \times 10^5$ cells/well in 12 well plates. 24 h later, they were washed with PBS and then treated with 25 µg rTEV Protease (4469; R&D Systems, Minneapolis, MN) with XPERT Protease inhibitor cocktail solution (P3100-001; GenDEPOT, Barker, TX) in PBS for the indicated time period (10-40 min). The cells were pipetted up and down, transferred to Eppendorf tubes, and centrifuged at 3000 rpm for 10 min at 4° C. The supernatant was collected and immediately dialyzed against cold PBS overnight. The protein concentration was measured using NANODROP 1000 (Thermo Fisher) and protein was visualized on a Coomassie-stained SDS:PAGE gel.

E. ATD ELISAs

To analyze the time course of ATD mobilization by TEV, we performed a capture assay in which we coated Black 96-well immune plates (12-566-24, Thermo Fisher) with 5 µg/mL anti HIS tag antibody (ab18184, Abcam, Cambridge, MA) overnight, washed the plates 3 times with PBST, blocked with 5% inactivated fetal bovine serum and 3% Goat serum (Invitrogen) in PBST for 1 h at 37° C., then washed 3 times. ATD samples cleaved at the stated timepoints were added at 5 µg/mL and supernatant from uncleaved cells was added as negative control, followed by 1 h incubation at 37° C. The plates were washed three more times, and biotinylated human mAb 5F5 was added at 5 µg/mL (100 µl/well), and then incubated for 1 h at 37° C. After three additional PBST washes, Streptavidin-poly-HRP conjugate at 1:2000 (Thermo Fisher) was added and incubated for 1 h at 37° C. After three additional washes, SUPER SIGNAL ELISA Femto Substrate was used for detection (Thermo Fisher). Relative luminescence values were measured using the Biotek SYNERGY II Microplate reader (BioTek Instruments, Winooski, VT, USA). Microsoft Excel was used to process the data.

To test binding of human NR1 antibodies to plate-adherent ATD, we added 5 µg/mL Myc antibody (C3956, Sigma-Aldrich) (100 µl/well) to Black 96-well plates (12-566-24, Thermo Fisher) overnight, washed the plates 3 times with PBST, blocked with 5% inactivated fetal bovine serum and 3% Goat serum (Invitrogen) in PBST for 1 h at 37° C., washed 3 times, added 5 µg/mL ATD, and then incubated for 1 h at 37° C. and washed 3 more times. We added human mAbs, 5F5, 2G6, 1D1, and control isotype 6A at 5 µg/mL (100 µl/well), or 5 µg/mL anti-NR1 mAb (MAB 1586 RUHL, Millipore), in triplicate samples, and incubated for 1 h at 37° C. After three additional PBST washes, secondary antibodies were added, either an anti-human IgG HRP conjugate (9040-05 Southern Biotech, Birmingham, AL) or anti-mouse IgG HRP conjugate (1010-05, Southern Biotech), at 1:2000 and incubated for 1 h at 37° C., followed by 3 washes. Super Signal ELISA Femto Substrate was used for detection. Data was collected in the Biotek SYNERGY II Microplate reader and analyzed with Microsoft Excel.

To test binding of TEV-mobilized ATD to plate-adherent human IgG by ELISA, we first biotinylated the ATD using the EZ-LINK™ Sulfo-NHS-Biotin kit (21,326, Thermo Fisher). We added 5 µg/mL 5F5 (100 µl/well) to Black 96-well plates (12-566-24, Thermo Fisher), incubated overnight at room temp, washed the plates 3 times with PBST, blocked the wells with 2% non-fat milk in PBST for 1 h at 37° C., and again washed 3 times. We added triplicate serial dilutions of the biotinylated ATD (diluted in 50 µL PBS/well), and incubated for 1 h at 37° C. After three PBST washes, Streptavidin-poly-HRP conjugate at 1:2000 (Thermo Fisher) was added and incubated for 1 h at 37° C. SUPER SIGNAL ELISA Femto Substrate was used for detection. Data was collected in the Biotek SYNERGY II Microplate reader and analyzed with Microsoft Excel.

Example 6: Results of Example 5 Methods

Co-staining of the cell population with a Myc tag antibody and the NR1 mAb indicates that most of cells that express the Myc tag also express the NR1 ATD (data not shown). We tested binding of the three human monoclonal antibodies (mAbs), 5F5, 2G6, and 1D1 to the 293T-ATD cell population using flow cytometry, co-staining with the commercial anti-NR1 mAb (FIGS. 19A-19D). The ANRE patient mAbs all bound to the 293T-ATD cells to a greater extent than the 6A isotype control mAb, with double positive cells comprising 62.3% (5F5), 40.5% (2G6), and 37.0% (1D1), compared to 12.4% (6A control). Calculated as the proportion of NR1 positive cells bound by the mAbs, the 5F5 showed 90.5% binding; 2G6, 58.8%; 1G1, 53.7%; and 6A, 18.0% (Table 4).

TABLE 4

Percent GluN1-expressing cells bound by human ANRE mAbs

| Human MAbs | Percent GluN1 positive 293T-ATD cells bound |
| --- | --- |
| 5F5 | 90.5 |
| 2G6 | 58.8 |
| 1D1 | 53.7 |
| 6A | 18.0 |

Figure 20:
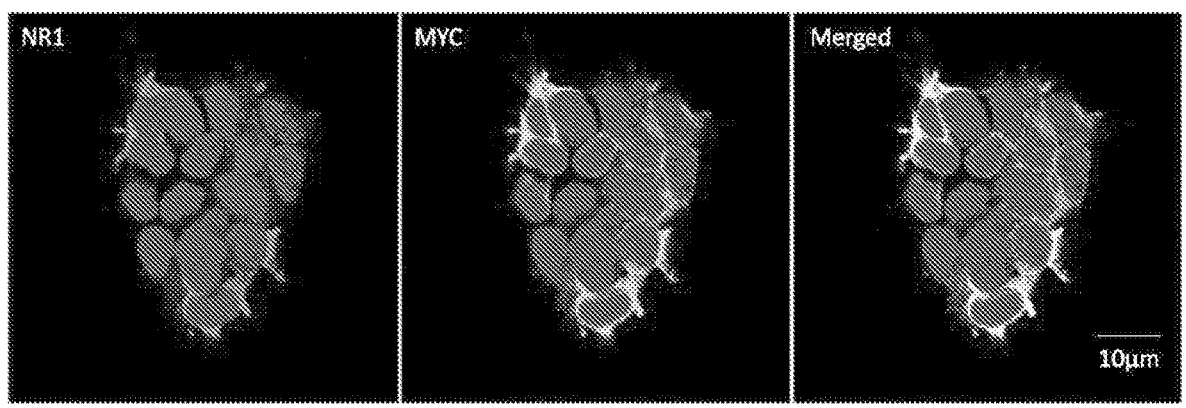
FIG. 20 shows immunofluorescence imaging of the NR1 ATD fusion protein on 293T-ATD cells. 293T-ATD cells were immunostained with a murine anti-NR1 mAb (red color, left panel) and the anti-Myc-tag mAb (green color, middle panel). A merged image is also shown (right panel). Nuclei were stained with DAPI, and the cells were visualized by confocal microscopy. Scale bar=10 μm

We tested the 293T-ATD cell line for detection of NR1 antibodies by immunofluorescence. We first co-stained the cells with the commercial NR1 and Myc antibodies and observed co-localization of the signals on the outer plasma membrane (FIG. 20).

We then tested binding of ANRE patient CSF, the three ANRE patient mAbs, and an isotype control human mAb, 8E1 (FIG. 21. CSF and the ANRE patient mAbs all reacted with the 293 T-ATD cell line, whereas the 8E1 mAb did not. ELISA studies of TEV protease-mobilized ATD showed the following results: The TEV protease site adjacent to the PDGF transmembrane domain was included to allow mobilization of the expressed ATD for use in binding studies requiring soluble antigen. We treated the 293T-ATD cells with TEV protease for 10-40 min, spun down the cells, and analyzed the reaction supernatants by capture ELISA and Coomassie-stained SDS:PAGE (FIGS. 22A-22B). Analyzed by ELISA, the ATD was evident at 10 min and peaked at 20 min, and declined somewhat thereafter (FIG. 22A). Longer incubations (up to 2 h) further decreased amount of mobilized ATD (data not shown). The non-denaturing SDS:PAGE gel gave a dominant band at approximately 25 kDa, with a faint band slightly below, and no significant bands above, demonstrating the specificity of cleavage of the ATD from the outer plasma membrane.

Figure 24:
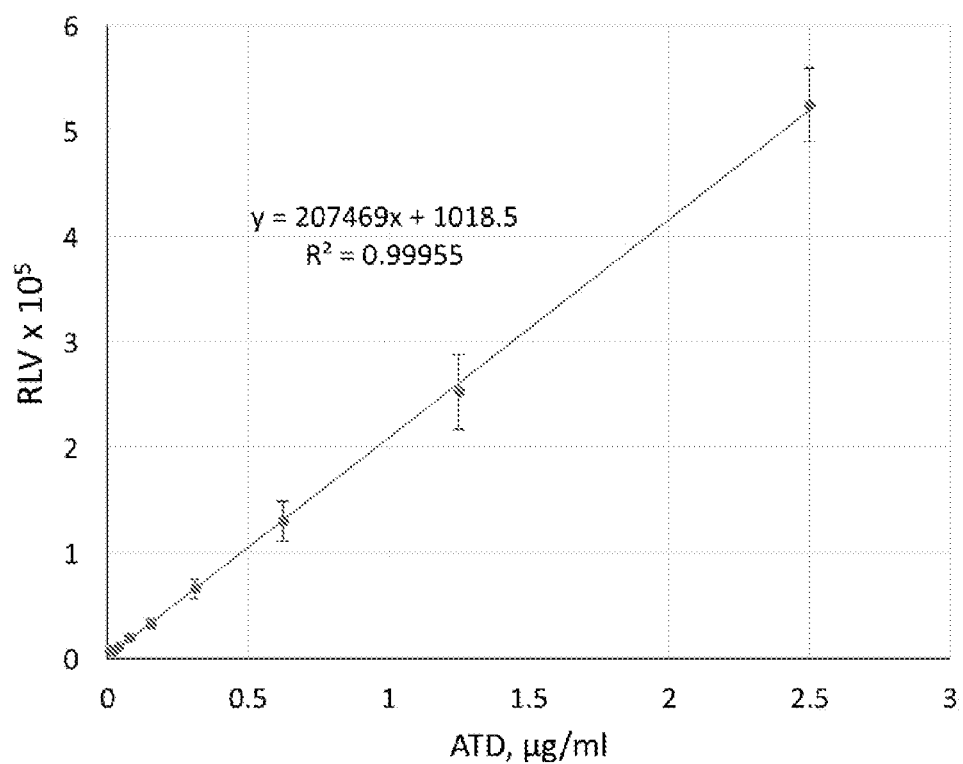
FIG. 24 is a graph showing titration of ATD protein in a capture ELISA. A titration of TEV-mobilized ATD was tested for binding to plate-adherent 5F5 mAb. ATD was biotinylated and tested from 65 pg/ml to 5 μg/ml, in triplicate samples, and detected with SA-HRP. The relative luminescence signal was measured. Calculated $R^2=0.99955$. RLV, relative luminescence value. Bars indicate the S.E.M.

We tested antibody binding to the mobilized ATD in a capture ELISA format. We used a Myc tag antibody to capture the ATD onto ELISA plates and tested binding of the commercial NR1 mAb and human ANRE mAbs. The murine NR1 mAb bound significantly above background levels (FIG. 23A). Similarly, the three human ANRE mAbs all bound the plate-adherent ATD, giving signals approximately 8-10 fold greater than the 6A human isotype control mAb (FIG. 23B). We tested whether the ATD could be used reproducibly in a quantitative assay. We biotinylated the ATD, then tested its binding to plate-immobilized 5F5 antibody in an ELISA, using SA-HRP for detection. We tested triplicate samples ranging from 65 pg/ml to 5 µg/ml (FIG. 24). Linear regression analysis gave an R2 value of 0.999, indicating that the assay is linear in this ATD concentration range.

Figure 25A:
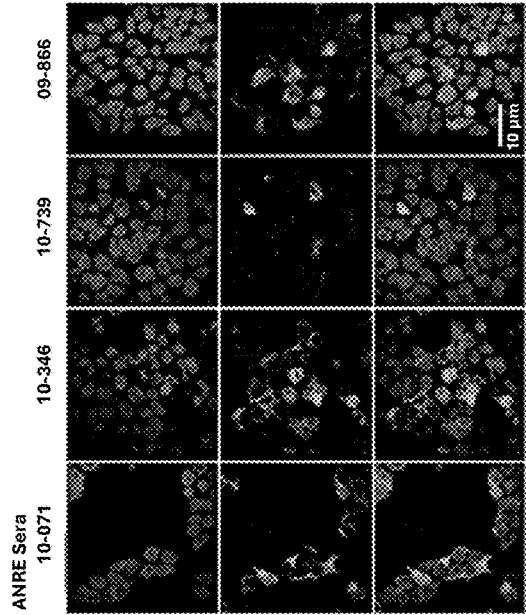
FIGS. 25A-25D show binding of ANRE and normal human CSF and sera to 293T-ATD cells by immunofluorescence. 293T-ATD cells were stained with ANRE patient CSF in FIG. 25A, with normal human CSF in FIG. 25B, with ANRE patient sera in FIG. 25C, and with normal human sera in FIG. 25D. Matched pairs include ANRE patient 10-071 (as seen in FIGS. 25A and 25C) and normal subjects 10-123 and 10-551 (as seen in FIGS. 25B and 25D). CSF were tested at 1:20 dilution; sera at 1:100. Human IgG binding is shown in red. Nuclei were stained with DAPI (blue) and the cells were visualized by confocal microscopy. Scale bars=10 μm.
Figure 25C:
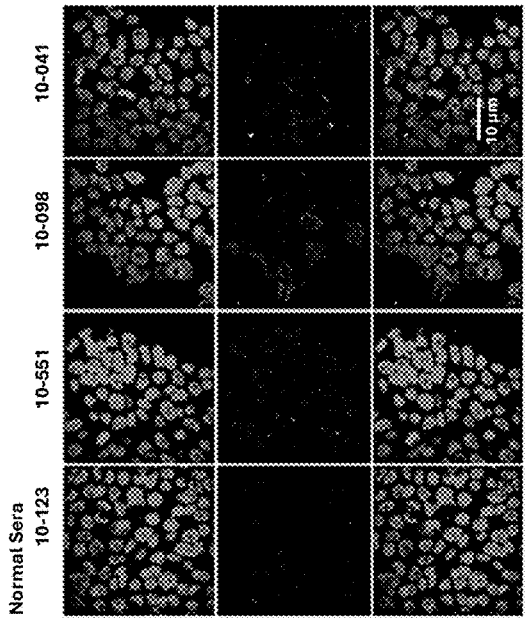
Figure 25B:
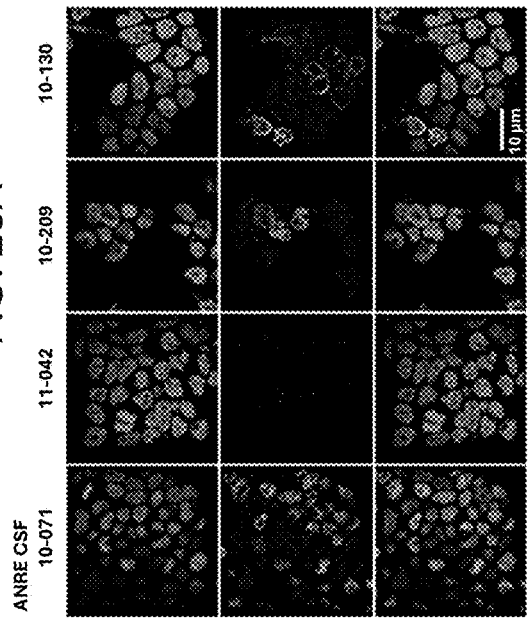
Figure 25D:
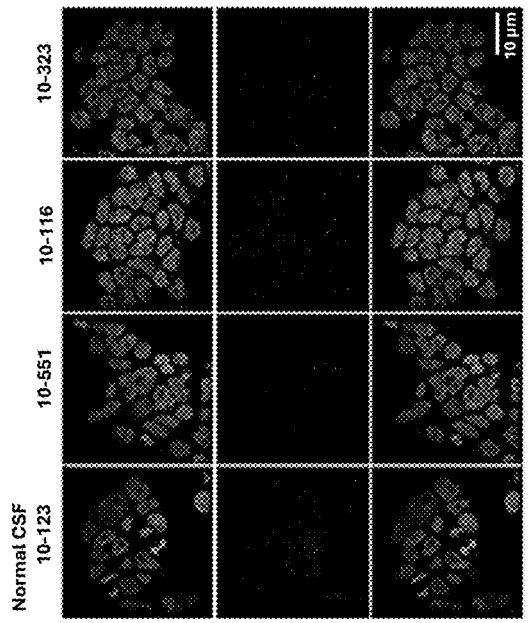

We tested binding of clinical samples of ANRE and normal CSF and sera to the 293T-ATD cell line by NR1 antibodies by immunofluorescence. Four ANRE and four normal human CSF (1:20) and serum samples (1:100) were tested, including a matched CSF:serum pair from ANRE patient 10-071 and two pairs from normal patients 10-123 and 10-551. Three of the ANRE CSF samples (FIG. 25A) and all four of the serum samples (FIG. 25C) gave a bright immunofluorescent signal, whereas none of the normal CSF or serum samples showed binding (FIGS. 25B and 25D).

Example 7: Diagnostic Method Employing Cell Line and Non-Overlapping Epitope-Binding Antibodies or Fragments Thereof Since, as described above, the mAbs 5F5, 1D1 and 2G6 bind non-overlapping epitopes on the NMDAR ATD, they are useful in assays requiring more than one control mAb. In one embodiment, a lateral flow assay is performed. In one embodiment, a labeled ATD (from the 293T cell line) can be loaded on a lateral flow pad. Once the sample, e.g., a polyclonal blood or serum sample from a patient, is loaded, any anti-ATD IgG flows to the right, capturing antigen. Then, in the test line, the floating sample/ATD encounters a diagnostic reagent containing one, two, or three of the anti-NMDAR mAbs that bind non-overlapping epitopes of NMDAR ATD. Such diagnostic reagent contains one, or a mixture of two or three of the mAbs 5F5, 2G6 or 1DA, or a mixture of recombinant or synthetic antibodies or binding fragments that bind the same epitopes as the mAbs. Contact with the diagnostic reagent precipitates the labeled ATD/antibody. The advantage of having multiple mAbs/fragments that bind non-overlapping epitopes is that there are multiple different chances to bind the antigen. In one embodiment, if the patient's anti-NMDAR antibodies (polyclonal) bind the same sites as one of the mAbs 5F5, 2G6 or 1D1 (or recombinant or synthetic antibodies or fragments having the same binding), the presence of antibodies or fragment that bind non-overlapping epitopes prevents a false negative.

Figure 26:
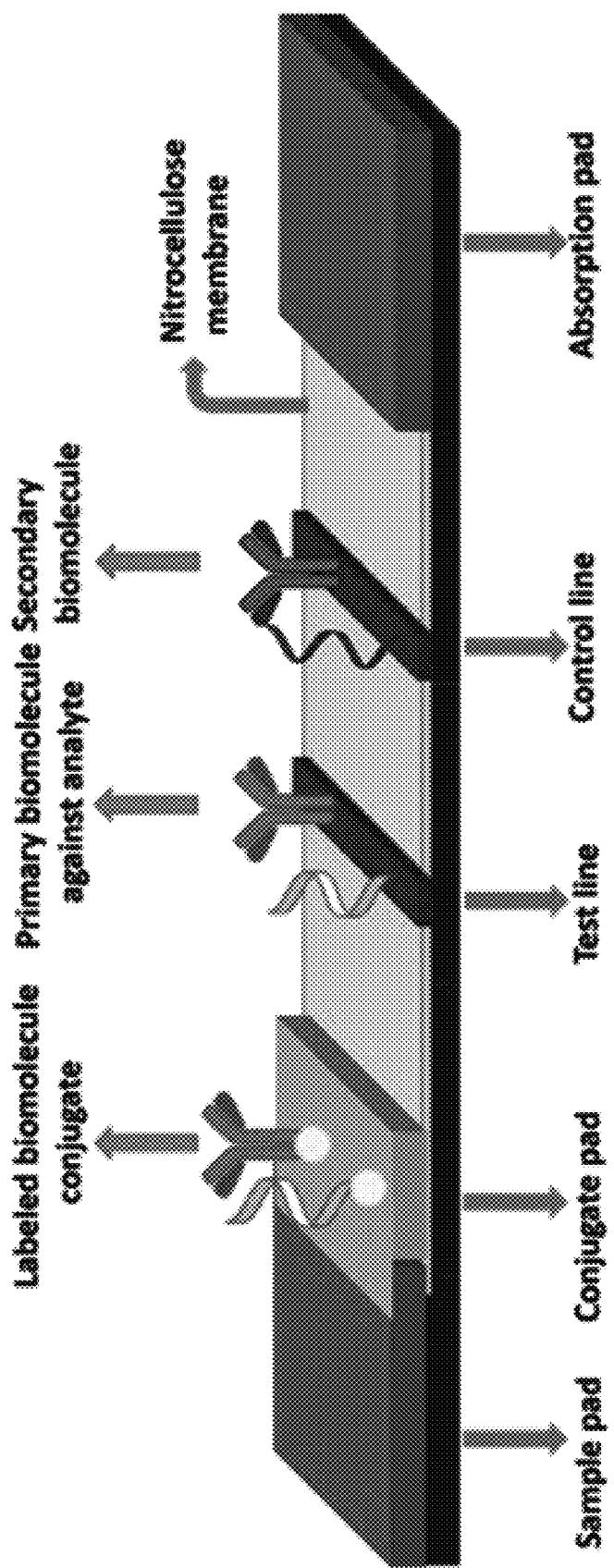
FIG. 26 is a schematic of a lateral flow assay as described in Example 7.

Similarly soluble ATD antigen released by TeV protease treatment of the ATD293T cell line can be used with the diagnostic reagent mAb/fragment mixture in a lateral flow assay or capture ELISA (in which the antigen is captured with one antibody and detected with another), such as outlined in the schematic of FIG. 26.

Each patent, patent application, and publication, including websites cited throughout specification are incorporated herein by reference. Similarly, the SEQ ID NOs which are referenced herein and which appear in the appended Sequence Listing are incorporated by reference. While the invention has been described with reference to particular embodiments, it will be appreciated that modifications can be made without departing from the spirit of the invention. Such modifications are intended to fall within the scope of the appended claims.

Sequence Listing Free Text

The following information is provided for sequences containing free text under numeric identifier <223>.

| SEQ ID NO: (containing free text) | Free text under <223> |
|---|---|
| 1 | 5F5 heavy chain nt |
| 2 | 5F5 light chain nt |
| 3 | 2G6 heavy chain nt |
| 4 | 2G6 light chain nt |
| 5 | 1D1 heavy chain nt |
| 6 | 1D1 light chain nt |
| 7 | NDMAR amino terminal domain |
| 8 | fusion protein of N-terminal extracellular domain of human GluNI fused to the Myc epitope tag, a 6XHIS tag, the Tobacco Etch Virus (TEV) protease cleavage site and TM domain of human PDGFR<br><222> (1) . . . (561)<br><223> Human NR1 amino terminal domain<br><222> (562) . . . (571)<br><223> Myc domain<br><222> (572) . . . (577)<br><223> PolyHis sequence<br><222> (578) . . . (585)<br><223> Tev protease<br><222> (586) . . . (635)<br><223> transmembrane domain of human PDGFR |
| 9 | <223> DNA sequence encoding the fusion protein of SEQ ID NO: 8 |
| 10 | 5F5 heavy chain AA<br>(97) . . . (117)<br><223> CDR region |
| 11 | 5F5 light chain AA<br>(88) . . . (101)<br><223> CDR region |
| 12 | 2G6 heavy chain AA<br>(97) . . . (120)<br><223> CDR region |
| 13 | 2G6 light chain AA<br>(87) . . . (99)<br><223> CDR region |
| 14 | 1D1 heavy chain AA<br>(97) . . . (109)<br><223> CDR region |
| 15 | 1D1 light chain AA<br>(91) . . . (101)<br><223> CDR region |
| 16 | <223> TEV protease site |
| 17 | <223> TEV protease site |

REFERENCES

1. Dalmau J, et al. Paraneoplastic anti-N methyl-D-aspartate receptor encephalitis associated with ovarian teratoma. Ann Neurol 2007; 61:25-36.
2. Armangue T, et al. Pediatric anti-N-methyl-D-aspartate receptor encephalitis-clinical analysis and novel findings in a series of 20 patients. J Pediatr 2013; 162:850-6e2.
3. Dalmau J, et al. Anti-NMDA receptor encephalitis: case series and analysis of the effects of antibodies. Lancet Neurol 2008; 7:1091.
4. Hughes E G, et al. Cellular and synaptic mechanisms of anti-NMDA receptor encephalitis. J Neurosci 2010; 30:5866-5875.
5. Zhang Q, et al. Suppression of synaptic plasticity by cerebrospinal fluid from anti-NMDA receptor encephalitis patients. Neurobiol Dis 2012; 45:610-615.
6. Regan M C, et al. A structural biology perspective on NMDA receptor pharmacology and function. Curr Opin Struct Biol 2015; 33:68-75.
7. Gleichman A J, et al. Anti-NMDA receptor encephalitis antibody binding is dependent on amino acid identity of a small region within the GluN1 amino terminal domain. J Neurosci 2012; 32:11082-11094.
8. Paoletti P, et al. NMDA receptor subunit diversity: impact on receptor properties, synaptic plasticity and disease. Nat Rev 2013; 14:383-400.
9. Kreye J, et al. Human cerebrospinal fluid monoclonal N-methyl-D-aspartate receptor autoantibodies are sufficient for encephalitis pathogenesis. Brain 2016; 139(Pt 10):2641-2652.
10. Puligedda R D, et al. Human monoclonal antibodies that neutralize vaccine and wildtype poliovirus strains. Antiviral Res 2014; 108:36-43.
11. Lai M, et al. AMPA receptor antibodies in limbic encephalitis alter synaptic receptorlocation. Ann Neurol 2009; 65:424-434.
12. Ho M, Pastan I. Display and selection of scFv antibodies on HEK-293T cells. Methods Mol Biol 2009; 562:99-113.
13. Erdile L F, et al. Whole cell ELISA for detection of tumor antigen expression in tumor samples. J Immunol Methods 2001; 258(1-2):47-53.
14. Adekar S P, et al. Hybridoma populations enriched for affinity-matured human IgGs yield high-affinity antibodies specific for botulinum neurotoxins J Immunol Methods 2008; 333(1-2):156-166.
15. Lim T S, et al. V-gene amplification revisited—An optimised procedure for amplification of rearranged human antibody genes of different isotypes. New Biotechnol 2010; 27:108-117.
16. Zhang J, et al. PEAR: a fast and accurate Illumina paired-end reAd mergeR. Bioinformatics 2014; 30:614-620.
17. Bolotin D A, et al. MiXCR: software for comprehensive adaptive immunity profiling. Nat Methods 2015; 12:380-381.
18. Katoh K, et al. MAFFT: a novel method for rapid multiple sequence alignment based on fast Fourier transform. Nucleic Acids Res 2002; 30:3059-3066.
19. Stamatakis A. RAxML version 8: a tool for phylogenetic analysis and post-analysis of large phylogenies. Bioinformatics 2014; 30:1312-1313.
20. Buchhalter J R, Dichter M A. Electrophysiological comparison of pyramidal and stellate nonpyramidal neurons in dissociated cell culture of rat hippocampus. Brain Res Bull 1991; 26:333-338.
21. van der Staay F J, et al. Effects of the cognition impairer MK-801 on learning and memory in mice and rats. Behav Brain Res 2011; 220:215-229.
22. Karakas E, et al. Emerging structural insights into the function of ionotropic glutamate receptors. Trends Biochem Sci 2015; 40:328-337.
23. Al-Saleem F H, et al. RBC adherence of immune complexes containing botulinum toxin improves neutralization and macrophage uptake. Toxins 2017; 9: e173.
24. Lefranc M P. IMGT, the International ImMunoGeneTics Information System. Cold Spring Harb Protoc 2011; 595-603.
25. Xu J L, Davis M M. Diversity in the CDR3 region of V(H) is sufficient for most antibody specificities. Immunity 2000; 13:37-45.
26. Adie E J, et al. A pH-sensitive fluor, CypHer 5, used to monitor agonist-induced G proteincoupled receptor internalization in live cells. Biotechniques 2002; 33:1152-4, 1156-7.
27. Joshi S G, et al. Modulation of botulinum toxin-induced changes in neuromuscular function with antibodies directed against recombinant polypeptides or fragments. Neuroscience 2011; 179:208-222.
28. Jangula A, Murphy E J. Lipopolysaccharide-induced blood brain barrier permeability is enhanced by alpha-synuclein expression. Neurosci Lett 2013; 551:23-27.

29. Malviya M, et al. NMDAR encephalitis: passive transfer from man to mouse by a recombinant antibody. Ann Clin Transl Neurol. 2017; 4:768-783.
30. Lynch D R, Guttmann R P. Excitotoxicity: perspectives based on N-methyl-D-aspartate receptor subtypes. J Pharmacol Exp Ther 2002; 300:717-723.
31. Moscato E H, et al. Acute mechanisms underlying antibody effects in anti-N-methyl-D-aspartate receptor encephalitis. Ann Neurol 2014; 76:108-119.
32. Mikasova L, et al. Disrupted surface cross-talk between NMDA and Ephrin-B2 receptors in anti-NMDA encephalitis. Brain 2012; 135(Pt 5):1606-1621.
33. Javitt D C. Glutamate and schizophrenia: phencyclidine, N methyl-D-aspartate receptors, and dopamine-glutamate interactions. Int Rev Neurobiol 2007; 78:69-108.
34. Belforte J E, et al. Postnatal NMDA receptor ablation in corticolimbic interneurons confers schizophrenia-like phenotypes. Nat Neurosci 2010; 13:76-83.
35. Masdeu J C, et al. NMDA receptor internalization by autoantibodies: a reversible mechanism underlying psychosis? Trends Neurosci 2016; 39:300-310.
36. Mohn A R, et al. Mice with reduced NMDA receptor expression display behaviors related to schizophrenia. Cell 1999; 98:427-436.
37. Barker-Haliski M, White H S. Glutamatergic mechanisms associated with seizures and epilepsy. Cold Spring Harb Perspect Med 2015; 5:a022863.
38. Dalmau J, et al. Autoantibodies to synaptic receptors and neuronal cell surface proteins in autoimmune diseases of the central nervous system. Physiol Rev. 2017; 97(2):839-87.
39. Graus F, et al. A clinical approach to diagnosis of autoimmune encephalitis. Lancet Neurol. 2016; 15(4): 391-404.
40. Gresa-Arribas N, et al. Antibody titres at diagnosis and during follow-up of anti-NMDA receptor encephalitis: a retrospective study. Lancet Neurol. 2014; 13(2):167-77.
41. Dalton A C, Barton W A. Over-expression of secreted proteins from mammalian cell lines. Protein Sci. 2014; 23(5):517-25.
42. Karakas E, Furukawa H. Crystal structure of a heterotetrameric NMDA receptor ion channel. Science. 2014; 344(6187):992-7.
43. Morgenstern J P, et al. Advanced mammalian gene transfer: high titre retroviral vectors with multiple drug selection markers and a complementary helper-free packaging cell line. Nucleic Acids Res. 1990; 18(12):3587-96.
44. Sharma, R. et al, Membrane-bound and soluble forms of an NMDA receptor extracellular domain retain epitopes targeted in auto-immune encephalitis, BMC Biotechnol., June 2018; 18:41
45. Sharma, R. et al, Monoclonal antibodies from a patient with anti-NMDA receptor encephalitis. Ann. Clin. Translational Neurology. July 2018; 5(8):935-951

The invention claimed is:

1. A recombinant, synthetic, or monoclonal human antibody or antigen binding fragment thereof that specifically binds to an N-methyl-D-aspartate Receptor (NMDAR) protein comprising the amino acid sequence of SEQ ID NO: 7, said antibody or antigen binding fragment thereof comprising:
   i. a heavy chain variable domain sequence comprising the amino acid sequence of SEQ ID NO: 10 and a light chain variable domain sequence comprising the amino acid sequence of SEQ ID NO: 11;
   ii. a heavy chain variable domain sequence comprising the amino acid sequence of SEQ ID NO: 12 and a light chain variable domain sequence comprising the amino acid sequence of SEQ ID NO: 13; or
   iii. a heavy chain variable domain sequence comprising the amino acid sequence of SEQ ID NO: 14 and a light chain variable domain sequence comprising the amino acid sequence of SEQ ID NO: 15,
   wherein the antibody or antigen binding fragment thereof is coupled covalently or non-covalently to a detectable label.

2. The antibody or antigen binding fragment thereof according to claim 1, wherein the heavy chain variable domain sequence comprising the amino acid sequence of SEQ ID NO: 10 is encoded by a nucleic acid sequence comprising the nucleic acid sequence of SEQ ID NO: 1, and the light chain variable domain sequence comprising the amino acid sequence of SEQ ID NO: 10 is encoded by a nucleic acid sequence comprising the nucleic acid sequence of SEQ ID NO: 2.

3. The antibody or antigen binding fragment thereof according to claim 1, wherein the heavy chain variable domain sequence comprising the amino acid sequence of SEQ ID NO: 12 is encoded by a nucleic acid sequence comprising the nucleic acid sequence of SEQ ID NO: 3, and the light chain variable domain sequence comprising the amino acid sequence of SEQ ID NO: 13 is encoded by a nucleic acid sequence comprising the nucleic acid sequence of SEQ ID NO: 4.

4. The antibody or antigen binding fragment thereof according to claim 1, wherein the heavy chain variable domain sequence comprising the amino acid sequence of SEQ ID NO: 14 is encoded by a nucleic acid sequence comprising the nucleic acid sequence of SEQ ID NO: 5, and the light chain variable domain sequence comprising the amino acid sequence of SEQ ID NO: 15 is encoded by a nucleic acid sequence comprising the nucleic acid sequence of SEQ ID NO: 6.

5. The antibody or antigen binding fragment thereof according to claim 1, which is an IgG or comprises an IgG backbone.

6. The antibody or antigen binding fragment thereof according to claim 1, wherein the antibody or antigen binding fragment thereof specifically binds an extracellular amino terminal domain (ATD) of Glutamate Ionotropic Receptor (GluN1) of the NMDAR protein comprising the amino acid sequence of SEQ ID NO: 7.

7. A composition comprising a mixture of at least two antibodies or antigen binding fragments thereof according to claim 1.

8. The composition according to claim 7, wherein each of the at least two antibodies or antigen binding fragments thereof in the mixture is immobilized on a substrate.

9. The composition according to claim 7, comprising three different antibodies or antigen binding fragments thereof of claim 1.

10. An assay method for detecting autoantibodies in a biological sample obtained from a subject, the method comprising:
  i. contacting the biological sample with an antigen comprising the extracellular amino terminal domain (ATD) of Glutamate Ionotropic Receptor (GluN1) of NMDAR comprising the amino acid sequence of SEQ ID NO: 7 to form a complex; and
  ii. detecting the level of autoantibodies in the biological sample, the detection comprising contacting the complex with the antibody or antibody fragment thereof of claim 1 or the composition of claim 7 to detect the complex.

\* \* \* \* \*